(12) United States Patent
Sayre

(10) Patent No.: US 10,745,708 B2
(45) Date of Patent: Aug. 18, 2020

(54) TRANSGENIC PLANTS WITH ENGINEERED REDOX SENSITIVE MODULATION OF PHOTOSYNTHETIC ANTENNA COMPLEX PIGMENTS AND METHODS FOR MAKING THE SAME

(71) Applicant: NMC, INC., Los Alamos, NM (US)

(72) Inventor: Richard Thomas Sayre, Los Alamos, NM (US)

(73) Assignee: NMC, INC., Los Alamos, NM (US)

(*) Notice: Subject to any disclaimer, the term of this patent is extended or adjusted under 35 U.S.C. 154(b) by 232 days.

(21) Appl. No.: 15/594,274

(22) Filed: May 12, 2017

(65) Prior Publication Data

US 2017/0356001 A1    Dec. 14, 2017

Related U.S. Application Data

(63) Continuation of application No. PCT/US2015/060448, filed on Nov. 12, 2015.

(60) Provisional application No. 62/078,936, filed on Nov. 12, 2014.

(51) Int. Cl.
    *C12N 15/82* (2006.01)
    *C12N 9/02* (2006.01)

(52) U.S. Cl.
    CPC ....... *C12N 15/8237* (2013.01); *C12N 9/0073* (2013.01); *C12N 15/825* (2013.01); *C12N 15/8222* (2013.01); *C12N 15/8245* (2013.01); *C12N 15/8261* (2013.01); *C12N 15/8269* (2013.01); *C12Y 114/13122* (2013.01); *Y02A 40/146* (2018.01)

(58) Field of Classification Search
    CPC .................................................. C12N 15/8237
    See application file for complete search history.

(56) References Cited

U.S. PATENT DOCUMENTS

| | | | |
|---|---|---|---|
| 4,535,060 A | 8/1985 | Comai |
| 4,940,935 A | 7/1990 | Riley |
| 5,034,323 A | 7/1991 | Jorgensen et al. |
| 5,164,316 A | 11/1992 | McPherson et al. |
| 5,188,642 A | 2/1993 | Shah |
| 5,196,525 A | 3/1993 | McPherson et al. |
| 5,231,020 A | 7/1993 | Jorgensen et al. |
| 5,254,801 A | 10/1993 | Dotson et al. |
| 5,283,184 A | 2/1994 | Jorgensen et al. |
| 5,302,523 A | 4/1994 | Coffee et al. |
| 5,322,783 A | 6/1994 | Tomes et al. |
| 5,322,938 A | 6/1994 | McPherson et al. |
| 5,352,605 A | 10/1994 | Fraley et al. |
| 5,359,142 A | 10/1994 | McPherson et al. |
| 5,378,619 A | 1/1995 | Rogers |
| 5,384,253 A | 1/1995 | Krzyzek et al. |
| 5,391,725 A | 2/1995 | Coruzzi et al. |
| 5,424,200 A | 6/1995 | McPherson et al. |
| 5,428,147 A | 6/1995 | Barker et al. |
| 5,447,858 A | 9/1995 | Key et al. |
| 5,464,765 A | 11/1995 | Coffee et al. |
| 5,508,184 A | 4/1996 | Negrutiu et al. |
| 5,508,468 A | 4/1996 | Lundquist et al. |
| 5,523,311 A | 6/1996 | Schurter et al. |
| 5,527,695 A | 6/1996 | Hodges et al. |
| 5,538,880 A | 7/1996 | Lundquist et al. |
| 5,538,887 A | 7/1996 | Peindl et al. |
| 5,550,318 A | 8/1996 | Adams et al. |
| 5,563,055 A | 10/1996 | Townsend et al. |
| 5,591,616 A | 1/1997 | Hiei et al. |
| 5,593,874 A | 1/1997 | Brown et al. |
| 5,608,144 A | 3/1997 | Baden et al. |
| 5,610,042 A | 3/1997 | Chang et al. |
| 5,614,395 A | 3/1997 | Ryals et al. |
| 5,614,399 A | 3/1997 | Quail et al. |
| 5,627,061 A | 5/1997 | Barry et al. |
| 5,633,435 A | 5/1997 | Barry et al. |
| 5,633,441 A | 5/1997 | De Greef et al. |
| 5,641,876 A | 6/1997 | McElroy et al. |
| 5,658,772 A | 8/1997 | Odell |
| 5,659,122 A | 8/1997 | Austin |
| 5,780,708 A | 7/1998 | Lundquist et al. |
| 5,981,840 A | 11/1999 | Zhao et al. |
| 6,118,047 A | 9/2000 | Anderson et al. |

(Continued)

FOREIGN PATENT DOCUMENTS

| DE | 3642829 | 5/1988 |
|---|---|---|
| EP | 0342926 | 11/1989 |

(Continued)

OTHER PUBLICATIONS

Belhaj, K. et al., Plant Methods, published Oct. 11, 2013; vol. 9, No. 39, pp. 1-10. (Year: 2013).*

Amin, Pinky, et al., "*Arabidopsis* Mutants Lacking the 43- and 54-Kilodalton Subunits of the Chloroplast Signal Recognition Particle Have Distinct Phenotypes", Plant Physiology, vol. 121, 1999, 61-70.

Klimyuk, Victor I., et al., "A Chromodomain Protein Encoded by the *Arabidopsis* CAO Gene Is a Plant-Specific Component of the Chloroplast Signal Recognition Particle Pathway That Is Involved in LHCP Targeting", The Plant Cell, vol. 11, 1999, 87-99.

Sakuraba, Yasuhito, et al., "Determination of a Chloroplast Degron in the Regulatory Domain of Chlofophyllide a Oxygenase", The Journal of Biological Chemistry, vol. 284, No. 52, 2009, 36689-36699.

(Continued)

*Primary Examiner* — Russell Kallis
(74) *Attorney, Agent, or Firm* — Peacock Law P.C.; Janeen Vilven

(57) ABSTRACT

Embodiments of the present invention provide for a transgenic plan, methods of making and DNA constructs for use in the transgenic plant which transgenic plant is capable of modulating its photosynthetic antenna complex composition in response to increases or decreases in light intensity by modulation of the ratio of chlorophyll a to chlorophyll b such that there is an increase in the Chl a/b ratio at high light intensity and a decrease in the Chl a/b ratio at low light intensity versus wild-type plants grown in the same conditions.

15 Claims, 18 Drawing Sheets

Specification includes a Sequence Listing.

(56) References Cited

U.S. PATENT DOCUMENTS

| | | | |
|---|---|---|---|
| 6,232,526 | B1 | 5/2001 | McElroy et al. |
| 6,509,154 | B1 | 1/2003 | De Paillette |
| 6,566,587 | B1 | 5/2003 | Lebrun et al. |
| 8,697,359 | B1 | 4/2014 | Zhang |
| 2003/0221211 | A1 | 11/2003 | Rottmann et al. |
| 2004/0029283 | A1 | 2/2004 | Fillatti |

FOREIGN PATENT DOCUMENTS

| | | | | |
|---|---|---|---|---|
| WO | 92/17598 | | 10/1992 | |
| WO | 95/06128 | | 3/1995 | |
| WO | 97/41228 | | 11/1997 | |
| WO | 99/32619 | | 7/1999 | |
| WO | 99/60129 | | 11/1999 | |
| WO | 00/001846 | | 1/2000 | |
| WO | 00/44895 | | 8/2000 | |
| WO | 00/44914 | | 8/2000 | |
| WO | 00/63364 | | 10/2000 | |
| WO | 01/29058 | | 4/2001 | |
| WO | 01/36646 | | 5/2001 | |
| WO | 01/75164 | | 10/2001 | |
| WO | 02/44321 | | 6/2002 | |
| WO | 02/055692 | | 7/2002 | |
| WO | 2005/054439 | | 6/2005 | |
| WO | 2005/110068 | | 11/2005 | |
| WO | 2013/016267 | | 1/2013 | |
| WO | WO 2013/016267 | * | 1/2013 | ............... C12N 1/13 |
| WO | WO-2013016267 A2 | * | 1/2013 | ............... C12P 7/64 |
| WO | 2016/077624 | | 5/2016 | |

OTHER PUBLICATIONS

Sayre, Richart, "Making Next Generation Biofuel Systems Work", Los Alamos National Laboratory, http://acee.princeton.edu/wp-content/uploads/2014/04/Richard-Sayre-Presentation.pdf, 2014, 1-51.

Ali, Nusrat, et al., "RNA interference in designing transgenic crops", GM Crops, vol. 1, 2010, 207-213.

Altschul, Stephen F., et al., "Basic Local Alignment Search Tool", J. Mol. Biol., vol. 215, 1990, 403-410.

Altschul, Stephen F., et al., "Gapped Blast and PSI-Blast: a new generation of protein database search programs", Nucleic Acids Research, vol. 25, No. 17, 1997, 3389-3402.

Bechtold, Nicole, et al., "In Planta Agrobacterium Mediated Transformation of Adult *Arabidopsis thaliana* Plants by Vacuum Infiltration", Methods in Molecular Biology, vol. 82, 1998, 259-266.

Betterle, Nico, et al., "Light-induced Dissociation of an Antenna Hetero-oligomer Is Needed for Non-photochemical Quenching Induction", The Journal of Biological Chemistry, vol. 284, No. 22, 2009, 15255-15266.

Bhattacharya, Debashish, et al., "Nuclear-Encoded rDNA Group I Introns: Origin and Phylogenetic Relationships of Insertion Site Lineages in the Green Algae", Mol. Biol. Evol., vol. 13, No. 7, 1996, 978-989.

Blankenship, Robert E., "Early Evolution of Photosynthesis", Plant Physiology, vol. 154, 2010, 434-438.

Boekema, Egbert J., et al., "Supramolecular organization of photosystem II and its light-harvesting antenna in partially solubilized photosystem II membranes", Eur. J. Biochem., vol. 266, No. 2, 1999, 444-452.

Brandes, Nicolas, et al., "Thiol-Based Redox Switches in Eukaryotic Proteins", Antioxidants & Redox Signaling, vol. 11, No. 5, 2009, 997-1014.

Brummelkamp, Thijn R., et al., "A System for Stable Expression of Short Interfering RNAs in Mammalian Cells", Science, vol. 296, No. 5567, 2002, 550-553.

Bucher, Philipp, et al., "A Generalized Profile Syntax for Biomolecular Sequence Motifs and its Function in Automatic Sequence Interpretation", Proceedings of the Second International Conference on Intelligent Systems for Molecular Biology, 1994, 53-61.

Caffarri, Stefano, et al., "Functional architecture of higher plant photosystem II supercomplexes", The EMBO Journal, vol. 28, No. 19, 2009, 3052-3063.

Carrillo, Humberto, et al., "The Multiple Sequence Alignment Problem in Biology", SIAM Journal on Applied Mathematics, vol. 48, No. 5, 1988, 1073-1082.

Cech, Thomas R., "Self-Splicing of Group I Intr.ons", Annu. Rev. Biochem., vol. 59, 1990, 543-568.

Chaikam, Vijay, et al., "Comparison of structure, function and regulation of plant cold shock domain proteins to bacterial and animal cold shock domain proteins", BMB Reports, vol. 43, No. 1, 2010, 1-8.

Chattopadhyay, Sudip, et al., "*Arabidopsis* bZIP Protein HY5 Directly Interacts with Light-Responsive Promoters in Mediating Light Control of Gene Expression", The Plant Cell, vol. 10, 1998, 673-683.

Chuang, Chiou-Fen, et al., "Specific and heritable genetic interference by double-stranded RNA in *Arabidopsis thaliana*", Proc. Natl. Acad. Sci USA, vol. 97, No. 9, 20000, 4985-4990.

Clough, Steven J., et al., "Floral dip: a simplified method for Agrobacterium-mediated transformation of *Arabidopsis thaliana*", The Plant Journal, vol. 16, No. 6, 1998, 735-743.

Coman, D., et al., "Transcript profiling in *Arabidopsis* with genome tiling microarrays", Methods Mol Biol., vol. 1067, 2013, 35-49.

Cong, Le, et al., "Multiplex Genome Engineering Using CRISPR/Cas Systems", Science, vol. 339, 2013, 819-823.

De Bianchi, Silvia, et al., "Minor Antenna Proteins CP24 and CP26 Affect the Interactions between Photosystem II Subunits and the Electron Transport Rate in Grana Membranes of *Arabidopsis*", The Plant Cell, vol. 20, No. 4, 2008, 1012-1028.

Durnford, Dion G., et al., "Light-harvesting complex gene expression is controlled by both transcriptional and post-transcriptional mechanisms during photoacclimation in Chlamydomonas reinhardtii", Physiologia Plantarum, vol. 118, 2003, 193-205.

Eberhard, Stephan, et al., "The Dynamics of Photosynthesis", Annu. Rev. Genet., vol. 42, 2008, 463-515.

Fire, Andrew, "Potent and specific genetic interference by double-stranded RNA in Caenorhabditis elegans", Nature, vol. 391, 1998, 806-811.

Flavell, R. B., "Inactivation of gene expression in plants as a consequence of specific sequence duplication", Proc. Natl. Acad. Sci. USA, vol. 91, No. 9, 1994, 3490-3496.

Foiani, Marco, et al., "GCD2, a Translational Repressor of the GCN4 Gene, Has a General Function in the Initiation of Protein Synthesis in *Saccharomyces cerevisiae*", Molecular and Cellular Biology, vol. 11, No. 6, 1991, 3203-3216.

Gaj, Thomas, et al., "ZFN, TALEN and CRISPR/Cas-based methods for genome engineering", Trends Biotechnol., vol. 31, No. 7, 2013, 397-405.

Hammond, Scott M., et al., "Post-transcriptional gene silencing by double-stranded RNA", Nature Review Genetics, vol. 2, 2001, 110-119.

Haseloff, Jim, et al., "Simple RNA enzymes with new and highly specific endoribonuclease activities", Nature, vol. 334, 1988, 585-591.

Hofmann, Kay, et al., "The Prosite database, its status in 1999", Nucleic Acids Research, vol. 27, No. 1, 1999, 215-219.

Jarvi, Sari, et al., "Optimized native gel systems for separation of thylakoid protein complexes: novel super- and mega-complexes", Biochemical Journal, vol. 439, No. 2, 2011, 207-214.

Jinks-Robertson, Sue, et al., "Ribosomal Protein S4 Acts in trans as a Translational Repressor to Regulate Expression of the alpha Operon in *Escherichia coli*", Journal of Bacteriology, vol. 151, No. 1, 1982, 193-202.

Jozwik, CE, et al., "RNA-protein interactions of the bacteriophage RB69 RegA translational repressor protein", Nucleic Acids Symp Ser., vol. 33, 1995, 256-257.

Kausch, Albert P., et al., "Mesophyll-specific, light and metabolic regulation of the C4 PPCZm1 promoter in transgenic maize", Plant Molecular Biology, vol. 45, No. 1, 2001, 1-15.

Kirst, Henning, et al., "The chloroplast signal recognition particle (CpSRP) pathway as a tool to minimize chlorophyll antenna size and maximize photosynthetic productivity", Biotechnology Advances 32, 2014, 66-72.

(56) References Cited

OTHER PUBLICATIONS

Kirst, Henning, et al., "Truncated Photosystem Chlorophyll Antenna Size in the Green Microalga *Chlamydomonas reinhardtii* upon Deletion of the TLA3-CpSRP43 Gene", Plant Physiology, vol. 160, 2012, 2251-2260.

Kooter, Jan M., "Trans-inactivation of gene expression in plants", Current Opinion in Biotechnology, vol. 4, No. 2, 1993, 166-171.

Kovacs, Laszlo, et al., "Lack of the Light-Harvesting Complex CP24 Affects the Structure and Function of the Grana Membranes of Higher Plant Chloroplasts", The Plant Cell, vol. 18, No. 11, 2006, 3106-3120.

Krieger-Liszkay, Anja, et al., "Singlet oxygen production in photosystem II and related protection mechanism", Photosynth Res, vol. 98, 2008, 551-564.

Leviatan, Noam, et al., "Genome-Wide Survey of Cold Stress Regulated Alternative Splicing in *Arabidopsis thaliana* with Tiling Microarray", PLOS One, vol. 8, No. 6, 2013, e66511.

Lu, Chaofu, et al., "Generation of transgenic plants of a potential oilseed crop *Camelina sativa* by Agrobacterium-mediated transformation", Plant Cell Rep, vol. 27, 2008, 273-278.

Matsuoka, Makoto, et al., "Tissue-specific light-regulated expression directed by the promoter of a C4 gene, maize pyruvate,orthophosphate dikinase, in a C3 plant, rice", Proc. Natl. Acad. Sci. USA, vol. 90, 1993, 9586-9590.

Minagawa, Jun, et al., "Structure, function and assembly of Photosystem II and its light-harvesting proteins", Photosynthesis Research, vol. 82, 2004, 241-263.

Morita, Ryouhei, et al., "Characterization of Chlorophyllide a Oxygenase (CAO) in Rice", Breeding Science, vol. 55, 2005, 361-364.

Mueller, Andre Hubertus, et al., "Characterization of Mutations in Barley fch2 Encoding Chlorophyllide a Oxygenase", Plant Cell Physiol., vol. 53, No. 7, 2012, 1232-1246.

Muller, Patricia, et al., "Non-Photochemical Quenching. A Response to Excess Light Energy", Plant Physiol., vol. 125, 2001, 1558-1566.

Mussgnug, Jan H., et al., "NAB1 Is an RNA Binding Protein Involved in the Light-Regulated Differential Expression of the Light-Harvesting Antenna of Chlamydomonas reinhardtii", The Plant Cell, vol. 17, 2005, 3409-3421.

Nakaminami, Kentaro, et al., "Functional conservation of cold shock domains in bacteria and higher plants", PNAS, vol. 103, No. 26, 2006, 10122-10127.

Nakanishi, Hiromitsu, et al., "Characterization of the *Arabidopsis thaliana* Mutant pcb2 which Accumulates Divinyl Chlorophylls", Plant Cell Physiol., vol. 46, No. 3, 2005, 467-473.

Napoli, Carolyn, et al., "Introduction of a Chimeric Chalcone Synthase Gene into Petunia Results in Reversible Co-Suppression of Homologous Genes in trans", The Plant Cell, vol. 2, 1990, 279-289.

Neale, Patrick J., et al., "Algal Photosynthetic Membrane Complexes and the Photosynthesis-Irradiance Curve: A Comparison of Light-Adaptation Responses in Chi^amydomoxas neixhardtii (chlorophyta)", J. Phycol., vol. 22, 1986, 531-538.

Nomura, Mika, "The evolution of C4 plants: acquisition of cis-regulatorysequences in the promoter of C4-type pyruvate,orthophosphate dikinase gene", The Plant Journal, vol. 22, No. 3, 2000, 211-221.

Paddison, Patrick J., et al., "Short hairpin RNAs (shRNAs) induce sequence-specific silencing in mammalian cells", Genes & Development, vol. 16, 2002, 948-958.

Paget, Mark S.B., et al., "Thiol-based regulatory switches", Annu. Rev. Genet., vol. 37, 2003, 91-121.

Perrine, Zoee, et al., "Optimization of photosynthetic light energy utilization by microalgae", Algal Research 1, 2012, 134-142.

Polle, Juergen E.W., et al., "Absence of Lutien, Violaxanthin and Neoxanthin Affects the Functional Chlorophyll Antenna Size of Photosystem-II but not that of Photosystem-I in the Green Alga *Chlamydomonas reinhardtii*", Plant Cell Physiol., vol. 42, No. 5, 2001, 482-491.

Polle, Juergen E.W., et al., "Photosynthetic apparatus organization and function in the wild type and a chlorophyll b-less mutant of Chlamydomonas reinhardtii. Dependence on carbon sourse", Planta, vol. 211, 20000, 335-344.

Polle, Juergen E.W., et al., "Truncated chlorophyll antenna size of the photosystems—a practical method to improve microalgal productivity and hydrogen production in mass culture", International Journal of Hydrogen Energy, vol. 27, 2002, 1257-1264.

Reeck, Gerald R., ""Homology" in Proteins and Nucleic Acids: A Terminology Muddle and a Way out of It", Cell, vol. 50, 1987, 667.

Saccomanno, Lisa, et al., "The Star protein QKI-6 is a translational repressor", PNAS, vol. 96, No. 22, 1999, 12605-12610.

Sanders, Erin R., et al., "Occurrence of MATK in a TRNK Group II Intron in Charophyte Green Algae and Phylogeny of the Characeae", American Journal of Botany, vol. 90, No. 4, 2003, 628-633.

Si, Li-Zhen, "Deletion of 93 bp Far-upstream Fragment of Rice Cytosolic Fructose-1, 6-Bisphosphatase Promoter Completely Alter Its Expression Pattern", Acta Botanica Sinica, vol. 44, No. 11, 2002, 1339-1345.

Tada, Yuichi, "Expression of a monocot LHCP promoter in transgenic rice", The EMBO Journal, vol. 10, No. 7, 1991, 1803-1808.

Tanaka, Ryouichi, "Overexpression of chlorophyllide a oxygenase (CAO) enlarges the antenna size of photosystem II in *Arabidopsis thaliana*", The Plant Journal, vol. 26, No. 4, 2001, 365-373.

Timmons, Lisa, et al., "Specific interference by ingested dsRNA", Nature, vol. 395, 1998, 854.

Turmel, Monique, et al., "Group I introns interrupt the chloroplast psaB and psbC and the mitochondrial rrnL gene in Chlamydomonas", Nucleic Acids Research, vol. 21, No. 22, 1993, 5242-5250.

Van Oppen, Madeleine J.H., et al., "Evidence for independent acquisition of group I introns in green algae.", Mol. Biol. Evol., vol. 10, No. 6, 1993, 1317-1326.

Vass, Imre, et al., "Janus-faced charge recombinations in photosystem II photoinhibition", Trends in Plant Science, vol. 14 No. 4, 2009, 200-205.

Waterhouse, Peter M., et al., "Virus resistance and gene silencing in plants can be induced by simultaneous expression of sense and antisense RNA", Proc. Natl. Acad. Sci. USA, vol. 95, No. 23, 1998, 13959-13964.

Wobbe, Lutz, "Cysteine modification of a specific repressor protein controls the translational status of nucleus-encoded LHCII mRNAs in Chlamydomonas", PNAS, vol. 106, No. 32, 2009, 13290-13295.

Yanagisawa, Shuichi, et al., "Involvement of Maize Dof Zinc Finger Proteins in Tissue-Specific and Light-Regulated Gene Expression", The Plant Cell, vol. 10, 1998, 75-89.

Yang, Zhipan, et al., "Functional analysis of the rice rubisco activase promoter in transgenic *Arabidopsis*", Biochemical and Biophysical Research Communications vol. 418, No. 3, 2012, 565-570.

Berger, Hanna, et al., "A Light Switch Based on Protein S-Nitrosylation Fine-Tunes Photosynthetic Light Harvesting in Chlamydomonas", Plant Physiology, vol. 171, 2016, 821-832.

Wobbe, Lutz, et al., "Cysteine modification of a specific repressor protein controls the translational status of nucleus-encoded LHCII mRNAs in Chlamydomonas", PNAS, vol. 106, No. 32, 2009, 13290-13295.

\* cited by examiner

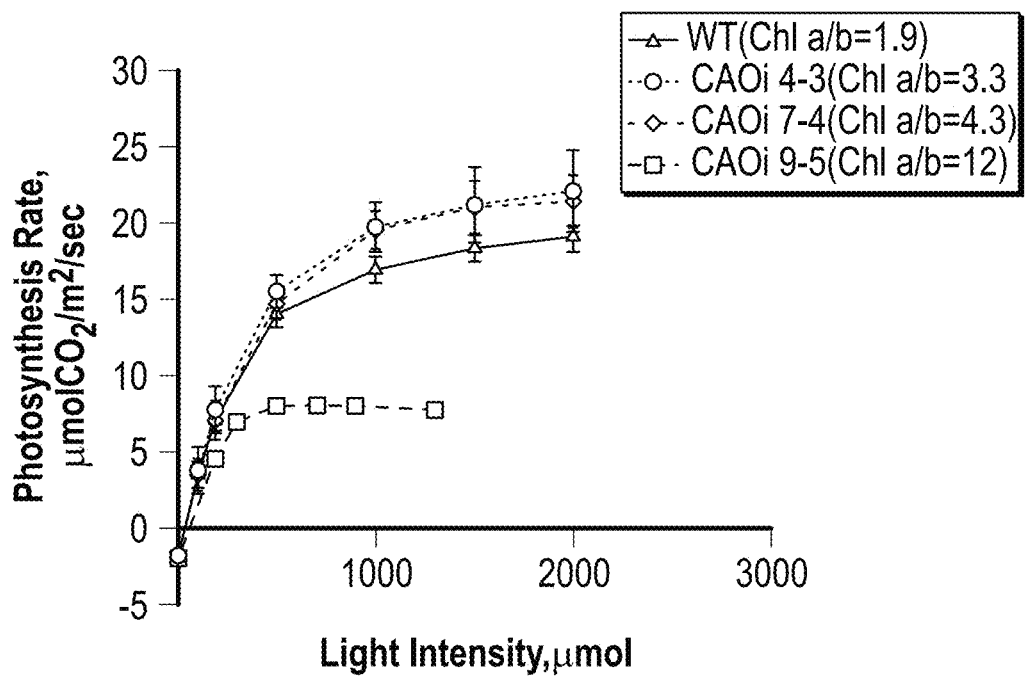
FIG. 5
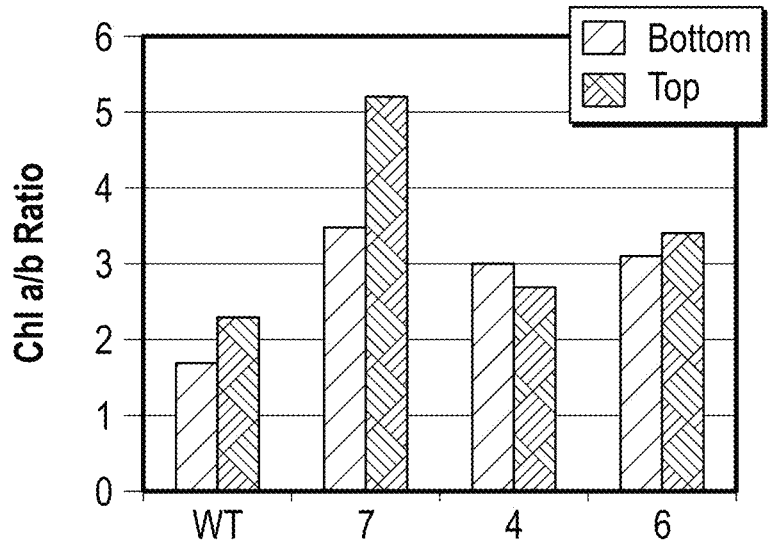
FIG. 6A
| Sample Leaf Position | Chl/Leaf Area (Normalized to WT) |
|---|---|
| Wild Type - Bottom | 0.65 (1X) |
| Wild Type - Top | 1.88 (1X) |
| CAOi 7 Bottom | 0.67 (1X) |
| CAOi 7 Top | 0.74 (0.4X) |
FIG. 6B 1 Sec Light 10 Sec Light 1 Min Light 5 Min Light Chl a/b=6          Chl a/b=3

TRANSGENIC PLANTS WITH ENGINEERED REDOX SENSITIVE MODULATION OF PHOTOSYNTHETIC ANTENNA COMPLEX PIGMENTS AND METHODS FOR MAKING THE SAME

CROSS-REFERENCE TO RELATED APPLICATIONS

This application is a continuation of International Patent Application No. PCT/US2015/060448, entitled "Transgenic Plants with Engineered Redox Sensitive Modulation of Photosynthetic Antenna Complex Pigments and Methods for Making the Same", filed on Nov. 12, 2015, which claims priority to and the benefit of U.S. Provisional Patent Application No. 62/078,936, entitled "Engineered plants with intermediate size light-harvesting complex antenna complexes and method for same", filed on Nov. 12, 2014, and the specification and claims thereof are incorporated herein by reference.

STATEMENT REGARDING FEDERALLY SPONSORED RESEARCH OR DEVELOPMENT

This invention was made with government support under Grant Nos. EF-1219603 and DOE-CABS Prime No: DE-SC0001295, Sub No: 21017-NM awarded by the National Science Foundation and the Department of Energy, respectively. The government has certain rights in the invention.

INCORPORATION BY REFERENCE OF MATERIAL SUBMITTED ON A COMPACT DISC

NA.

COPYRIGHTED MATERIAL

NA.

BACKGROUND

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Photosynthetic plants utilize sunlight to power all cellular processes (directly or indirectly) and ultimately derive most or all of their biomass through chemical reactions driven by light. All commercially important photosynthetic plants belong to the kingdom Plantae. They include familiar organisms such as trees, herbs, bushes, grasses, vines, ferns, mosses, and the Chlorophytic green algae.

Plants obtain energy from sunlight via a process called photosynthesis. Photosynthesis is a process that converts carbon dioxide into organic compounds, especially sugars, using the energy from sunlight (Blankenship, 2010). Plants absorb sunlight via their photosynthetic antenna complexes, also called light harvesting complexes (LHC) and sometimes referred to herein as light harvesting antenna complexes, whose function it is to transfer excitation energy to the reaction center complexes of Photosystem II (PSII) and Photosystem I (PSI). The reaction centers then drive electron transfer, photophosphorylation and oxygenic reactions that lead to energy production and carbon capture in the form of complex biomolecules (e.g., sugar, starch, lipids, and the like).

Light harvesting antenna complexes for PSI (termed LHC I) and PSII (termed LHC II) are composed of pigment-protein complexes. Light harvesting antenna pigments including chlorophyll a (Chl a) and chlorophyll b (Chl b) and a variety of accessory pigments (e.g., carotenoids and xanthophylls) which participate in the complicated energy transfer route of photosynthesis. The PSII light harvesting complex includes the proximal (near) antenna Chl a binding proteins associated with the PSII reaction center; and the peripheral (distal) antenna Chl a, Chl b, and carotenoid binding proteins. The peripheral antenna complex of PSII (LHC II) further comprises the major (outer) more abundant trimeric antenna proteins that are encoded by nine genes (LHCBM 1-LHCBM9) and a core (inner) antenna protein complex that is encoded by three genes (LHCB4, LHCB5 and LHCB7) (Minagawa and Takahashi, 2004). LHC II proteins contain up to 80% of the total chlorophyll in plant and algal thylakoid membranes.

The process of photosynthesis has been optimized through evolution to produce plants adapted to be more fit in natural environments; it was not, however, necessarily optimized to give the highest harvest index in monoculture conditions relevant to agriculture. Here "harvest index" refers to the yield of the desired product compared to the total mass of the plant. Strategies involving reducing the optical cross-section of photosynthetic light-harvesting antenna size have been developed and successfully implemented in algal cultures, resulting in improved productivity. The instant invention describes a similar approach that can be also utilized in plants for improved productivity. Engineered plants with a range of chlorophyll a/b ratios, and, as a result, light harvesting antenna sizes can be produced. An optimal range of antenna sizes results in improved photosynthetic performance and the invention describes a sharp transition point where further reductions in antenna size becomes detrimental to photosynthetic efficiency. We hypothesize that this transition point is related to a phase transition in the arrangement of photosystem II in thylakoid membranes, regulated by the abundance of light harvesting complexes II. Plants with optimized antenna perform well not only in controlled greenhouse conditions, but also in the field. Embodiment of the present invention provides transgenic plants having improved yield of productivity, constructs and methods of use to produce said tranasgenic plants.

In nature, photosynthetic cells may adjust to altered light environments in order to optimize energy capture and conversion efficiency or, alternatively, to protect the cells from too much light. Cells adjusted to low light levels typically possess larger light harvesting antenna complexes than those acclimated to high light intensities so as to maximize light capture at limiting light conditions. Such low light acclimated plants have lower Chl a/b ratios as the photosystems contain relatively high amounts of Chl b and have a large light-harvesting complex (LHC) antenna (composed mostly of chlorophylls a and b). It has been reported plants that can adapt to high light intensity but the linkage to defined chl a/b ratios and improved yields has not been proven. Adapted plants that are grown under high light (HL) intensity, were shown to have relatively low amounts of Chl b in their LHC, smaller LHC antenna, and a higher Chl a/b ratio (Björkman et al., 1972; Leong and Anderson, 1984; Larsson et al., 1987). However, other studies have shown that photosynthetic cells acclimated to high light intensities have 50% lower cellular Chl contents but show only slight (if any) increases in the Chl a/b ratio (Neale and Melis, 1986).

A negative consequence of having efficient light harvesting complexes is that photosynthetic electron transfer in nearly all photosynthetic cells becomes light saturated at only 25% of full sunlight intensity (here full sun is assumed to be 2000 µmol photons m-2s-1 at 400-700 nm) (Polle et al., 2001). At high photosynthetic photon flux densities (photosynthetic photon flux density is a measure of the number of photons in the 400-700 nm range of the visible light spectrum that fall on a square meter of target area per second), the rate of photon absorption exceeds the rate at which photosynthesis can convert the energized antenna complexes into productive charge transfer processes (that are used to produce reducing equivalents and energy). Over excitation of the light harvesting antenna complex under high light intensities increases the potential for long-lived excited states and photo-oxidative damage in plants, this is due to the generation and accumulation of reactive oxygen species (ROS) such as chlorophyll in its triplet state (3Chl) and reactive oxygen species (Krieger-Liszkay et al., 2008, Vass and Cser, 2009).

Plants have short- and long-term responses to protect the photosynthetic apparatus from the harmful effects of excess light. Short-term responses include the thermal dissipation of excess absorbed photons (qE) and state transitions (qT), both of which are components of non-photochemical quenching (NPQ). The qE (energy-dependent quenching) processes involve the de-excitation of Chl in its singlet excited state (Chl*) formed in the PSII antenna upon light absorption to minimize the formation of triplet state chlorophyll (3Chl) and ROS in the photosynthetic apparatus (Muller et al., 2001). Processes associated with qT are involved in regulating the relative excitation of PSII and PSI and thereby regulate linear and cyclic electron flow during photosynthesis (Eberhard et al., 2008). Longer term responses occur over hours and days after high light exposure and include transcriptional and translation level changes in LHC mRNAs and high light induced mRNAs, PSII core protein (D 1) turnover and PSII repair, and increases in the xanthophyll cycle carotenoids. Hence, under high light intensities, up to 80% of absorbed photons can be dissipated as heat or fluorescence due to fluorescence and the activation of the short-term photoprotective responses (NPQ) causing large decreases in light utilization efficiency and photosynthetic productivities (Polle et al., 2002).

Chl b is synthesized from proto-Chl a by chlorophyll a oxygenase (CAO) which is sometimes referred to in the literature as chlorophyll b synthase. Either nomenclature applies to the instant invention. The overexpression of the Cao gene leads to the enhancement of Chl b biosynthesis in *Arabidopsis* and consequently to an enlargement of the PSII-associated peripheral antenna (Tanaka et al., 2001). Significantly, Chl b-less mutants (cbs-3) of a green alga, *Chlamydomonas*, have substantially elevated light-saturated photosynthetic oxygen evolution rates (up to 1.25 fold increase when expressed on a Chl basis) compared to the wild-type and do not light saturate at full sunlight intensities (Polle et al., 2000). Moreover, studies where the size of the LHC II has been preferentially attenuated have shown that reducing PSII antenna size (and not PSI) results in higher rates of oxygen evolution at high light intensities than wild-type cells (Polle et al., 2002; Polle et al., 2001).

Embodiments of transgenic plants of the present invention are engineered to artificially modulate the light harvesting complexes. For example, the modulation of the LHC can occur in a tissue-specific manner that is, the expression of one or more genes is linked either to a light-activated promoter or is driven by a tissue-specific promoter that is only active in photosynthetic tissues of the plant. Unexpectedly, a transgenic plant as described according to one embodiment of the present invention provides for improved partition of a significant amount of the improved carbon fixation into storage tissues such as the seed or starch rather than a generalized increase in biomass of all tissues. Additionally, these transgenic plants have improved rates of growth, starch accumulation in plastids, and non-photochemical quenching (high light photoprotection) in comparison to wild-type plants grown under the same condition.

This and other unmet needs of the prior art are met by exemplary compositions and methods as described in more detail below.

BRIEF SUMMARY OF THE INVENTION

One embodiment of the present invention provides for a transgenic plant capable of modulating its photosynthetic antenna complex composition in response to increases or decreases in light intensity by modulation of the ratio of chlorophyll a to chlorophyll b such that there is an increase in the Chl a/b ratio at high light intensity and a decrease in the Chl a/b ratio at low light intensity versus wild-type plants grown in the same conditions. The transgenic plant's native chlorophyll a oxidase gene may be excised, disrupted or suppressed. For example, the native chlorophyll a oxidase gene is disrupted using a procedure chosen from CRISPR/Cas 9 mediated genome editing, TALEN-mediated gene disruption, chemical mutagenesis coupled with TILING, insertional mutagenesis coupled with PCR screening for insertion events in the native chlorophyll a oxidase gene, gene disruption by RNA interference (RNAi). In a preferred embodiment, the transgenic plant comprises a DNA construct comprising a heterologous expression control sequence operatively linked to a polynucleotide sequence encoding a chlorophyll a oxidase or fragment thereof. The expression control sequence may interact with a redox-sensitive modulator responsive to changes in ambient light intensity and the redox-sensitive modulator may be chosen from NAB1, GCD2, and GLD-1. The expression control sequences may comprise a cold-shock domain sequence motif and in a preferred embodiment, the cold shock domain sequence motif is chosen from CSDDCS and may be operatively linked to a promoter. The promoter may be chosen from the group consisting of psaD, actin, ubiquitin, β-tublin, PR-1a, and 35S or the promoter is a tissue-specific promoter such as CAB1 or RbcS. In a preferred embodiment, the polynucleotide sequence of the construct is a heterologous DNA sequence. The DNA construct may include a reverse compliment of the polynucleotide sequence encoding a fragment of chlorophyll a oxidase and the expression controlled sequence may be a tissue-specific promoter that is responsive to changes in ambient light intensity.

Another embodiment provides for a method to produce a transgenic plant with the ability to modulate its Chl a/b ratio of an antenna complex in response to ambient sunlight comprising the steps of stably transforming a plant with a heterologous polynucleotide sequence containing targeting sequences to a portion of an endogenous chlorophyll a oxidase gene wherein the heterologous polynucleotide sequence excises, disrupts or suppresses expression of the endogenous chlorophyll a oxidase gene in response to changes in ambient light intensity. A transformant is selected that is capable of modulating the antenna size in response to changes in light intensity.

In another method, a transgenic plant is produced with the ability to modulate its Chl a/b ratio of an antenna complex in response to ambient sunlight comprising the steps of producing a transgenic plant wherein an endogenous chlorophyll a oxidase gene has been disrupted. The transgenic plant is stably transformed with a heterologous polynucleotide sequence encoding for a modified chlorophyll a oxidase wherein expression of the modified chlorophyll a oxidase is controlled by changes in ambient light intensity. A transformant is selected that is capable of modulating the antenna size in response to changes in light intensity. In a preferred embodiment, the heterologous polynucleotide sequence comprises a promoter operatively linked to a cold-shock domain consensus sequence, for example the cold-shock domain sequence is chosen from the group consisting of: SEQ. ID. NO. 18-26. Additionally, the heterologous polynucleotide may comprise a promoter operatively linked to the modified chlorophyll a oxidase chosen from psaD, actin, ubiquitin, β-tublin, 35S, and PR1-a. In a preferred embodiment, the heterologous polynucleotide sequence comprises a tissue targeting sequence.

Another embodiment of the present invention provides for a DNA construct for producing a transgenic plant comprising a heterologous expression control sequence operatively linked to a polynucleotide sequence encoding a chlorophyll a oxidase or fragment thereof wherein expression of the polynucleotide sequence is controlled by changes in ambient light intensity. In a preferred embodiment, the heterologous expression control sequence is under the control of a redox-sensitive modulator which is responsive to changes in ambient light intensity. For example, the heterologous expression control sequence comprises a promoter that is operatively linked to a cold-shock domain consensus sequence and preferably the cold-shock domain sequence is chosen from the group consisting of: SEQ. ID NO. 18-26. In a preferred embodiment the promoter is chosen from psaD, actin, ubiquitin, β-tublin, 35S, and PR1-a and/or the redox-sensitive modulator is chosen from NAB1, GCD2, and GLD-1. In a preferred embodiment, the heterologous expression control sequence is a promoter responsive to changes in ambient light intensity and the polynucleotide sequence encodes for a portion of a chlorophyll a oxidase and a reverse compliment thereof. For example, the chlorophyll a oxidase or a fragment thereof for which the polynucleotide sequence encodes is selected from the group consisting of SEQ ID NO 1-5. Alternatively, the polynucleotide encodes a polypeptide having chlorophyll a oxidase activity or a polypeptide that is shorter than the polypeptide having chlorophyll a oxidase activity but has substantial sequence homology to the native gene for that portion of the polynucleotide expressed.

The transgenic plant may be selected from the group consisting of millet, corn (maize), sorghum, barley, oats, rice, rye, teff, triticale, wheat, rice, wild rice, amaranth, beans, lentils, fava, lupin, peanuts, chickpeas, pigeon peas, soybeans, mustards, rape seed (canola), safflower, sunflower, flax, jatropha, hemp, *Arabidopsis, Camelina*, poppy, trees (poplar, willow, *eucalyptus*, southern beech, sycamore, ash), *Miscanthus*, hemp, switchgrass, reed, canary grass, rye, giant reed, beets, sweet sorghum, sugar cane, potatoes, sweet potatoes, cassava, olives, soybean, rapeseed, and corn and preferably is *Camelina*. In a preferred embodiment, the Chl a/b ratio at high light levels in the transgenic plants is around 10% greater than that seen in wild-type plants. For example, the Chl a/b ratio is between 4 and 8 under high light intensity and preferably the Chl a/b ratio is between 5 and 8 under high light intensity. Preferably there is greater than around 10% increase in accumulation of the transgenic plant carbon sink storage compounds over the wild-type plant, for example, the transgenic plant storage compounds are chosen from lipid, starch, sugar, waxes, pigments and oils. In a preferred embodiment, the transgenic plant grows at around 10% faster than the wild-type plant of the same strain.

One aspect of the present invention provides methods and compositions for producing transgenic plants capable of self-modulating the size of photosystem II (PSII) peripheral antenna complex by regulating the expression of the chlorophyll a oxygenase gene (Cao) in response to different light intensities and in a tissue-specific manner as compared to wildtype plants. Also provided are transgenic plants that also exhibit enhanced photosynthetic productivity, higher yields of plant storage compounds, higher rates of growth, and/or other enhanced traits, (as compared to wild-type plants of the same strain) and methods for their use.

One aspect of such an enhanced transgenic photosynthetic plant provides for improved production systems with higher flexibility in growth conditions and improved yields.

An embodiment of the present invention describes methods for generating transgenic plants capable of modulating their PSII peripheral antenna size as a function of light intensity, and exhibit enhanced photosynthetic productivity. Although wild-type algae have pre-existing mechanisms to modulate the expression and size of their LHC II antenna at the transcriptional and post-transcriptional level under varying light levels (Durnford et al., 2003) the range of PSII antenna adjustment in wild-type plants is limited and cannot be similarly controlled to provide the advantages provided by the current invention.

One embodiment of the present invention takes advantage of a recently described light regulated and redox-sensitive, trans-acting protein factor called nucleic acid binding protein 1 ("NAB 1") that binds to LHC II mRNAs, negatively regulating their translation leading to a reduction of LHC II content under high light growth conditions in *Chlamydomonas reinhardtii* (Mussgnug et al., 2005). NAB1 binds to a cold-shock domain consensus sequence (CSDCS) motif found in several LHC II mRNAs (for example LHCM B6), sequestrating them into translationally silent messenger ribonucleoprotein complexes. By inserting the CSDCS element of the LHCM B6 mRNA into the promoter region used to control the expression of the Cao gene, transgenic organisms of the instant invention modulate the expression of the Cao gene in a light dependent manner. At high light intensity the NAB 1 protein binds to its respective mRNA binding site on the engineered Cao transcript, repressing its translation and the synthesis of Chl b, resulting in a reduced PSII peripheral antenna size. Conversely, under lower light intensities translational repression by NAB 1 is reduced due to lower NAB 1 expression levels allowing for increased levels of Cao gene translation and Chl b synthesis leading to the assembly of wild-type levels of the peripheral PSII antenna and in increased light capture at lower light intensities.

Embodiments of transgenic plants of the present invention are engineered to modulate LHC abundance in a tissue-specific manner that is, the expression of genes is linked either to a light-activated promoter or is driven by a tissue-specific promoter that is only active in photosynthetic tissues of the plant.

These transgenic plants are capable of modulating their PSII peripheral antenna size as a function of light intensity, and exhibit enhanced photosynthetic productivity compared to wild-type plants. Such enhanced photosynthetic plants provide for improved production systems with higher flexibility in growth conditions and improved yields. Unexpectedly, these plants partition much of the improved carbon fixation into storage tissues such as the seed or starch rather than a generalized increase in biomass of all tissues. Additionally, these plants have improved rates of growth, starch accumulation in plastids, and non-photochemical quenching (high light photoprotection) in comparison to wild-type plants grown under the same condition.

This and other unmet needs of the prior art are met by exemplary compositions and methods as described in more detail below. Exemplary embodiments of the compositions, systems, and methods disclosed herein provide enhanced yields of plants and or carbon sink within the plant(s). In a further embodiment the enhanced yields of the modified plants are not reflected in a generalized increase in all tissues but rather an increase in storage tissues for such generalized storage compounds such as but not limited to polysaccharides, proteins and lipids. In general compounds that store carbon for later use in metabolic processes are considered carbon sinks and will be referred to as such in this application.

In yet a further embodiment the enhanced yields are accompanied by an increased overall growth rate of the engineered plants relative to wild-type plants grown under identical conditions.

In one aspect, embodiments of the present invention provide novel elements for engineering plants to contain intermediate size (Chl a/b ratios between 3 and 6) self-adjusting light-harvesting antenna complexes in a tissue-specific manner.

Another embodiment of the present invention provides a novel step to generate chlorophyll a oxygenase gene (Cao) knockouts in plants using one of several strategies including but not limited to: clustered regularly interspaced short palindromic repeats coupled with the Cas 9 nuclease (CRISPR/Cas9) mediated gene disruption (Cong et al., 2013, Zhang, 2014), transcription activator-like effector nuclease (TALEN)-mediated gene disruption (Gaj et al., 2013), chemical mutagenesis coupled with targeting induced local lesions in genomes (TILING) (Coman et al., 2013, Leviatan et al., 2013), and insertional mutagenesis coupled with PCR screening for insertion event in the Cao gene.

In a further embodiment Cao gene knockout plants (where the endogenous Cao gene has been deleted or rendered non-functional) are modified with the introduction of 5' modified Cao gene into Cao knockout plant background using Ti Plasmid-mediated transformation. The introduced Cao gene has been modified to include either 3' or 5' nucleotide translation inhibitor binding domains that interact with specific trans-acting, translational repressor proteins from various sources such as: NAB1 (algae), the GCD2 (yeast; *Saccharomyces cerevisiae*) (Foiani et al., 1991), GLD-1 from mouse S4 in *Escherichia coli* (Jinks-Robertson and Nomura, 1982), STAR proteins (Saccomanno et al., 1999) and bacteriophage RB69 RegA (Jozwik and Miller, 1995) and other trans-acting repressors.

In yet a further embodiment, the expression of the translational repressor/inhibitor protein is controlled by a leaf-specific and light-induced gene promoter such as CAB1, rbcS, Dof 1, PPDK, and the like (Yanagisawa and Sheen, 1998, Matsuoka et al., 1993, Chattopadhyay et al., 1998). So that CAO protein is suppressed in high light but active in low light. The net result is higher Chl a/b ratios in high light intensity (upper canopy) and lower Chl a/b ratios in low light intensity (lower canopy) as compared to wild type.

In another embodiment, the plant's endogenous Cao is either modified, disrupted or repressed.

In another embodiment, siRNA technology is used to regulate expression of the Cao gene to modulate the Chl a/b ratios and antenna size in plants. The siRNA construct(s) targeting the Cao gene (CAOi) is introduced into plants using *Agrobacterium* Ti-plasmid. Expression of Cao siRNA constructs is controlled by a leaf-specific and light induced gene promoter which can be but is not limited to CAB1, rbcS, Dof 1, PPDK, and the like (Yanagisawa and Sheen, 1998, Matsuoka et al., 1993, Chattopadhyay et al., 1998).

In another embodiment, plants of the instant experiment have a Chl a/b ratio of about 5 and exhibit higher areal rates of photosynthesis than plants having any other Chl a/b ratio.

In yet another embodiment, plants with Chl a/b ratios of about 5 also have the higher levels of non-photochemical quenching (NPQ) than wild-type plants.

In yet another embodiment, plants with Chl a/b ratios of about 5 have higher starch or storage compound accumulation than wild-type.

In yet another embodiment, plants with intermediate antenna sizes (Chl a/b in the range of about 4 to 6) had reduced lower leaf drop and lower leaves persisted longer than those in mature wild-type plants.

In another embodiment, siRNA constructs targeting the Cao gene (CAOi) have Chl a/b ratios about 5 and grow faster than wild-type plants under the same conditions.

In a further embodiment, plants having siRNA elements targeting the Cao gene have higher seed count than wild-type plants and enhanced per plant seed mass to at least about 15% higher to, preferably, about double that of the wild-type plant.

In another aspect, the transgenic plant comprises a DNA construct comprising heterologous expression control sequence that is capable of binding to a redox-sensitive modulator that is responsive to ambient light intensity. In one aspect, a redox-sensitive repressor is more active at low light intensity, than at high light intensity.

In another aspect, the redox-sensitive modulator is NAB 1. In another aspect, the expression control sequences comprise a cold-shock domain consensus sequence (CSDDCS) motif. In yet another aspect, the expression control sequences further comprise a promoter operatively linked to the cold-shock domain consensus sequence. In one aspect, the promoter is selected from the group consisting of psaD, actin, ubiquitin, and β-tubulin.

In one aspect, the expression control sequences are operatively coupled to a polynucleotide sequence encoding the CAO protein. In one aspect, the polynucleotide sequence encoding the CAO protein is a heterologous nucleic acid sequence.

In another aspect, the transgenic plant comprises a heterologous redox-sensitive modulator. In one aspect, the heterologous redox-sensitive modulator is NAB 1. In another aspect, the transgenic plant exhibits an increase in biomass production compared to wild-type plants grown under identical conditions.

In another embodiment, a method of producing an improved plant, comprising the steps of stably transforming a plant with a heterologous polynucleotide sequence comprising expression control sequences comprising a cold-shock domain consensus sequence (CSDDCS) motif, that is capable of binding to a redox-sensitive modulator that is responsive to ambient light intensity; selecting a transformant that is capable of modulating PSII antenna size in response to ambient light intensity is provided.

In one aspect, the heterologous polynucleotide sequences comprise targeting sequences specific for the plant's endogenous Cao gene.

In one aspect, the plant's endogenous chlorophyll a oxidase gene (Cao) has been modified, disrupted or suppressed.

In one aspect, the expression control sequences further comprise a promoter operatively linked to the cold-shock domain consensus sequence. In one aspect, the promoter is selected from the group consisting of psaD, actin, ubiquitin, and β-tubulin.

In one aspect, the expression control sequences are operatively coupled to a polynucleotide sequence encoding the CAO protein.

In one aspect, the selection is based on screening transgenic organisms that exhibit an increase in Chl a/b ratios when grown under high light intensity conditions, and a decrease in Chl a/b ratios when grown under low light intensity conditions.

In one aspect, the selection is based on screening the transgenic plants that exhibit an increase in biomass production compared to wild-type organisms grown under identical conditions.

In one aspect, the plant comprises a heterologous redox-sensitive modulator.

In one aspect, the heterologous redox-sensitive modulator is NAB 1.

In another embodiment, the invention includes a method of enhancing yields of photosynthetic productivity under conditions of high light intensity, and or high density growth, the method comprising providing a plant comprising a heterologous polynucleotide sequence comprising expression control sequences comprising a cold-shock domain consensus sequence (CSDDCS) motif operatively coupled to a polynucleotide sequence encoding the CAO protein; wherein expression of the Cao is increased at low light intensity, compared to the expression of the Cao at high light intensity; cultivating the transgenic plant at high light intensity and I or high density.

In another embodiment, the invention includes a method of enhancing bio-oil, or bio-diesel production from a plant the method comprising providing plant comprising a heterologous polynucleotide sequence comprising expression control sequences comprising a cold-shock domain consensus sequence (CSDDCS) motif operatively coupled to a polynucleotide sequence encoding the CAO protein, wherein expression of the Cao gene is increased at low light intensity, compared to the expression of the Cao gene at high light intensity; and cultivating the plant at high light intensity and I or high density.

In another embodiment, the invention includes a method of enhancing β-carotene, lutein, or zeaxanthin production from a plant, the method comprising; providing plant comprising a heterologous polynucleotide sequence comprising expression control sequences comprising a cold-shock domain consensus sequence (CSDDCS) motif operatively coupled to a polynucleotide sequence encoding the CAO protein, wherein expression of the Cao is increased at low light intensity, compared to the expression of the Cao at high light intensity; and cultivating the plant at high light intensity and I or high density.

In one aspect of any of these methods, the transgenic plant's endogenous chlorophyll a oxidase gene (Cao) has been modified, disrupted or suppressed.

In another aspect of any of these methods, the expression control sequences further comprise a promoter operatively linked to the cold-shock domain consensus sequence. In one aspect of this embodiment, the promoter is selected from the group consisting of psaD, actin, ubiquitin, and β-tubulin.

In another aspect of any of these methods, the polynucleotide sequence encoding the CAO protein is a heterologous nucleic acid sequence.

In another aspect of any of these methods, the plant comprises a heterologous redox-sensitive translational repressor. In one aspect of this embodiment, the heterologous redox-sensitive repressor is NAB 1.

In another embodiment, the current invention includes an expression vector comprising expression control sequences comprising a cold-shock domain consensus sequence (CSDDCS) motif operatively coupled to a polynucleotide sequence encoding the CAO protein.

In one aspect, the expression vector further comprises a promoter operatively linked to the cold-shock domain consensus sequence. In one aspect, the promoter is selected from the group consisting of psaD, actin, ubiquitin, and β-tubulin. In one aspect the expression vector comprises a CSDDCS motif is selected from the group consisting of SEQ ID. No. 18, SEQ ID. No. 19, SEQ ID. No. 20, SEQ ID. No. 21, SEQ ID. No. 22, SEQ ID. No. 23, SEQ ID. No. 24, SEQ ID. No. 25, and SEQ ID. No. 26.

In one aspect the expression vector comprises a Cao gene selected from the group consisting of SEQ ID. No. 1, SEQ ID. No. 2, SEQ ID. No. 3, SEQ ID. No. 4, and SEQ ID. No. 5.

Further scope of applicability of the present invention will be set forth in part in the detailed description to follow, taken in conjunction with the accompanying drawing, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. A better understanding of the features and advantages of the present invention exemplary embodiments of the invention will be had when reference is made to the accompanying drawings.

FIG. 5—Photosynthetic rates are compared under different light intensities in transgenic *Camelina* plants where siRNA technology was used to control expression the Cao gene at different rates. The abbreviation CAOi indicates that the chlorophyll a oxidase gene is under the control of an engineered siRNA effector.

FIG. 6A-B—Comparison of the Chl a/b ratio at different positions on the plant as well as the relative chlorophyll content per unit leaf area at different positions on the plant. The x axis of the bar chart on FIG. 6A shows three different CAOi mutants (CAOi 4, 6 & 7) and the wild-type plant. FIG. 6B illustrates the Ch./Leaf Area of different leaf positions compared to Wild Type (WT).

Physical parameters of the thylakoids in WT and mutant lines. (i) The thickness of thylakoid double membranes in WT and CR L-I, CR H-I, and CR V-H mutants, (j) The thickness of lumen in WT and CR mutants (k) Amount of thylakoids per granum in wild type and mutants. Average and maximum number of thylakoids per stack are shown (1) Amount of starch granules per section in chloroplasts of WT and CR L-I, CR H-I, and CR V-H mutants.

In Panel m is the blue native polyacrylamide electrophoresis (BN-PAGE) gel of PSII supercomplex formation as a function of Chl b abundance. Thylakoid membranes (8 μg of chlorophyll) isolated from wild type and CR L-I, CR H-I, and CR V-H lines were solubilized with final concentration of 1% (w/v) α-DM and subjected to BN-PAGE. Identities of the photosystem complexes are given on the left of the panel. The PSII supercomplexes are assigned as follows: SC1 (C2S or C2M), SC2 (C2S2 and C2SM), SC3 (C2S2M) and SC4 (C2S2M2).

Figure 19:
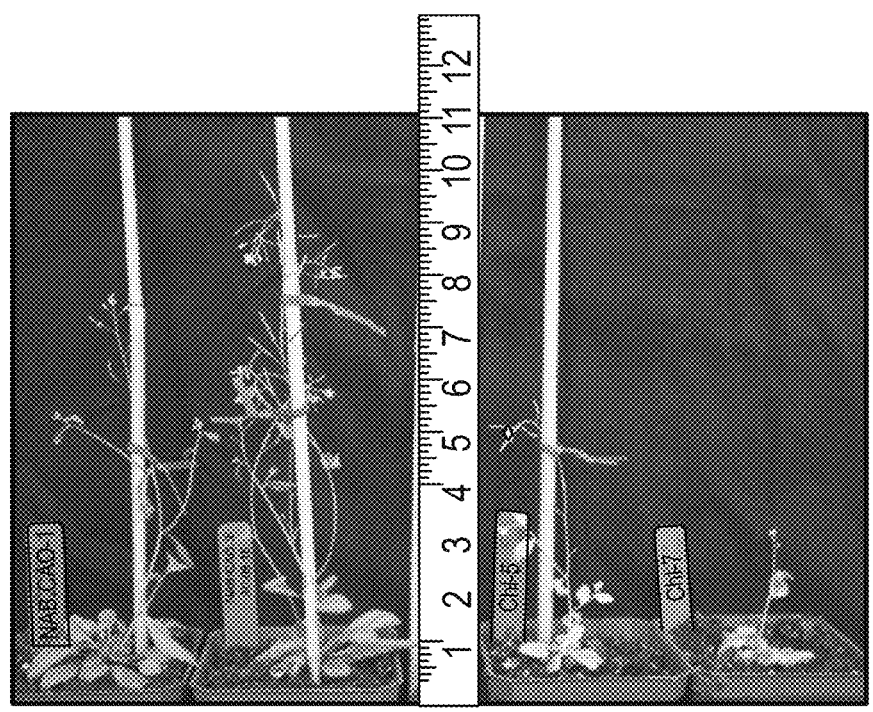

FIG. 19—Photograph of Arabidopsis NAB 1-CAO transgenic lines (labeled as NAB.CAO-1 & NAB.CAO-3) and the chlorophyll b minus (no chl b) Chlorina mutant lines (labeled Chl-5 & CHL-7). Transgenic NAB 1-CAO lines are Left of the ruler and Chlorina lines are Right of the ruler.

Figure 20:
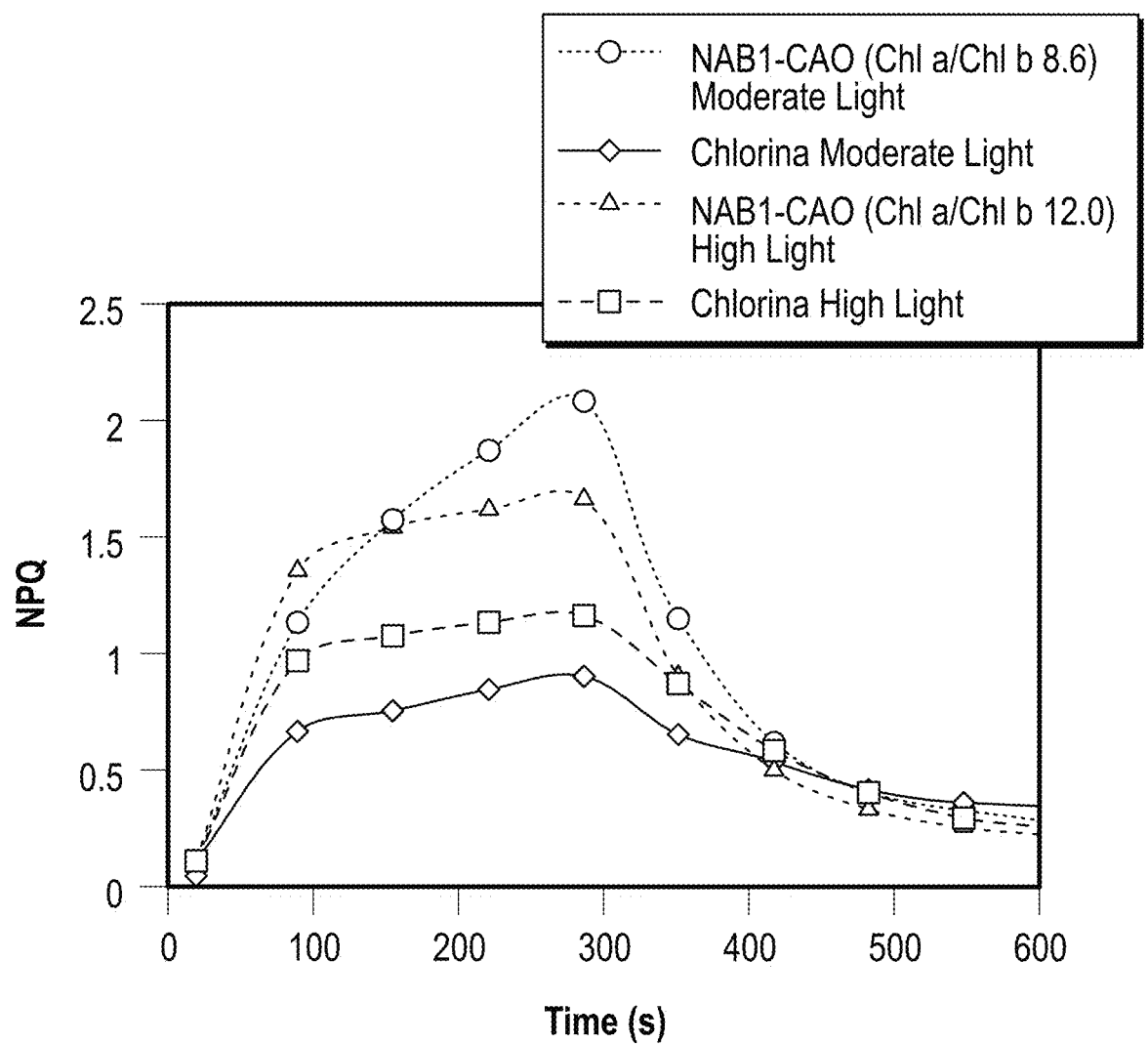

FIG. 20—Non-photochemical Quenching (NPQ) of Arabidopsis NAB1-CAO transgenics and Chlorina plants (4 week old) grown in moderate light intensity 150-180 μmoles, and high light (400 μmoles) treatment for 5 hours.

DETAILED DESCRIPTION OF THE INVENTION

Unless otherwise defined, all technical and scientific terms used herein have the same meaning as commonly understood by one of ordinary skill in the art to which this invention pertains. Although methods and materials similar or equivalent to those described herein can be used in the practice of the exemplary embodiments, suitable methods and materials are described below. All publications, patent applications, patents, and other references mentioned herein are incorporated by reference in their entirety. In case of conflict, the present specification, including definitions, will control. In addition, the materials, methods, and examples are for illustrative purposes only and not intended to be limiting.

As used herein, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges can independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The terms "about" or "approximately" means within an acceptable error range for the particular value as determined by one of ordinary skill in the art, which will depend in part on how the value is measured or determined, i.e., the limitations of the measurement system. For example, "about" can mean within 1 or 2 standard deviations, from the mean value. Alternatively, "about" can mean plus or minus a range of up to 20%, preferably up to 10%, more preferably up to 5%.

As used herein, the terms "cell," "cells," "host cell," and "host cells," are used interchangeably and, encompass any cells and preferably includes plant, and algal cells. All such designations include cell populations and progeny. Thus, the terms "transformants" and "transfectants" include the primary subject cell and cell lines derived therefrom without regard for the number of transfers.

As used herein a "control plant" means a plant that does not contain the recombinant DNA that expressed a protein or element that imparts an enhanced trait. A control plant is to identify and select a transgenic plant that has an enhanced trait. A suitable control plant can be a non-transgenic plant of the parental line used to generate a transgenic organism, i.e. devoid of recombinant DNA. A suitable control organism may in some cases be a progeny of a hemizygous transgenic plant that does not contain the recombinant DNA, known as a negative segregant.

The phrase "conservative amino acid substitution" or "conservative mutation" refers to the replacement of one amino acid by another amino acid with a common property to the replaced amino acid. A functional way to define common properties between individual amino acids is to analyze the normalized frequencies of amino acid changes between corresponding proteins of homologous organisms (Schulz and Schirmer, 1979). According to such analyses, groups of amino acids can be defined where amino acids within a group exchange preferentially with each other and therefore resemble each other most in their impact on the overall protein structure (Schulz and Schirmer, 1979).

Examples of amino acid groups defined in this manner include: a "charged polar group," consisting of glutamic acid (Glu), aspartic acid (Asp), asparagine (Asn), glutamine (Gln), lysine (Lys), arginine (Arg) and histidine (His); an "aromatic, or cyclic group," consisting of proline (Pro), phenylalanine (Phe), tyrosine (Tyr) and tryptophan (Trp); and an "aliphatic group" consisting of glycine (Gly), alanine (Ala), valine (Val), leucine (Leu), isoleucine (Ile), methionine (Met), serine (Ser), threonine (Thr) and cysteine (Cys).

Within each group, subgroups can also be identified, for example, the group of charged polar amino acids can be sub-divided into the sub-groups consisting of the "positively-charged sub-group," consisting of Lys, Arg and His; the negatively-charged sub-group," consisting of Glu and Asp, and the "polar sub-group" consisting of Asn and Gin. The aromatic or cyclic group can be sub-divided into the sub-groups consisting of the "nitrogen ring sub-group," consisting of Pro, His and Trp; and the "phenyl sub-group" consisting of Phe and Tyr. The aliphatic group can be sub-divided into the sub-groups consisting of the "large aliphatic non-polar sub-group," consisting of Val, Leu and Ile; the "aliphatic slightly-polar sub-group," consisting of Met, Ser, Thr and Cys; and the "small-residue sub-group," consisting of Gly and Ala.

Examples of conservative mutations include substitutions of amino acids within the sub-groups above, for example, Lys for Arg and vice versa such that a positive charge can be maintained; Glu for Asp and vice versa such that a negative charge can be maintained; Ser for Thr such that a free —OH can be maintained; and Gin for Asn such that a free —NH2 can be maintained.

The term "cold-shock domain consensus sequence (CSD-DCS) motif" or "CSDDCS motif" refers to a nucleic acid sequence that is substantially identical to any of SEQ. ID. NOs. 6 to 14. The CSDDCS refers to a group of nucleic acid sequences that serve as binding sites for proteins which display RNA-binding domains that can serve as transcription factors. These cold-shock domain sequences are found in a variety of seemingly unrelated proteins and all functionally control protein expression.

"Enhanced trait" or "enhanced phenotype" as used herein refers to a measurable improvement in a trait of plant including, but not limited to, yield increase, including increased yield under non-stress conditions and increased yield under environmental stress conditions. Many enhanced traits can affect "yield", including without limitation, number of cells in a liquid culture of a unicellular or multicellular plant, increased efficiencies of light utilization by a plant, amount of biomass production by a plant, amount of biofuel production by a plant, amount of select storage materials accumulated in a plant and amounts of compounds including but not limited to agar, alginate, carrageenan, starch, omega fatty acids, lipid, Coenzyme Q10, astaxanthin, and β-carotene. Nutraceutical, a term combining the words "nutrition" and "pharmaceutical", is a food or food product that provides health and medical benefits, including the prevention and treatment of disease. Such products may range from isolated nutrients, dietary supplements and specific diets to genetically engineered foods, herbal products, and processed foods such as cereals, soups, and beverages. Other enhanced traits include plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Other traits that can affect yield include, efficiency of germination (including germination in stressed conditions), growth rate (including growth rate in stressed conditions), ear number, seed number per year, seed size, composition of seed (starch, oil, protein) and characteristics of seed fill.

The term "expression" as used herein refers to transcription and/or translation of a nucleotide sequence within a cell. The level of expression of a desired product in a cell may be determined on the basis of either the amount of corresponding mRNA that is present in the cell, or the amount of the desired polypeptide encoded by the selected sequence. For example, mRNA transcribed from a selected sequence can be quantified by Northern blot hybridization, ribonuclease RNA protection, in situ hybridization to cellular RNA or by PCR. Proteins encoded by a selected sequence can be quantified by various methods including, but not limited to, e.g., ELISA, Western blotting, radioimmunoassay, immunoprecipitation, assaying for the biological activity of the protein, or by immunostaining of the protein followed by FACS analysis.

"Expression control sequences" are regulatory sequences of nucleic acids, and may comprise one or more of the following: promoters, leaders, enhancers, introns, recognition motifs for RNA, or DNA binding proteins, polyadenylation signals, terminators, internal ribosome entry sites (IRES) and the like, that have the ability to affect the transcription or translation of a coding sequence in a cell. Exemplary expression control sequences are described in Goeddel; Gene Expression Technology: Methods in Enzymology 185, Academic Press, San Diego, Calif. (1990).

A "gene" is a sequence of nucleotides which code for a functional "gene product". Generally, a gene product is a functional protein. However, a gene product can also be another type of molecule in a cell, such as RNA (e.g., a tRNA or an rRNA). A gene may also comprise regulatory (i.e., non-coding) sequences as well as coding sequences and introns. Exemplary regulatory sequences include promoters, enhancers and terminators. The transcribed region of the gene may also include untranslated regions including introns, a 5'-untranslated region (5'-UTR) and a 3'-untranslated region (3'-UTR).

The term "heterologous DNA" refers to DNA which has been introduced into a cell, or a nucleic acid molecule, that is derived from another source, or which is from the same source but is located in a different context such as multiple copies of a native gene being introduced in tandem or a promoter used to drive one gene in the wild-type driving a different or introduced gene.

The term "high light intensity" refers to a photon flux of about 500 µE m-2s-1 or more; conversely the term "low light intensity" refers to a photon flux of about 50 µE m-2s-1 or less.

The term "homology" describes a mathematically based comparison of sequence similarities which is used to identify genes or proteins having similar functions or motifs. The nucleic acid and protein sequences of the present invention can be used as a "query sequence" to perform a search against public databases to, for example, identify other family members, related sequences or homologs. Such searches can be performed using the NBLAST and XBLAST programs (version 2.0) of Altschul (Altschul et al., 1990). BLAST nucleotide searches can be performed with the NBLAST program, score=100, word length=12 to obtain nucleotide sequences homologous to nucleic acid molecules of the invention. BLAST protein searches can be performed with the XBLAST program, score=50, word length=3 to obtain amino acid sequences homologous to protein molecules of the invention. To obtain gapped alignments for comparison purposes, Gapped BLAST can be utilized as described in Altschul (Altschul et al., 1997). When utilizing BLAST and Gapped BLAST programs, the default parameters of the respective programs (e.g., XBLAST and BLAST) can be used.

The term "homologous" refers to the relationship between two proteins that possess a "common evolutionary origin", including proteins from superfamilies (e.g., the immunoglobulin superfamily) in the same species of animal, as well as homologous proteins from different species of animal (for example, myosin light chain polypeptide, and etc. (Reeck et al., 1987). Such proteins (and their encoding nucleic acids) have sequence homology, as reflected by their sequence similarity, whether in terms of percent identity or by the presence of specific residues or motifs and conserved positions.

As used herein, the term "increase" or the related terms "increased", "enhance" or "enhanced" refers to a statistically significant increase. For the avoidance of doubt, the terms generally refer to at least a 10% increase in a given parameter, and can encompass at least a 20% increase, 30% increase, 40% increase, 50% increase, 60% increase, 70% increase, 80% increase, 90% increase, 95% increase, 97% increase, 99% or even a greater than 100% increase over the control value.

The term "isolated," when used to describe a protein or nucleic acid, means that the material has been identified and separated and/or recovered from a component of its natural environment. Contaminant components of its natural environment are materials that would typically interfere with research, diagnostic or therapeutic uses for the protein or nucleic acid, and may include enzymes, hormones, and other proteinaceous or non-proteinaceous solutes. In some embodiments, the protein or nucleic acid will be purified to at least 95% homogeneity as assessed by SDS-PAGE under non-reducing or reducing conditions using Coomassie blue or, preferably, silver stain. Isolated protein includes protein in situ within recombinant cells, since at least one component of the protein of interest's natural environment will not be present. Ordinarily, however, isolated proteins and nucleic acids will be prepared by at least one purification step.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs.

Optimal alignment of sequences for comparison can be conducted, for example, by the local homology algorithm described in Smith & Waterman 1981, by the homology alignment algorithm described in Needleman & Wunsch 1970, by the search for similarity method described in Pearson & Lipman 1988, by computerized implementations of these algorithms (GAP, BESTFIT, PASTA, and TFASTA in the GCG Wisconsin Package, available from Accelrys, Inc., San Diego, Calif., United States of America), or by visual inspection. See generally references such as Altschul, S. F. et al., J. Molec. Biol. 215: 403-410 (1990) and Altschul et al. Nuc. Acids Res. 25: 3389-3402 (1997).

One example of an algorithm that is suitable for determining percent sequence identity and sequence similarity is the BLAST algorithm, which is described in (Altschul, S., et al., NCBI NLM NIH Bethesda, Md. 20894; & Altschul, S., et al., J. Mol. Biol. 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold.

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always; 0) and N (penalty score for mismatching residues; always; 0). For amino acid sequences, a scoring matrix is used to calculate the cumulative score. Extension of the word hits in each direction are halted when the −27 cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in one embodiment less than about 0.1, in another embodiment less than about 0.01, and in still another embodiment less than about 0.001.

The term "Oil" as used herein refers to any combination of lipid fractions of a biomass. "Lipid," "lipid fraction," or "lipid component" as used herein can include any hydrocarbon soluble in non-polar solvents and insoluble, or relatively insoluble, in water. The lipid fractions can include, but are not limited to, free fatty acids, waxes, sterols and sterol esters, triacylglycerides, diacylglycerides, monoacylglycerides, tocopherols, eicosanoids, glycoglycerolipids, glycosphingolipds, sphingolipids, and phospholipids. The lipid fractions can also comprise other lipid soluble materials such as chlorophyll and other algal pigments, including, for example, antioxidants such as but not limited to astaxanthin, zeaxanthin, and canthaxanthin.

The terms "operably linked" and "operatively linked," as used interchangeably herein, refer to the positioning of two or more nucleotide sequences or sequence elements in a manner that permits them to function in their intended manner. In some embodiments, a nucleic acid molecule according to the invention includes one or more DNA elements capable of opening chromatin and/or maintaining chromatin in an open state operably linked to a nucleotide sequence encoding a recombinant protein. In other embodiments, a nucleic acid molecule may additionally include one or more DNA or RNA nucleotide sequences chosen from: (a) a nucleotide sequence capable of increasing translation; (b) a nucleotide sequence capable of increasing secretion of the recombinant protein outside a cell; (c) a nucleotide sequence capable of increasing the mRNA stability, and (d) a nucleotide sequence capable of binding a trans-acting factor to modulate transcription or translation, where such nucleotide sequences are operatively linked to a nucleotide sequence encoding a recombinant protein. Generally, but not necessarily, the nucleotide sequences that are operably linked are contiguous and, where necessary, in reading frame. However, although an operably linked DNA element capable of opening chromatin and/or maintaining chromatin in an open state is generally located upstream of a nucleotide sequence encoding a recombinant protein; it is not necessarily contiguous with it. Operable linking of various nucleotide sequences is accomplished by recombinant methods well known in the art, e.g. using PCR methodology, by ligation at suitable restrictions sites or by annealing. Synthetic oligonucleotide linkers or adaptors can be used in accord with conventional practice if suitable restriction sites are not present.

The terms "polynucleotide," "nucleotide sequence" and "nucleic acid" are used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. A nucleic acid molecule can take many different forms, e.g., a gene or gene fragment, one or more exons, one or more intrans, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracil, other sugars and linking groups such as fluororibose and thioate, and nucleotide branches. As used herein, a polynucleotide includes not only naturally occurring bases such as A, T, U, C, and G, but also includes any of their analogs or modified forms of these bases, such as methylated nucleotides, inter-nucleotide modifications such as uncharged linkages and thioates, use of sugar analogs, and modified and/or alternative backbone structures, such as polyamides. A "promoter" is a DNA regulatory region capable of binding RNA polymerase in a cell and initiating transcription of a downstream (3' direction) coding sequence. As used herein, the promoter sequence is bounded at its 3' terminus by the transcription initiation site and extends upstream (5' direction) to include the minimum number of bases or elements necessary to initiate transcription at levels detectable above background. A transcription initiation site (conveniently defined by mapping with nuclease S1) can be found within a promoter sequence, as well as protein binding domains (consensus sequences) responsible for the binding of RNA polymerase. Prokaryotic promoters contain Shine-Dalgarno sequences in addition to the −10 and −35 consensus sequences.

A large number of promoters, including constitutive, inducible and repressible promoters, from a variety of different sources are well known in the art. Representative sources include for example, algal, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters active in plants include, for example nopaline synthase (nos) promoter and octopine synthase (ocs) promoters carried on tumor-inducing plasmids of *Agrobacterium tumefaciens* and the method wherein the tissue targeting sequence is chosen from sequences promoters such as the Cauliflower Mosaic Virus (CaMV) 19S or 35S promoter (U.S. Pat. No. 5,352,605), CaMV 35S promoter with a duplicated enhancer (U.S. Pat. Nos. 5,164,316; 5,196,525; 5,322,938; 5,359,142; and 5,424,200), and the Figwort Mosaic Virus (FMV) 35S promoter (U.S. Pat. No. 5,378,619). These promoters and numerous others have been used in the creation of constructs for transgene expression in plants or plant cells. Other useful promoters are described, for example, in U.S. Pat. Nos. 5,391,725; 5,428,147; 5,447,858; 5,608,144; 5,614,399; 5,633,441; 6,232,526; and 5,633,435, all of which are incorporated herein by reference. Additional useful light inducible promoters include but not limited to are: (1) PPCZm1 (phosphoenolpyruvate carboxylase from corn) Kausch et al. (2001) Plant Molecular Biology 45, 1-15; (2) RbcS (ribulose-bisphosphate carboxylase from rice) Nomura et al. (2000) The Plant Journal 22(3), 211-221 (3) Rca (Rubisco Activase from rice) Yang et al. (2012) Biochemical and Biophysical Research Communications 418, 565-570 (4) LHCP2 (light harvesting chlorophyll a/b binding-protein from rice) Tada et al. (1991), EMBO J. 10(7), 1803-1808 (5) cyFBPase (cytosolic fructose 1,6 biphosphatase from rice) Si et al., 2002, Acta Botanica Sinica. 44(11), 1339-1345. In a preferred embodiment the promoter will be a light-inducible promoter such as the promoter for rbcS, CAB1, Dofl, psbD, PPDK, PPCZm1, Rca, LHCP2, cyFBPase and the like.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell. Methods for purification are well-known in the art. As used herein, the term "substantially free" is used operationally, in the context of analytical testing of the material. Preferably, purified material substantially free of contaminants is at least 50% pure; more preferably, at least 75% pure, and more preferably still at least 95% pure. Purity can be evaluated by chromatography, gel electrophoresis, immunoassay, composition analysis, biological assay, and other methods known in the art. The term "substantially pure" indicates the highest degree of purity, which can be achieved using conventional purification techniques known in the art.

The term "sequence similarity" refers to the degree of identity or correspondence between nucleic acid or amino acid sequences that may or may not share a common evolutionary origin (see Reeck et al., supra). However, in common usage and in the instant application, the term "homologous", when modified with an adverb such as "highly", may refer to sequence similarity and may or may not relate to a common evolutionary origin.

In specific embodiments, two nucleic acid sequences are "substantially homologous" or "substantially similar" when at least about 85%, and more preferably at least about 90% or at least about 95% of the nucleotides match over a defined length of the nucleic acid sequences, as determined by a sequence comparison algorithm known such as BLAST, FASTA, DNA Strider, CLUSTAL, etc. An example of such a sequence is an allelic or species variant of the specific genes of the present invention. Sequences that are substantially homologous may also be identified by hybridization, e.g., in a Southern hybridization experiment under, e.g., stringent conditions as defined for that particular system.

The term "specific" is applicable to a situation in which one member of a specific binding pair will not show any significant binding to molecules other than its specific binding partner(s). The term is applicable to the situation where two complementary polynucleotide strands can anneal together, yet each single stranded polynucleotide exhibits little or no binding to other polynucleotide sequences under stringent hybridization conditions.

Similarly, in particular embodiments of the invention, two amino acid sequences are "substantially homologous" or "substantially similar" when greater than 90% of the amino acid residues are identical. Two sequences are functionally identical when greater than about 95% of the amino acid residues are similar. Preferably the similar or homologous polypeptide sequences are identified by alignment using, for example, the GCG (Genetics Computer Group, Version 7, Madison, Wis.) pileup program, or using any of the programs and algorithms described above. The program may use the local homology algorithm of Smith and Waterman with the default values: Gap creation penalty=−(1+1lk), k being the gap extension number, Average match=1, Average mismatch=−0.333.

The term "suppressed" in the context of "suppressed Cao expression" encompasses the absence of endogenous chlorophyll a oxygenase protein (CAO) in a plant cell, e.g., *Arabidopsis*, as well as protein expression that is present but reduced as compared to the level of CAO protein production in a wild-type plant. The term "suppressed" also encompasses an amount of CAO protein that is equivalent to wild-type levels, but where the protein has a reduced level of activity in comparison to wild-type plants. Generally, at least a 50% decrease in endogenous CAO activity, or expression, or the like is preferred, in other aspect, at least about 75%, or at least about 95%, or 100% (i.e. no endogenous activity) being particularly preferred. By convention and for clarity the abbreviation CAO (all caps) will refer to the protein and Cao (lower script, italics) will refer to the gene sequence unless otherwise indicated by the context of the sentence.

The term "knockout" or "knockout plant" refers to a plant where a specific gene has been directly rendered inoperable by genetically modifying the gene itself. This could be by a number of different methods such as insertion of nonsense sequence, insertion of stop codons, deletion of sequence within the gene to change the reading frame of the gene rending it inoperable. This differs in control of the gene by trans-acting engineering where one would control the gene's expression but not alter the gene directly to prevent its expression. Often genes that are controlled by trans-acting elements are called "knockdown plants" which is distinguished herein using the above definition as distinct from knockout plants.

As used herein, a "transgenic plant" is one whose genome has been altered by the incorporation of exogenous genetic material, e.g. by transformation as described herein. The term "transgenic plant" is used to refer to the plant produced from an original transformation event, or progeny from later generations or crosses of a transgenic plant so long as the progeny contains the exogenous genetic material in its genome. By "exogenous" is meant that a nucleic acid molecule, for example, a recombinant DNA, originates from outside the plant into which it is introduced. An exogenous nucleic acid molecule may comprise naturally or non-naturally occurring DNA, and may be derived from the same or a different plant species than that into which it is introduced.

The term "transformation" or "transfection" refers to the transfer of one or more nucleic acid molecules into a cell or organism. Methods of introducing nucleic acid molecules into cells include, for instance, calcium phosphate transfection, DEAE-dextran mediated transfection, microinjection, cationic lipid-mediated transfection, electroporation, scrape loading, ballistic introduction or infection with viruses or other infectious agents.

"Transformed", "transduced", or "transgenic", in the context of a cell or organism, refers to a cell or organism into which a recombinant or heterologous nucleic acid molecule (e.g., one or more DNA constructs or RNA, or siRNA counterparts) has been introduced. The nucleic acid molecule can be stably expressed (i.e. maintained in a functional form in the cell for longer than about three months) or non-stably maintained in a functional form in the cell for less than three months i.e. is transiently expressed. For example, "transformed," "transformant," and "transgenic" cells or organisms have been through the transformation process and contain foreign nucleic acid. The term "untransformed" refers to cells or organisms that have not been through the transformation process.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, chapters 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, —1990, In Situ Hybridization: Principles and Practice; Oxford University Press; M. J. Gait (Editor), 1984, Oligonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

The terms "chlorophyll a oxygenase sequence" "chlorophyll a oxygenase gene" or "Cao" refer to the gene sequence for enzymes capable of the synthesis of chlorophyll b via the oxidation of the methyl group on ring II of chlorophyll a. In the literature the chlorophyll a oxygenase has also been referred to as the chlorophyll b synthase and, as used in the current invention, any reference to chlorophyll b synthase is taken to equally refer to the chlorophyll a oxygenase. Representative species for various species of chlorophyll a oxygenase are provided in the sequence listing, and genes from other species may be readily identified by standard homology searching of publicly available or proprietary databases.

The terms "chlorophyll a oxygenase" or "CAO" refer to all naturally-occurring and synthetic forms of chlorophyll a oxygenase protein. In one aspect the chlorophyll a oxygenase is from a plant. In another aspect the chlorophyll a oxygenase is from algae.

Chlorophyll is a green pigment found in the chloroplasts of algae and plants as well as in the photosynthetic membranes of cyanobacteria and photosynthetic bacteria. It plays a critical role in the photosynthetic process by absorbing light and transferring light energy by resonance energy transfer to the reaction centers of the photosystems. Chlorophyll a (Chl a) is a form of chlorophyll that absorbs light energy from the violet-blue and orange-red portions of the electromagnetic spectrum with it red peak maximum at 659 nm. Chlorophyll b (Chl b) is another form of chlorophyll that also absorbs light energy from the violet-blue and orange-red portions of the electromagnetic spectrum with it red peak maximum at 642 nm. The slight shift in the absorbance maximum between Chl a and Chl b allows Chl b to easily pass energy to Chl a down the energy gradient (higher energy to lower energy) with high efficiency with the final destination of that energy being the reaction centers.

Accordingly the term "redox-sensitive modulators" refers to the group of proteins capable of mediating the reversible redox dependent regulation of gene transcription or translation. In one aspect such redox-sensitive modulators include proteins that include the conserved cold shock domain (Prosite motif PS00352; Bucher and Bairoch, (In) ISMB-94; Proceedings 2nd International Conference on Intelligent Systems for Molecular Biology, Altman R., Brutlag D., Karp P., Lathrop R., Searls D., ds., pp 53-61, AAAIPress, Menlo Park, 1994; Hofmann et al., Nucleic Acids Res. 27:215, 1999).

The term "NAB 1" as used herein includes all naturally-occurring and synthetic forms of NAB 1 that retain redox-sensitive modulator activity. Such NAB 1 proteins include the protein from *Chlamydomonas*, as well as peptides derived from other plant species and genera. In one aspect, "NAB 1" refers to the *Chlamydomonas* NAB 1 having the amino acid sequence SEQ. ID. NO. 6.

As used herein "wild-type plants" are of the same strain as the transgenic plants to which a comparison is made.

As used herein light responsive element (LRE) means the 13 bp long, sequence GCCAGACCCCCGC SEQ ID NO. 27 that is a binding site for NAB 1 for regulation/inhibition of translation of the downstream protein.

The publications discussed above are provided solely for their disclosure before the filing date of the present application. Nothing herein is to be construed as an admission that the invention is not entitled to antedate such disclosures by virtue of prior invention.

Figure 1:
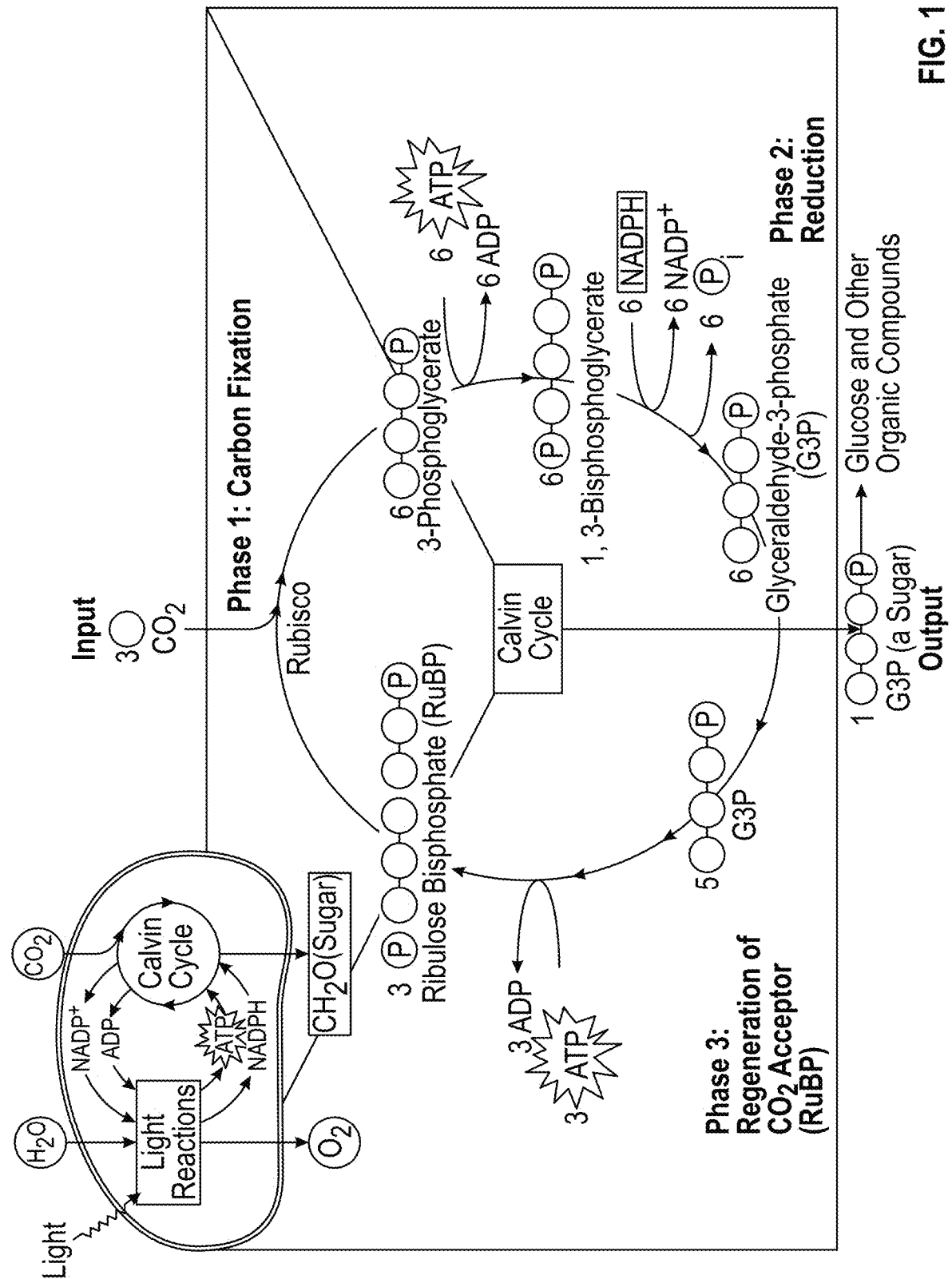
FIG. 1—Schematic of fixation of carbon during photosynthesis.

Referring now to FIG. 1, carbon as bicarbonate (HCO3) is transported through the cell membrane by a bicarbonate transporter (HLA3), through the chloroplast membrane as bicarbonate by another bicarbonate transporter (LCIA), it interacts with the electron transport apparatus of photosynthesis powered by the antenna complexes in the thylakoid stacks or grana (shown as stacks of plates in FIG. 1). The electron transport system produces energy and reducing equivalents that are used by the ribulose bisphosphate carboxylase/oxgenase (RuBisCo) to fix carbon as a useful substrate molecule. This is then fed to the rest of the cell to produce energy that runs plant metabolic processes.

Figure 2:
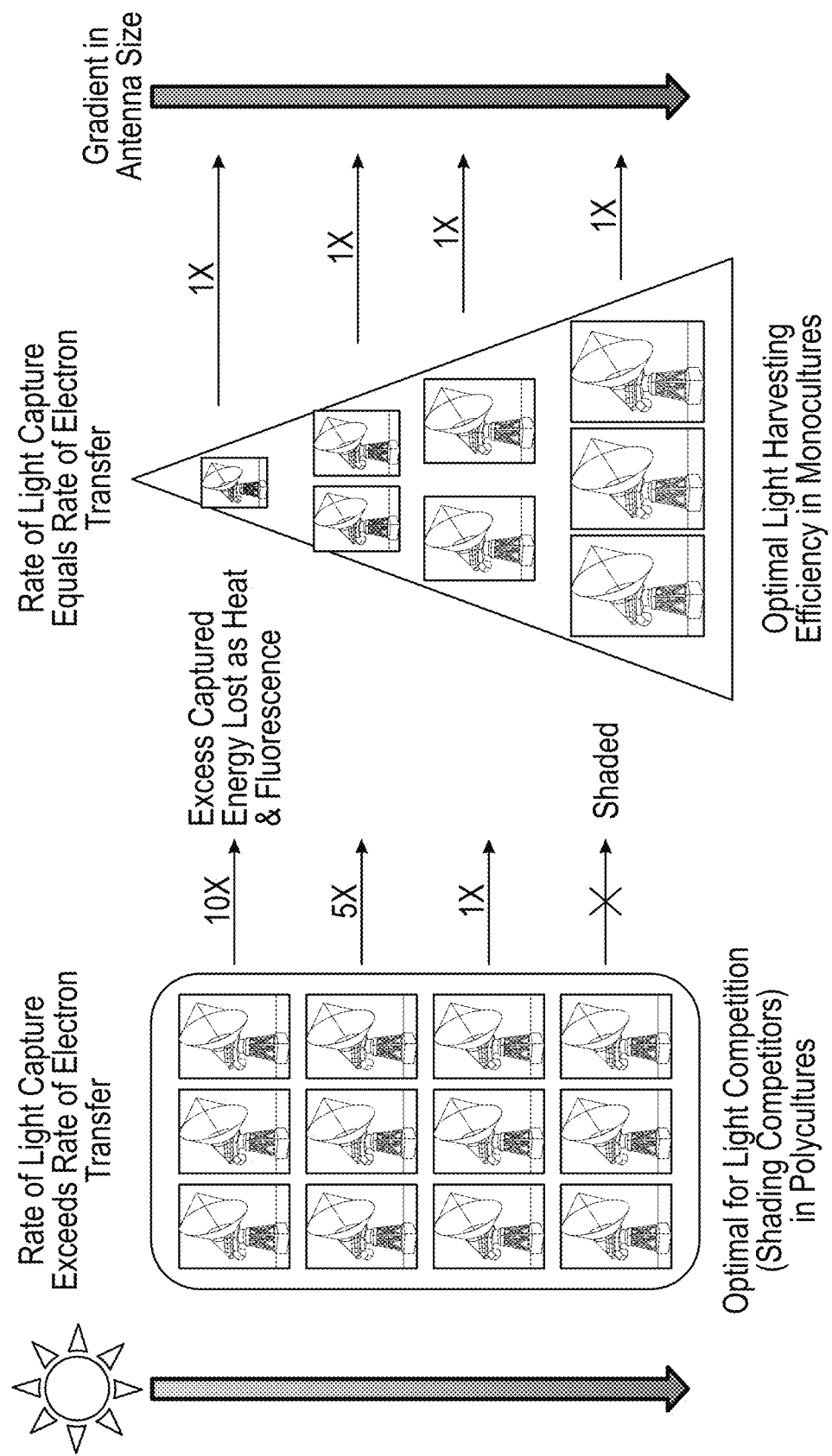
FIG. 2—Illustration explaining the underlying basis and utility of the invention on light capture and use.

Referring now to FIG. 2, wild-type plants have a full complement of the Chl a/b antenna complex that is capable of capturing more light energy than can be handled by the electron transfer system. This excess energy is dissipated as heat and reactive oxygen species (ROS; which have detrimental impacts on the plant through other processes such as photoinhibition). The full complement of the antenna complex is optimized to keep the plant functioning when shaded by competitors and is inefficient in handling full sunlight. Embodiments of the present invention provide a system where, during high sunlight or high light intensity, the antenna complex can be adjusted for optimal energy capture and linkage to the available electron transport system. As light is decreased more antenna complex is produced and the transgenic plant can continue to function optimally at this lower light and/or perform better than wild-type plants under the same growing conditions.

Figure 3:
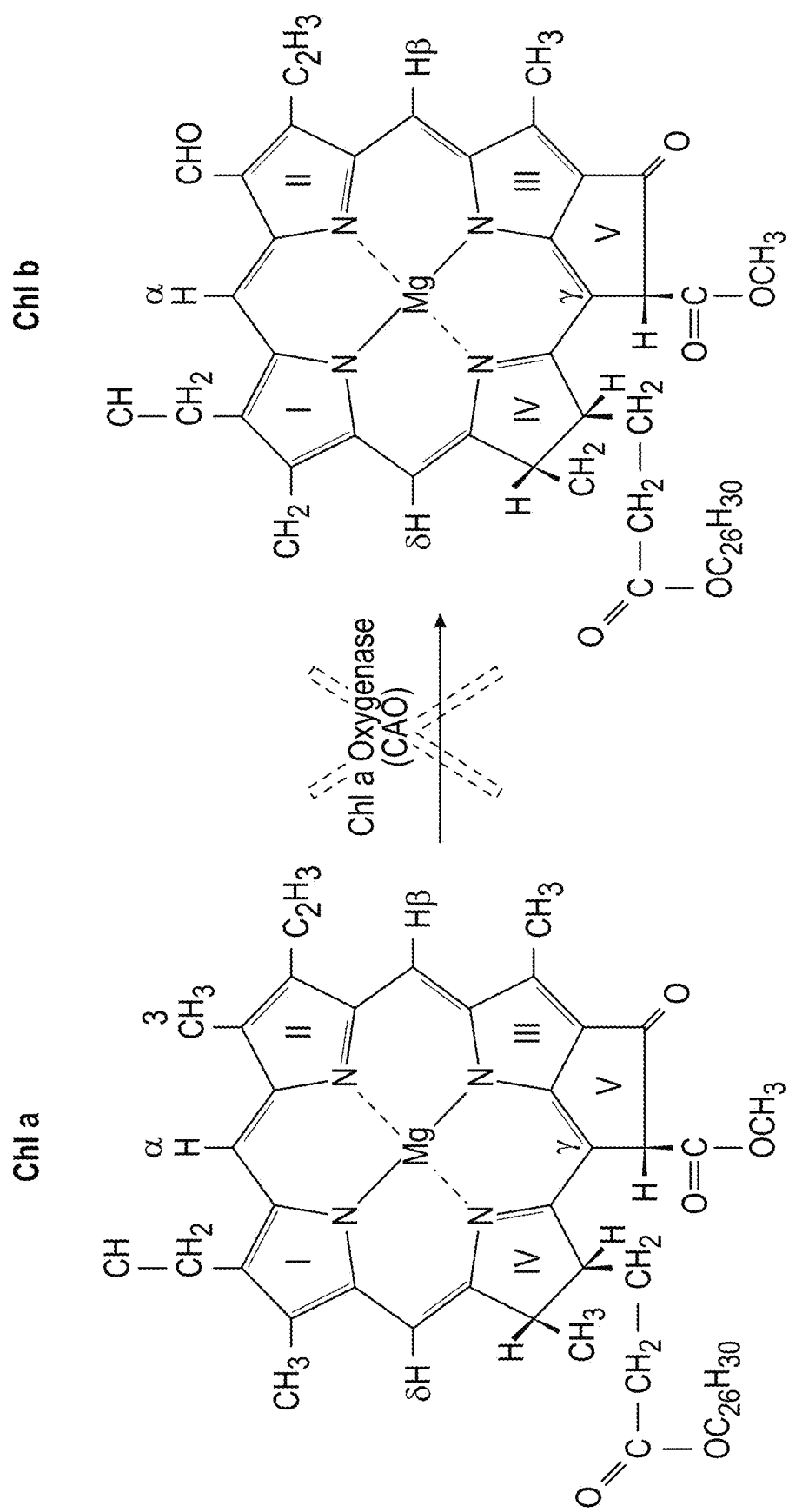
FIG. 3—Conversion of chlorophyll a (Chl a) to chlorophyll b (Chl b) is accomplished by the Chl a oxygenase enzyme (CAO). One embodiment of the current invention reduces or eliminates expression of this gene.

Referring now to FIG. 3, conversion of Chl a to Chl b is accomplished by the CAO enzyme which is encoded by the Cao gene. Control of the expression of the cao gene to allow high expression of the Cao gene under low light levels and reduced expression under high light levels allows self-adjustment of the size of the available antenna complex.

Figure 4A:
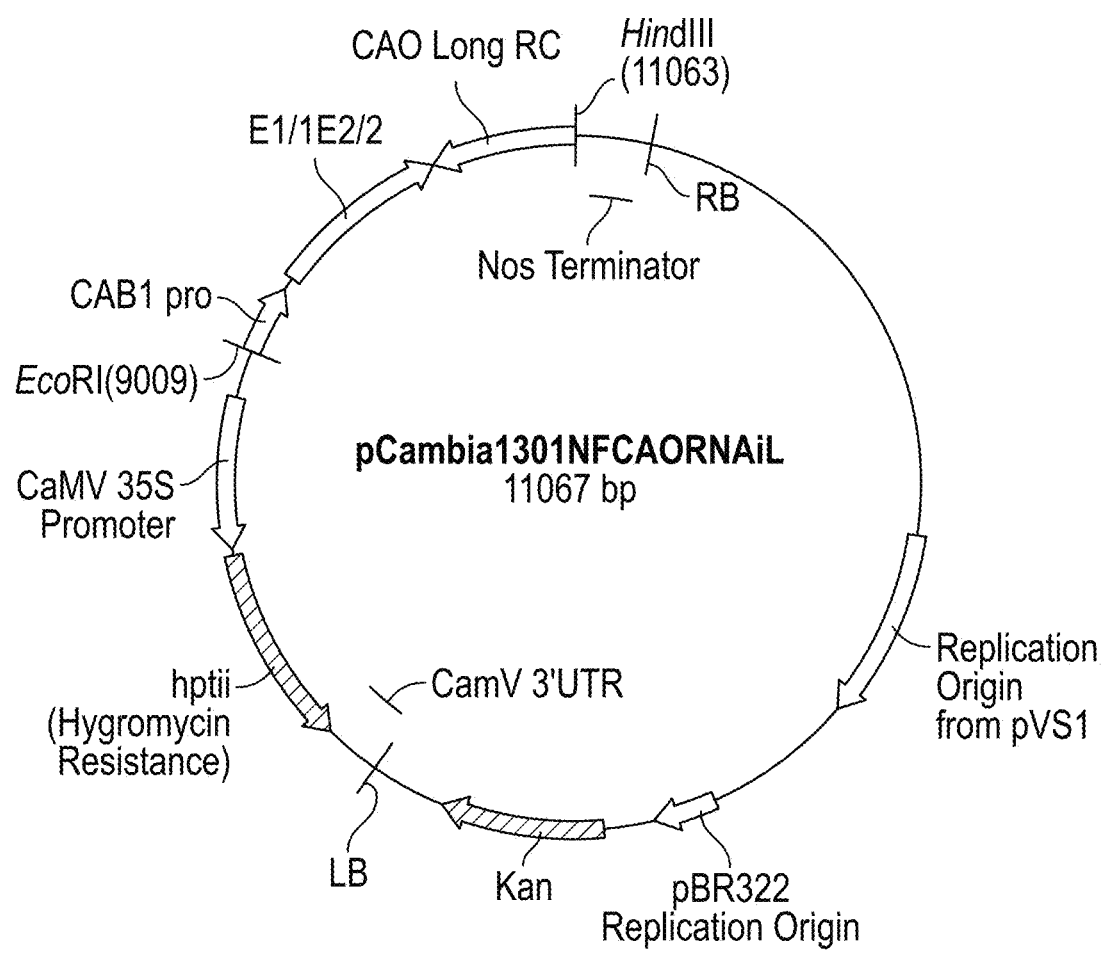
FIG. 4A-B—Two constructs useful for the *Agrobacterium* Ti plasmid-mediated transformation of *Camelina sativa* (*C. sativa*) according to one or more embodiments of the present invention.
Figure 4B:
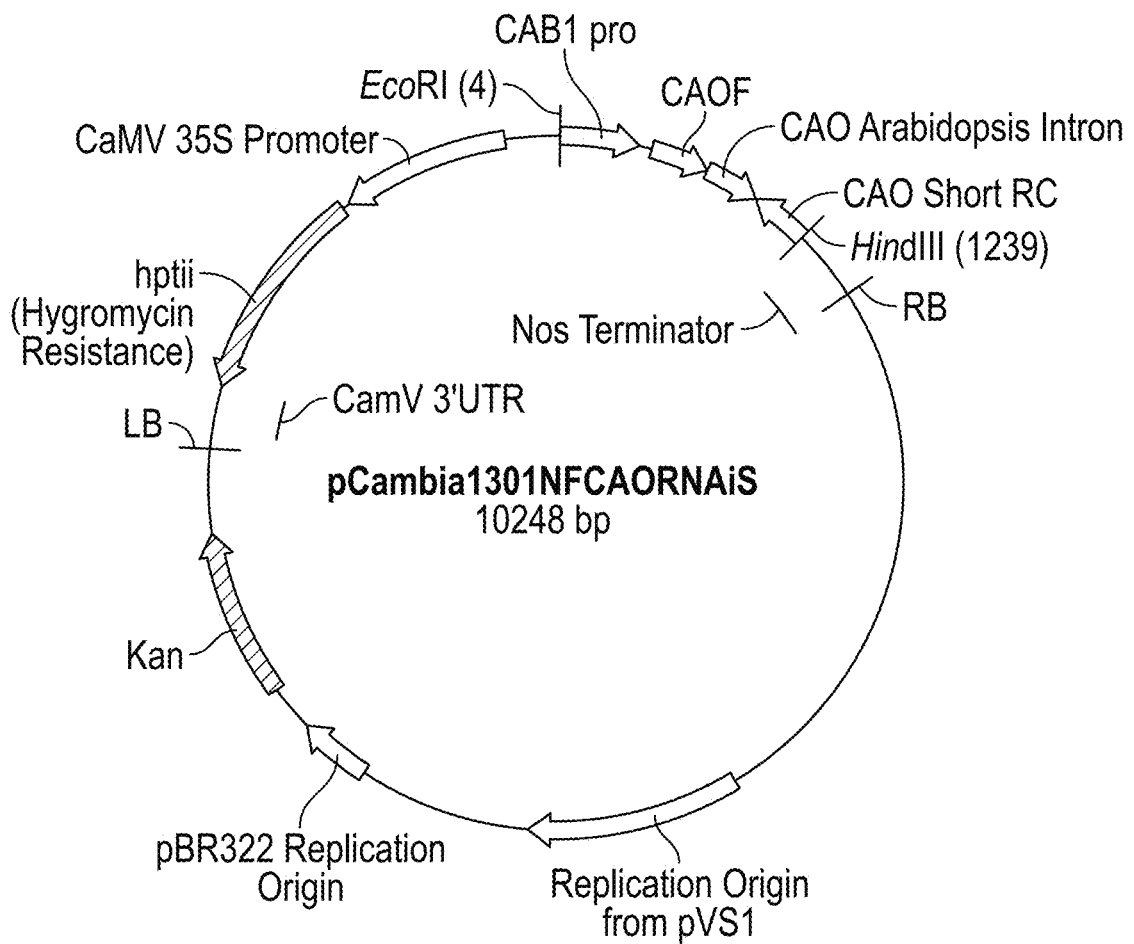

Referring now to FIG. 4A-B, constructs according to one embodiment of the present invention were based on the pCambia1301 vector and contained either a short (272 bp) or long (750 bp) section of the *Arabidopsis* Cao gene plus the reverse complement of these portions of the *Camelina* genome under the control of leaf-specific CAB1 promoter. In addition, the vectors contained bacterial kanamycin and plant hygromycin resistance genes and two *Arabidopsis* introns. Detailed description of these plasmids is provided in Example 3.

Referring now to FIG. 5, the photosynthetic rate was compared under different light intensities in transgenic *Camelina sativa* plants where siRNA technology was used to control expression of the Cao gene at different rates. These mutants were produced using the Suneson line using the pCambrai1301CAOiLong (FIG. 4A-B) using the floral dip method as described in Examples 4 and 5. This resulted in Cao gene knock down transgenic plants.

Through the methods described in the instant invention, the expression of Chl b was inhibited and the amount of antenna complex altered. This alteration was reflected in the ratio of Chl a to Chl b (Chl a/b ratio). The wild-type plants had a Chl a/b ratio of 1.9. Transgenic plants were made where this ratio varied from 3.3 to 12. It is obvious from these data that high Chl a/b ratios (e.g., 12) were not optimal for improved photosynthetic rate (e.g., CAOi 9-5). However, when the Chl a/b ratio was between 3.3 and 4.3, a significant improvement in the photosynthetic rate was observed compared to wild-type.

Referring now to FIG. 6A-B, comparison of the Chl a/b ratio at different positions on the plant as well as the relative chlorophyll content per unit leaf area at different positions on the plant is illustrated. Wild-type plants had lower Chl a/b ratios than three different CAOi mutants (referred to on the x-axis as 4, 6 and 7). All three of the CAOi transgenic plants where the Cao gene is regulated by light intensity all had significantly higher Chl a/b ratios than wild-type at the two locations within the plant measured (bottom and top). The regulation was most pronounced in CAOi 7 mutant where the shaded leaves (bottom) had a Chl a/b ration of about 3.4 while the full sun leaves had a Chl a/b ratio closer to 5.2. The bottom panel shows data from wild-type and CAOi 7 plants, the chlorophyll per unit leaf area was normalized to the WT plants. The chlorophyll per unit area of CAOi 7 leaves in the high light (top) was 40% of that found in the wild-type. However, the chlorophyll per unit area of the CAOi 7 and WT plants in the bottom leaves was virtually identical.

Figure 7:
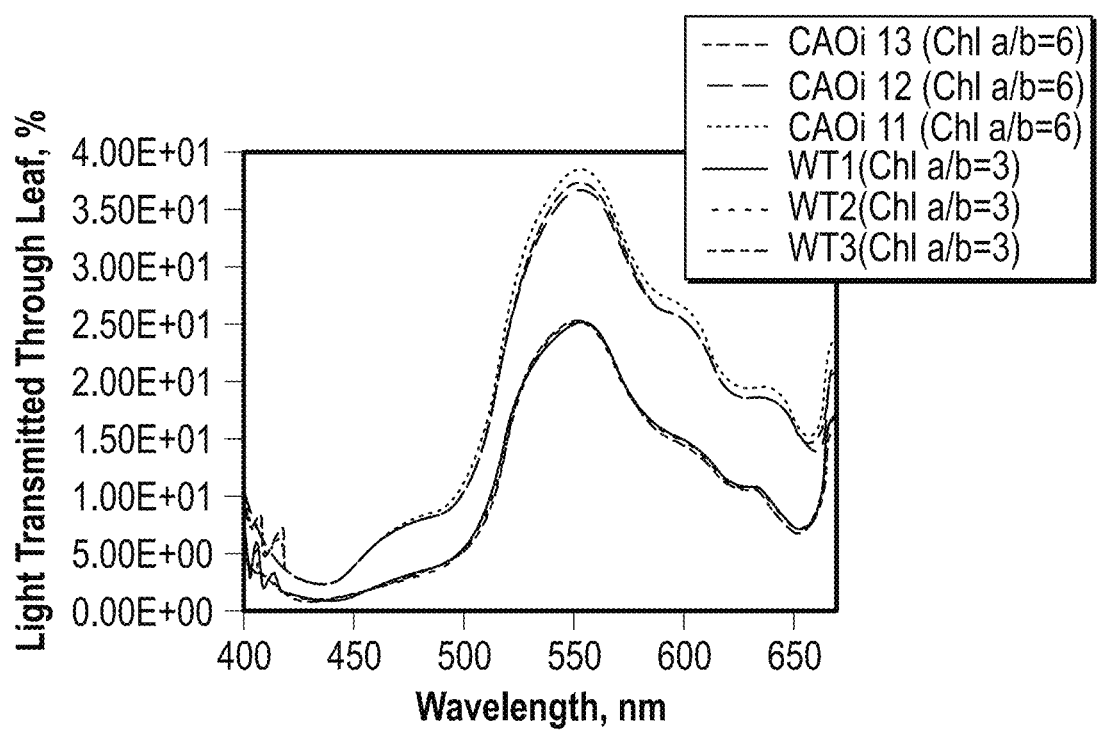
FIG. 7—Light transmittance through leaves of wild-type and chlorophyll a oxidase expression mutants generated using RNAi techniques (CAOi mutants). These provided chlorophyll a/b ratios of 6 while the wild-type plants tested had chlorophyll a/b ratios of 3.
Figure 8A:
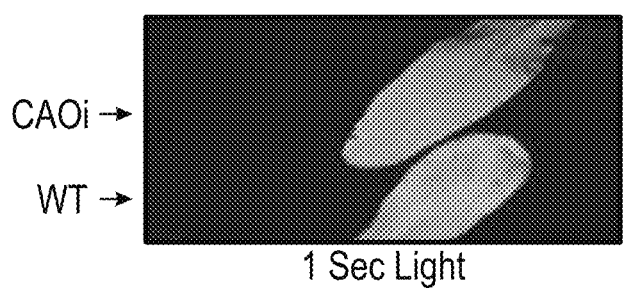
FIG. 8A-D—Comparison of the chlorophyll fluorescence of wild-type Camelina and a CAOi mutant. The original pictures were false color with blue, green, yellow and red used to indicate different levels of fluorescence. Blue represented no or low chlorophyll fluorescence, green low fluorescence, yellow increasing fluorescence and red high fluorescence. The CAOi mutant leaf in all the figures had an area of low fluorescence in the upper right portion of the leaf that appears as dark grey (blue in original picture). After 1 sec of light the CAOi mutant had low fluorescence (light grey/green) while the WT quickly showed increased fluorescence (light grey/yellow). After 10 seconds of light exposure, the CAOi mutant began to demonstrate increased fluorescence around its tip (light grey/yellow) while the WT was highly fluorescent (dark grey/red). On prolonged exposure to light (1 min and 5 min) the CAOi and WT reverted to a steady state where the CAOi mutant had low fluorescence (grey/green) and WT had increased fluorescence (light grey/yellow).
Figure 8B:
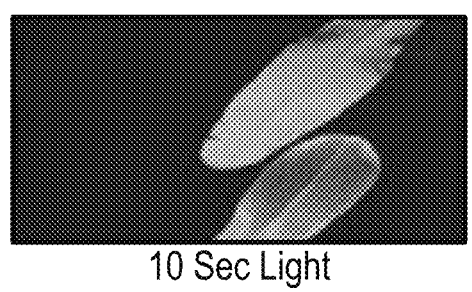
Figure 8C:
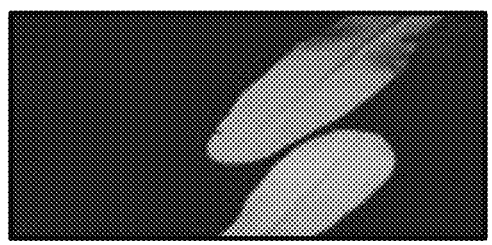
Figure 8D:
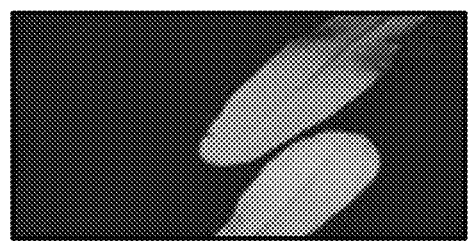

Referring now to FIG. 7, three wild-type *Camelina* plants that had chl a/b ratios of 3 had reduced transmittance of light through the leaf in comparison to three CAO siRNA (CAOi) mutants that had Chl a/b ratios of 6. Since the leaf thicknesses were very similar this increase in transmitted light by the CAOi mutants reflects the reduced antenna complexes relative to reaction centers in these CAOi mutants.

Referring now to FIG. 8A-D, comparison of the chlorophyll fluorescence of wild-type *Camelina* and a CAOi mutant. This picture is a black and white rendering of a colored photograph. Dark blue in the original is no fluorescence and was only observed in the top right corner of each CAOi mutant. Green is shown here as a medium gray and reflects mild fluorescence. Yellow is increased fluorescence and is a lighter grey. And red is shown as dark grey and represents highly fluorescent portions of the leaf. The darker portion of the CAOi mutant leaf is an artifact and not chlorophyll fluorescence. After 1 second exposure the WT leaf begins to show increased fluorescence (observed here as a lightening in the center and top half of the leaf). After 10 seconds, the CAOi mutant began to exhibit increase fluorescence at its tip (lightening in color) while the WT was highly fluorescent. On prolonged light exposure the CAOi mutants seemed to reach a steady low level of fluorescence while the WT settled to a moderate level of chlorophyll fluorescence. The CAOi mutant leaves demonstrated reduced chlorophyll fluorescence after prolonged exposure to light.

Figure 9:
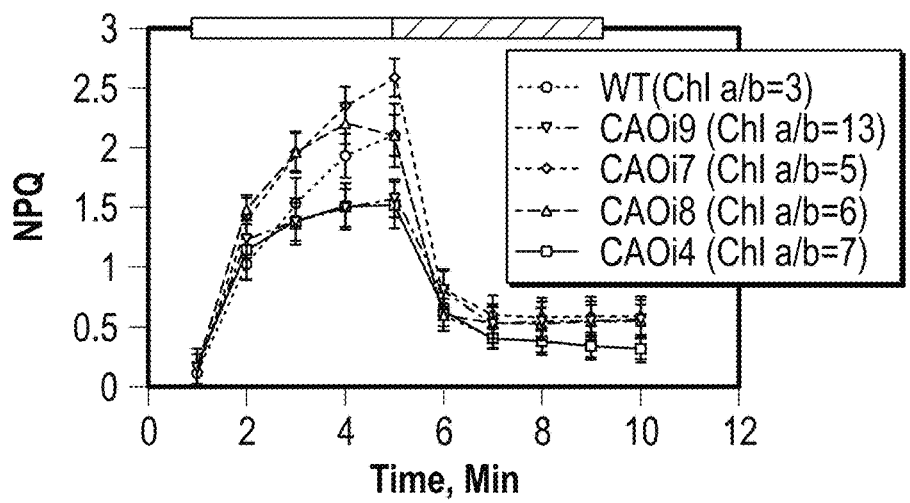
FIG. 9—Non-photochemical quenching (NPQ) over time for several different mutant CAOi lines compared to wild-type. The upper bar represents when the light was on (clear) or off (dark).

Referring now to FIG. 9, non-photochemical quenching (NPQ) over time for several different mutant CAOi lines compared to wild-type. Light was on from 0-5 min then plants were in the dark. Plants with Chl a/b ratios >7 showed reduced NPQ and reduced photoprotection. This reduction of NPQ at high Chl a/b ratios could explain why the photosynthetic rates decreased for the mutants with a Chl a/b ratio of 12 (FIG. 5).

Figure 10:
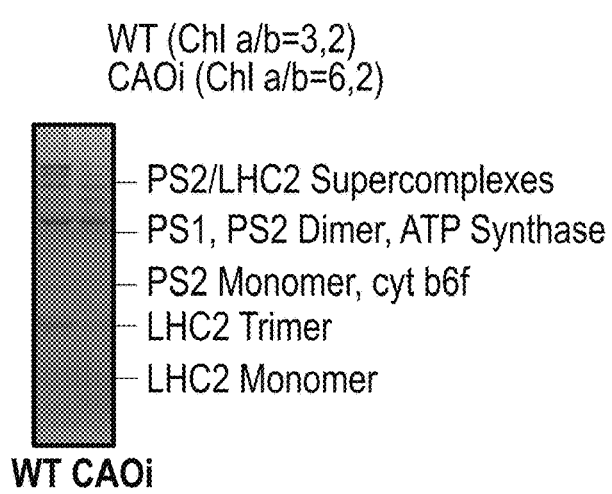
FIG. 10—Comparison of the proteins associated with the photosynthetic complexes of wild-type and CAOi mutant lines of Camelina.
Figure 11A:
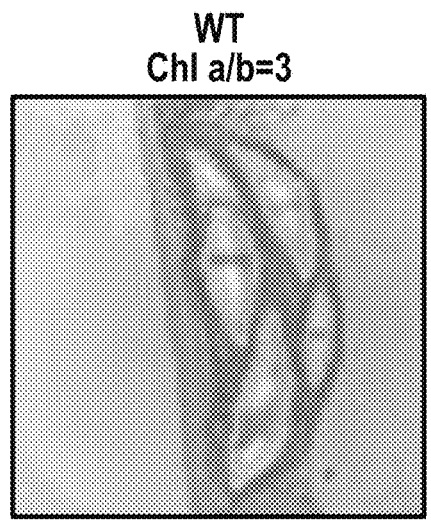
FIG. 11A-D—Impact of CAOi inhibition of the antenna complex on accumulation of starch in Camelina and the number of granules per cross-sectional view of the thylakoid under electron microscopic examination.
Figure 11B:
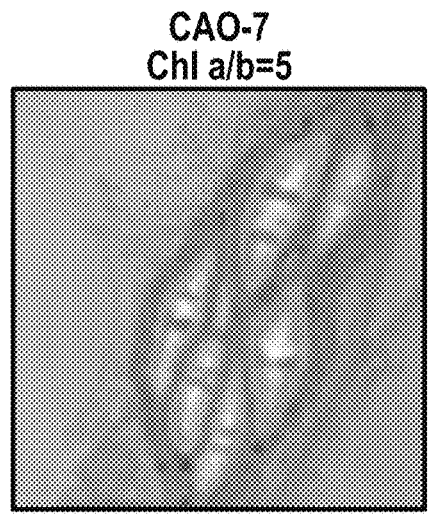
Figure 11C:
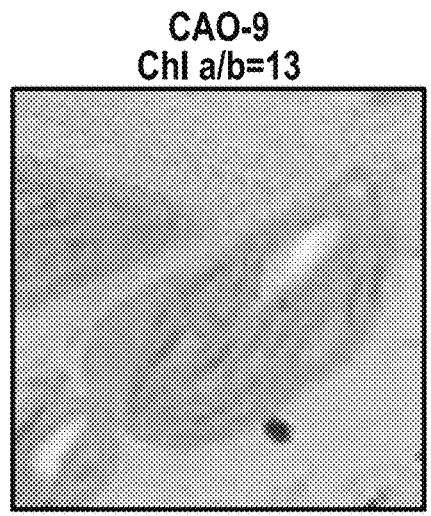
Figure 11D:
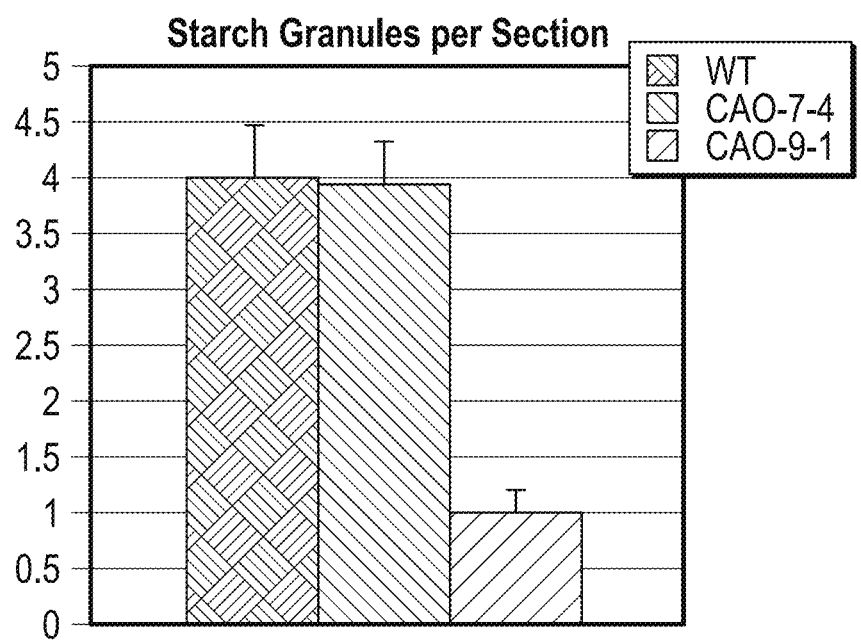

Referring now to FIG. 10, comparison of the proteins associated with the photosynthetic complexes of wild-type and CAOi mutant lines of *Camelina*. Electrophoresis using blue native green gels show the photosynthetic complex of wild-type compared to CAOi mutant expressing Chl a/b ratio of 6.2 shows an altered makeup of the proteins related to light capture such as the PSII/LHC II supercomplexes and the LHC II trimer.

Referring now to FIG. 11A-D, the impact of CAOi inhibition of the antenna complex on accumulation of starch in *Camelina* is demonstrated. The CAO-7 mutant with a Chl a/b ratio of 5 had similar starch deposition to that of wild-type. However, high expression of the CAOi system in CAO-9 led to a strong decrease in the amount of starch granules seen per section.

Figures 12A, 12B:
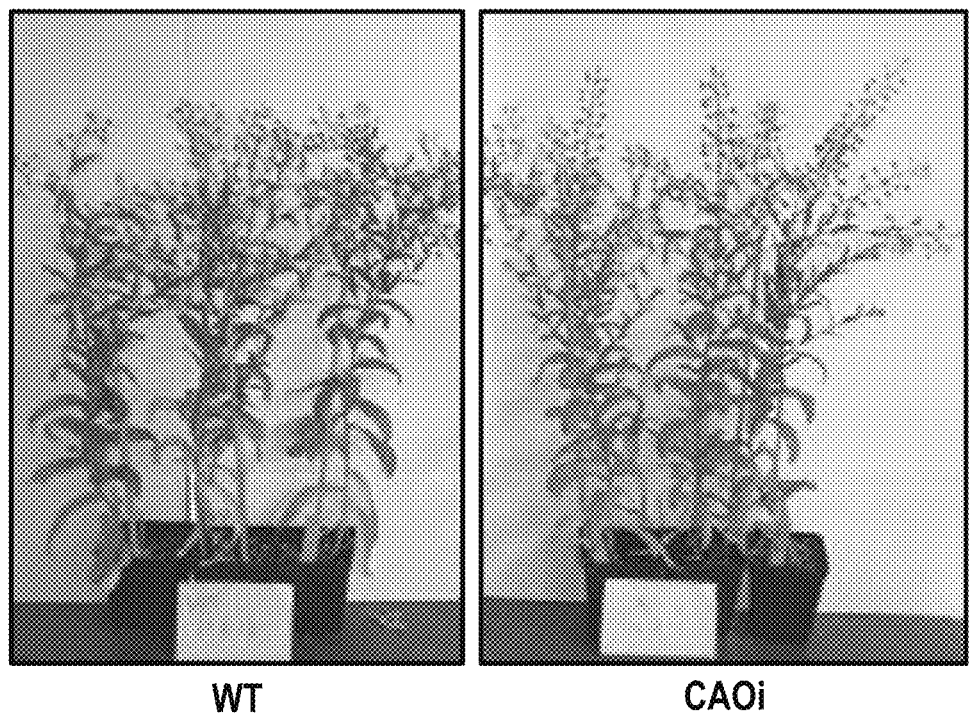
FIG. 12A-B—Camelina CAOi mutant plants (CAOi) compared to wild-type plants (WT) have more leaves and extended lifetimes.

Referring now to FIG. 12, *Camelina* CAOi mutant plants compared to wild-type plants had more lower leaves with extended lifetimes.

Figure 13:
FIG. 13—Camelina CAOi mutant line (CAOi 8-1; Chl a/b ratio 6) at three weeks in a greenhouse trial grows more rapidly than wild-type line (Chl a/b ratio=3).

Referring now to FIG. 13, *Camelina* CAOi mutant line (CAOi 8-1; Chl a/b ratio 6) at three weeks in a greenhouse trial grows more rapidly than wild-type line (Chl a/b ratio=3).

Figure 14A:
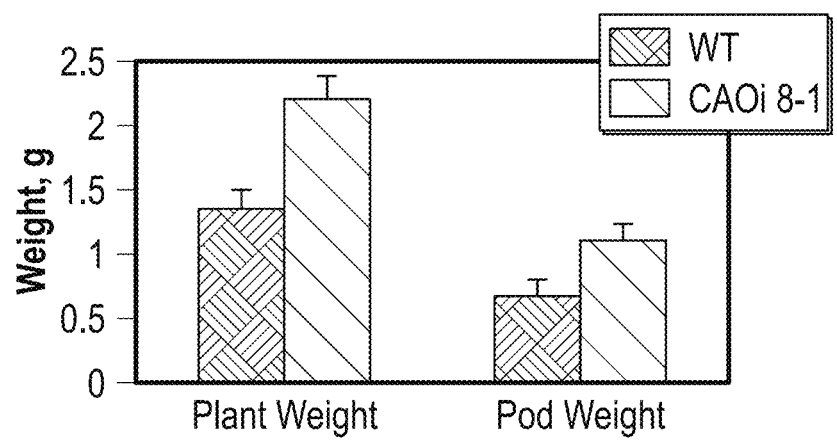
FIG. 14A-B—Comparison of CAOi line (CAOi 8-1) to wild-type lines for plant weight, pod weight and number of pods.
Figure 14B:
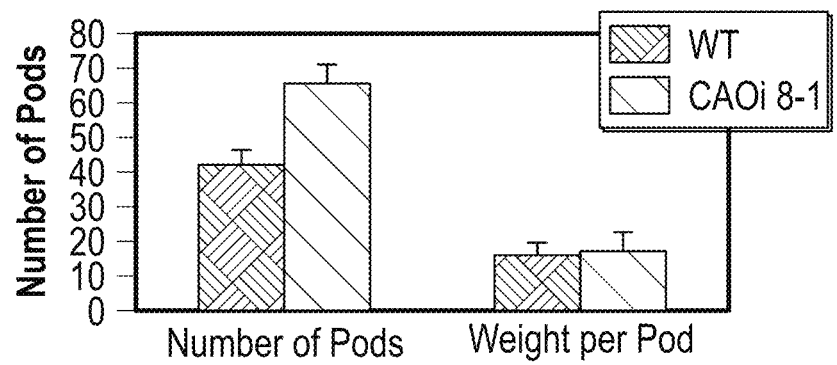

Referring now to FIG. 14A-B, comparison of a CAOi line (CAOi 8-1) to wild-type lines for plant weight, pod weight and number of pods. The overall biomass of the CAOi mutant line was significantly higher than wild-type. The overall weight of the pod fraction was significantly higher in the mutant than the wild-type. However, this reflected the number of pods produced rather than an increase in weight per pods.

Figure 15:
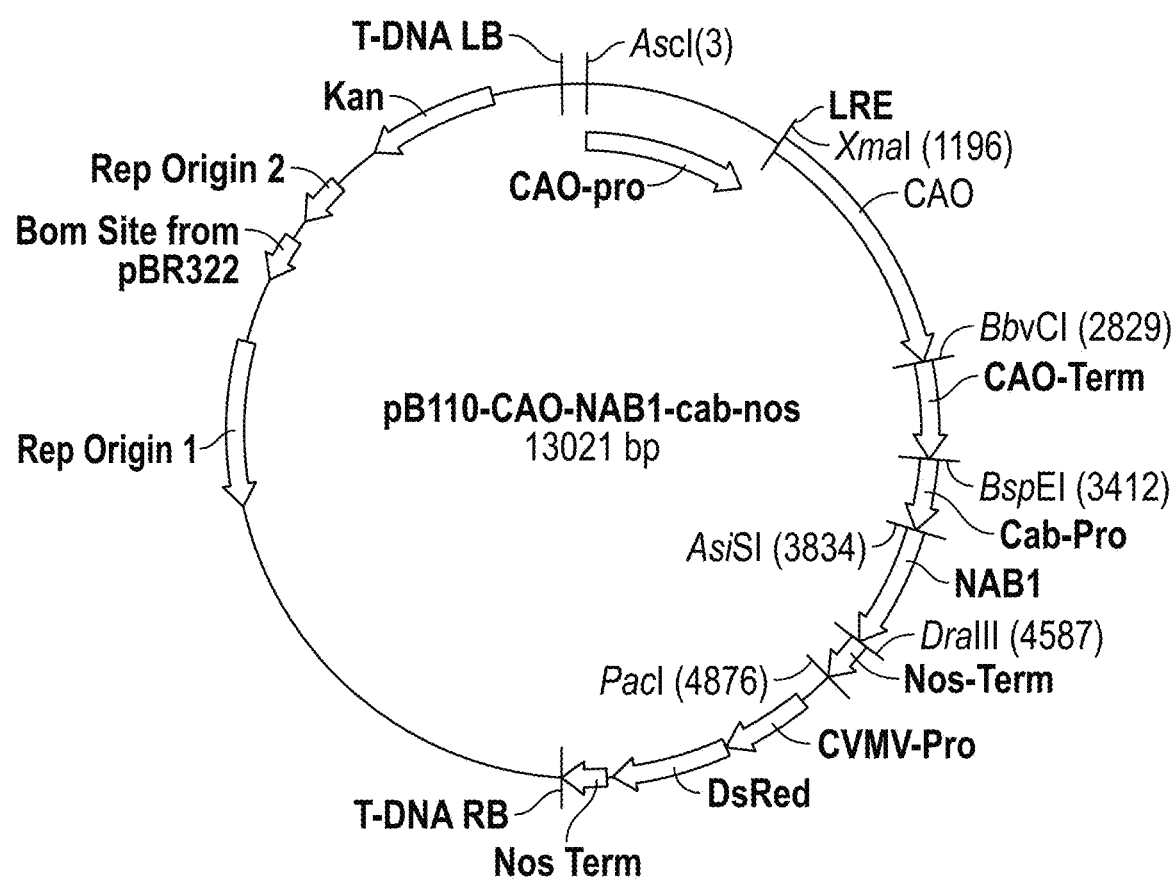
FIG. 15—Construct for transformation of Arabidopsis to generate a line as described in Example 4. Physical map of pb110-CAO-NAB-cab-nos Agrobacterium Ti-plasmid. Pb110 backbone was used to harbor an Arabidopsis CAO gene with a Chlamydomonas LRE (Light Responsive Element) fused to the 5' end of an Arabidopsis Cao gene driven by the Arabidopsis CAO-promoter (CAO-pro) and CAO-terminator (CAO-term); as well as NAB1 gene (from Chlamydomonas) driven by light-sensitive cab-promoter and nos-terminator). LB/RB T-DNA left/right border. The downstream (for promoter) or upstream (for terminator) DNA sequences of CAO gene from Arabidopsis so that translation of the gene is regulated by same promoter and terminator as in growing plant.

Referring now to FIG. 15, a map of the construct pB110-CAO0NAB1-cab-nos is provided. Physical map of pb110-CAO-NAB-cab-nos *Agrobacterium* Ti-plasmid. Pb110 backbone was used to harbor an *Arabidopsis* Cao gene with a *Chlamydomonas* LRE (Light Responsive Element) fused to the 5' end of an *Arabidopsis* Cao gene driven by the native *Arabidopsis* CAO-promoter (CAO-pro) and CAO-terminator (CAO-term); as well as NAB1 gene (from *Chlamydomonas*) driven by light-sensitive cab-promoter and nos-terminator). LB/RB T-DNA left/right border.

Embodiments of the present invention provides methods, and compositions for modulating the PSII peripheral antenna size of plants, specifically plants such as wheat, barley, *Arabidopsis, Camelina*, and any agriculturally or bioenergy important plant by negatively regulating the expression of the chlorophyll a oxygenase gene (Cao) to high light intensity in a tissue-specific manner.

Accordingly in one aspect, the current invention includes a method of producing an improved plant, comprising the steps of stably transforming a plant with a heterologous polynucleotide sequence comprising expression control sequences comprising a cold-shock domain consensus sequence (CSDDCS) motif, that is capable of binding to a redox-sensitive modulator that is responsive to ambient light intensity said control sequences are operably linked to a native or heterologous Cao gene selecting a transformant that is capable of modulating PSII antenna size in response to ambient light intensity.

In another embodiment, the current invention includes a method of enhancing yields of photosynthetic productivity under conditions of high light intensity, and or high density growth, the method comprising providing a plant comprising a heterologous polynucleotide sequence comprising expression control sequences comprising a cold-shock domain consensus sequence (CSDDCS) motif operatively coupled to a polynucleotide sequence encoding CAO; wherein expression of the Cao gene is increased at low light intensity, compared to the expression of the Cao gene at high light intensity and cultivating the plant at high light intensity and or high density.

In another embodiment, the current invention includes a method of enhancing production of carbon sink storage compounds, such as oil, starch and sugar, from a plant the method comprising providing the plant comprising a heterologous polynucleotide sequence comprising expression control sequences comprising a cold-shock domain consensus sequence (CSDDCS) motif operatively coupled to a polynucleotide sequence encoding the CAO protein, wherein expression of the cao is increased at low light intensity, compared to the expression of the Cao at high light intensity cultivating the plant at high light intensity and or high density. In another embodiment, the current invention includes a method of enhancing lipid and/or oil (suitable for biodiesel feedstocks) production from a plant the method comprising providing the plant comprising a heterologous polynucleotide sequence comprising expression control sequences comprising a cold-shock domain consensus sequence (CSDDCS) motif operatively coupled to a polynucleotide sequence encoding CAO, wherein expression of the cao is increased at low light intensity, compared to the expression of the Cao at high light intensity cultivating the plant at high light intensity and or high density.

In another embodiment the present invention includes a method of enhancing (3-carotene, lutein, or zeaxanthin levels from a plant, the method comprising providing plant comprising a heterologous polynucleotide sequence comprising expression control sequences comprising a cold-shock domain consensus sequence (CSDDCS) motif operatively coupled to a polynucleotide sequence encoding CAO, wherein expression of the Cao gene is increased at low light intensity, compared to the expression of the Cao gene at high light intensity cultivating the plant at high light intensity and or high density.

In yet another embodiment, the current invention includes transgenic plants produced by any of the methods described above.

Chlorophyll a Oxygenase (Cao)

The chlorophyll a oxygenase (CAO) may be in its native form (as found naturally in the plant), i.e., as different apoprotein forms or allelic variants as they appear in nature, which may differ in their amino acid sequence, for example, by truncation (e.g., from the N- or C-terminus or both) or other amino acid deletions, additions, insertions, substitutions, or post-translational modifications. Naturally occurring chemical modifications including post-translational modifications and degradation products of CAO, are also specifically included in any of the methods of the invention including for example, pyroglutamyl, iso-aspartyl, proteolytic, phosphorylated, glycosylated, reduced, oxidized, isomerized, and deaminated variants of CAO.

The CAO, which may be used in the invention including any of the methods of the invention, may have amino acid sequences which are substantially homologous, or substantially similar to the native CAO amino acid sequences, for example, to any of the native Cao sequences provided in the sequence listing. Alternatively, the CAO may have an amino acid sequence having at least 30% preferably at least 40, 50, 60, 70, 75, 80, 85, 90, 95, 98, or 99% identity with Cao genes encoding the proteins in SEQ ID Nos 1-5. In a preferred embodiment, the chlorophyll a oxygenase gene for use in any of the methods of the present invention is at least 80% identical to the mature CAO from *Chlamydomonas*.

Suppression of Chlorophyll a Oxygenase Gene (Cao) Expression

The invention provides methods, compositions, and transgenic plants having a reduced chlorophyll antenna size by suppressing the endogenous expression of Cao, and operatively coupling the expression of a heterologous Cao gene to expression control sequences that are regulated by the activity of a redox-sensitive modulator. Accordingly in one aspect, the present invention includes transgenic plants in which the endogenous Cao gene has been knocked out or the expression of the gene suppressed.

Exemplary chlorophyll a oxygenase nucleic acid sequences can be used to prepare expression cassettes useful for inhibiting or suppressing chlorophyll a oxygenase expression, and for providing for heterologous recombinant Cao genes, are identified in the sequence listing. A number of methods can be used to inhibit gene expression in plants. For instance, siRNA, antisense, or ribozyme technology can be conveniently used for designing new crop plants with improved yields and/or disease resistance (Ali et al., 2010).

For antisense expression, a nucleic acid segment from the desired chlorophyll a oxygenase gene is cloned and operably linked to a promoter such that the antisense strand of chlorophyll a RNA will be transcribed. The expression cassette is then transformed into plants, e.g., Camelina, and the antisense strand of RNA is produced. The antisense nucleic acid sequence transformed into plants will be substantially identical to at least a portion of the endogenous gene or genes to be repressed. The sequence, however, does not have to be perfectly identical to inhibit expression. Thus, an antisense or sense nucleic acid molecule encoding a portion of the entire chlorophyll a oxygenase gene can be useful for producing a plant in which chlorophyll a oxygenase expression is suppressed. This is often referred to as a knockdown mutant in contrast to a knockout mutant with the gene target itself is modified. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred. Sequences can also be longer, e.g., 1000 or 2000 nucleotides or greater in length.

Catalytic RNA molecules or ribozymes can also be used to inhibit expression of chlorophyll a oxygenase genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA cleaving activity upon them, thereby increasing the activity of the constructs.

A number of classes of ribozymes have been identified. One class of ribozymes is derived from a number of small circular RNAs that are capable of self-cleavage and replication in plants. Ribozymes, e.g., Group I introns, have also been identified in the chloroplast of green algae (see, e.g., Cech et al., (1990) Annu Rev Biochem 59:543-568; Bhattacharya et al., (1996) Molec Biol and Evol 13:978-989; Erin, et al., (2003) Amer J Botany 90:628-633; Turmel, et al., (1993) Nucl Acids Res. 21:5242-5250; and Van Oppen et al., (1993) Molec Biol and Evol 10:1317-1326). The design and use of target RNA-specific ribozymes is described, e.g., in Haseloff et al. (1988) Nature, 334:585-591.

Another method of suppression is sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., (1990) The Plant Cell 2:279-289; Flavell, (1994) Proc. Natl. Acad. Sci., USA 91:3490-3496; Kooter and Mol, (1993) Current Opin. Biol. 4: 166-171; and U.S. Pat. Nos. 5,034,323, 5,231,020, and 5,283, 184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 90% or 95% to absolute identity would be most preferred. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are over-expressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Endogenous gene expression may also be suppressed by means of RNA interference (RNAi), which uses a double-stranded RNA having a sequence identical or similar to the sequence of the target chlorophyll a oxygenase gene. See generally, PCT International Publication Nos. WO 99/32619 WO 99/07409, WO 00/44914. WO 00/44895, WO 00/63364 WO 00/01846, WO 01/36646, WO 01/75164, WO01/29058, WO 02/055692, WO 02/44321, WO2005/054439, and WO2005/110068.

RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. The introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., (2000); Proc. Natl. Acad. Sci. USA 97:4985 Waterhouse et al., (1998) Proc. Natl. Acad. Sci. USA 95:13959-13964; Tabara et al. (1998) Science 282: 430-431). For example, to achieve suppression of the expression of a DNA encoding a protein using siRNA, a double-stranded RNA having the sequence of a DNA encoding the protein, or a substantially similar sequence thereof (including those engineered not to translate the protein) or fragment thereof, is introduced into a plant of interest, e.g., wheat. The resulting plants may then be screened for a phenotype associated with the target protein and/or by monitoring steady-state RNA levels for transcripts encoding the protein. Although the nucleic acids forming the basis for RNAi need not be completely identical to the targeted gene, they may be at least 70%, 80%, 90%, 95% or more identical to the CAO targeted gene sequence; such as, for example, a gene from SEQ ID NO 1-5 and fragments thereof. See, e.g., U.S. Patent Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211, and the current examples.

The siRNA polynucleotides may encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 15, 20, 25, 30, 50, 100, 150, 200, or more nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases. Thus, siRNA fragments may be selected for similarity or identity with the N terminal region of the chlorophyll a oxygenase sequences of the invention (i.e., those sequences lacking significant homology to sequences in the databases) or may be selected for identity or similarity to conserved regions of chlorophyll a oxygenase proteins.

Expression vectors that continually express siRNA in transiently- and stably-transfected cells have been engineered to express small hairpin RNAs, which get processed in vivo into siRNAs molecules capable of carrying out gene-specific silencing (Brummelkamp et al., (2002) Science 296:550-553, and Paddison, et al., (2002) Genes & Dev. 16:948-958). Post-transcriptional gene silencing by double-stranded RNA is discussed in further detail by Hammond et al. Nature Rev Gen 2:110-119 (2001), Fire et al. (1998) Nature 391:806-811 and Timmons and Fire (1998) Nature 395:854.

One of skill in the art will recognize that using technology based on specific nucleotide sequences (e.g., antisense or sense suppression technology), families of homologous genes can be suppressed with a single sense or antisense transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most variation between family members.

Light Regulated Translational Modulators

The present invention exploits the ability of certain proteins (redox-sensitive modulators) to act as reversible thiol-based redox switches to regulate gene expression in plants to enable the light dependent regulation of PSII antenna size. Such proteins represent a growing family of proteins that is widely dispersed within the plant and animal kingdoms. See generally Antelmann H, & Heimann J D. (2010), Brandes et al., (2009) Thiol-based redox switches in eukaryotic proteins. Antioxid Redox Signal. 11(5):997-1014, Paget M S, & Buttner M J. (2003) Thiol-based regulatory switches. Annu Rev Genet. 37:91-121.

The cold shock domain (CSD) is among the most ancient and well conserved nucleic acid binding domains from bacteria to higher animals and plants (Chsikam et al., BMB Reports (2010) 43(1) 1-8; Nakaminami et al., (2006) 103 (26) 10123-10127).

Proteins containing a CSD motif are also referred to as Y box proteins and eukaryotic members of this large family generally contain a secondary auxiliary RNA domain which modulates the RNA affinity of the protein, but can be dispensable for selective RNA recognition.

An exemplary redox-sensitive modulator includes the cytosolic RNA binding protein NAB 1 (SEQ. ID. NO. 6) from Chlamydomonas. NAB 1 harbors 2 RNA binding motifs and one of these motifs, located at the N-terminus, is a cold shock domain. NAB 1 represses the translation of LHC II (light harvesting complex of photosystem II) by sequestering the encoding mRNAs into translationally silent mRNA complexes. (Mussgnug et al., The Plant Cell (2005) 17 3409-3421).

NAB 1 contains 2 cysteine residues, Cys-81 and Cys-226, within its C-terminal RNA recognition motif. Modification of these cysteines either by oxidation or by alkylation in vitro is accompanied by a decrease in RNA binding affinity for the target mRNA sequence. Recent studies have confirmed that NAB 1 is fully active in its dithiol reduced state, and is reversibly deactivated by modification of its cysteines. (Wobbe et al., (2009) Pro. Nat. Acad. Sci. 106(32) 13290-13295).

NAB 1 and NAB 1-like redox-sensitive modulators from a number of different species have been sequenced, and are known in the art to be at least partially functionally interchangeable. It would thus be a routine matter to identify and select a variant being a NAB 1 or NAB 1-like protein from a species or genus other than Chlamydomonas. Several such variants of NAB 1 or NAB 1-like redox-sensitive modulators from a number of species are identified by their amino acid sequence in SEQ. ID. Nos. 6-17.

Thus all such homologues, orthologs, and naturally occurring isoforms of NAB 1 from Chlamydomonas as well as other species (SEQ. ID. NOs. 6-17) are included in any of the methods and kits of the invention, as long as they retain detectable activity. It will be understood that for the recombinant production of NAB 1 in different species it will typically be necessary to codon optimize the nucleic acid sequence of the gene for the organism in question. Such codon optimization can be completed by standard analysis of the preferred codon usage for the organism in question, and the synthesis of an optimized nucleic acid via standard DNA synthesis. A number of companies provide such services on a fee for services basis and include for example, DNA2.0, (CA, USA) and Operon Technologies. (CA, USA).

It is known in the art to synthetically modify the sequences of proteins or peptides, while retaining their useful activity, and this may be achieved using techniques which are standard in the art and widely described in the literature, e.g., random or site-directed mutagenesis, cleavage, and ligation of nucleic acids, or via the chemical synthesis or modification of amino acids or polypeptide chains. For instance, conservative amino acid mutation changes can be introduced into NAB 1 protein and are considered within the scope of the present invention.

The NAB 1 and NAB 1-like redox-sensitive modulators may thus include one or more amino acid deletions, additions, insertions, and/or substitutions based on any of the naturally-occurring isoforms of NAB 1. These may be contiguous or non-contiguous. Representative variants may include those having 1 to 8, or more preferably 1 to 4, 1 to 3, or 1 or 2 amino acid substitutions, insertions, and/or deletions as compared to any of sequences of SEQ. ID. NOs 6-17.

NAB 1 and NAB 1-like redox-sensitive modulator polypeptides which may be used in any of the methods of the invention may have amino acid sequences which are substantially homologous, or substantially similar to any of the NAB 1 sequences of SEQ. ID. NOs 6-17. Alternatively, the NAB 1 and NAB 1-like redox-sensitive modulators may have an amino acid sequences having at least 30% preferably at least 40, 50, 60, 70, 75, 80, 85, 90, 95, 98, or 99% identity with a NAB 1 or NAB 1-like redox-sensitive modulators listed in SEQ. ID. NOs 6-17. In one aspect, the NAB 1 or and NAB 1-like redox-sensitive modulator is substantially homologous, or substantially similar to SEQ. ID. NO. 6.

Fragments of endogenous or synthetic NAB 1 or and NAB 1-like redox-sensitive modulator sequences may also have the desirable functional properties of the peptide from which they were derived and may be used in any of the methods of the invention. The term "fragment" as used herein thus includes fragments of NAB 1 provided that the fragment retains the biological activity of the whole molecule. The fragment may also include an N-terminal or C-terminal fragment of NAB 1. Preferred fragments comprise residues 1-80 of the endogenous NAB 1 or and NAB 1-like redox-sensitive modulator, comprising the cold shock domain, or residues 160 to 247 comprising the RNA recognition motif. Also included are fragment s having N- and I or C-terminal extensions or flanking sequences. The length of such extended peptides may vary, but typically are not more than 50, 30, 25, or 20 amino acids in length.

Fusion proteins of NAB 1, and fragments of NAB 1 to other proteins are also included, and these fusion proteins may enhance the biological activity of NAB 1, targeting, binding or redox sensitivity. It will be appreciated that a flexible molecular linker (or spacer) optionally may be interposed between, and covalently join, the NAB 1 and any of the fusion proteins disclosed herein. Any such fusion protein many be used in any of the methods of the present invention.

Variants may include, e.g., different allelic variants as they appear in nature, e.g., in other species or due to geographical variation. All such variants, derivatives, fusion proteins, or fragments of NAB 1 are included, may be used in any of the methods claims disclosed herein, and are subsumed under the term "NAB 1".

The variants, derivatives, and fragments are functionally equivalent in that they have detectable redox dependent RNA binding activity. More particularly, they exhibit at least 40%, preferably at least 60%, more preferably at least 80% of the activity of wild-type NAB 1, particularly *Chlamydomonas* NAB 1. Thus they are capable of functioning as NAB 1, i.e., can substitute for NAB 1 itself.

Such activity means any activity exhibited by an endogenous NAB 1 or and NAB 1-like redox-sensitive modulator, whether a physiological response inhibited in an in vivo or in vitro test system, or any biological activity or reaction mediated by an endogenous NAB 1 or and NAB 1-like redox-sensitive modulator (e.g., in an enzyme assay or in binding to test tissues, nucleic acids, or metal ions).

Thus, it is known that NAB 1 binds to cold shock domain consensus sequence motifs, for example as provided in SEQ ID Nos 18-26. An assay for NAB 1 activity can thus be made by assaying for redox dependent binding to a nucleic acid comprising a cold shock domain consensus sequence motif. Such an assay is described in Wobbe et al., (2009) Proc. Natl. Acad. Sci. USA 106 (32) 13290-13295.

In one aspect of any of these methods and transgenic organisms, the NAB 1 or and NAB 1-like redox-sensitive modulator is endogenous to the organism. In another aspect of any of these methods and transgenic organisms, the NAB 1 is heterologous to the transgenic organism.

Plants

The present invention can be practiced with any plant with light harvesting antenna. Previous application of this technology in algae (Sayre WO2013/016267) has demonstrated that single-celled photosynthetic eukaryotes are capable of modulation of antenna size under different light intensities. This previous invention did not contemplate tissue-specific expression in plants nor the improved production of storage tissues such as starch and oils observed in the present invention. The present invention demonstrates that this is also possible with the more complex, tissue-specific complexes in higher plants and that unexpected results occurred in the deposition of starch and other storage compounds. The plants used with the invention can include any naturally occurring plant species or any genetically engineered plant. The plant used with the invention includes any commercially available strain, any strain native to a particular region, or any proprietary strain. Additionally, the plant can be of any Division, Class, Order, Family, Genus, or Species, or any subsection thereof. Another contrast with the WO2013/016267 invention is the improved growth rate of the transformed plants versus wild-type.

In certain embodiments, the plants used with the methods of the invention can be members of any division in the plant kingdom (Plantae) whether vascular or non-vascular, monocot or dicot, land or water plant. In one aspect of the invention the plants are chosen from land plants. In a further aspect the plants are chosen from those important to agriculture or biofuel production. In a further aspect, the plants are chosen from seed bearing plants.

Plants that could be of particular importance in the application of this invention are seed crops such as but not limited to millet, corn (maize), sorghum, barley, oats, rice, rye, teff, triticale, wheat, rice, wild rice, amaranth, beans, lentils, fava, lupin, peanuts, chickpeas, pigeon peas, soybeans, mustards, rape seed (canola), safflower, sunflower, flax, jatropa, hemp, and poppy.

Plants that could be of particular importance in the application of this invention are biomass crops such as but not limited to trees (poplar, willow, *eucalyptus*, southern beech, sycamore, ash), *miscanthus*, hemp, switchgrass, reed canary grass, rye, and giant reed.

Plants that could be of particular importance in the application of this invention are sugar, starch and oil crops such as but not limited to beets, sweet sorghum, sugar cane, potatoes, sweet potatoes, cassava, olives, soybean, rapeseed, corn, and linseed.

In one aspect of any of the claimed methods, plants of the following species are preferred, *Camelina* and *Arabidopsis*.

Expression Vectors

In any of these embodiments, an expression vector can be used to deliver a nucleic acid molecule comprising expression control sequences comprising a cold-shock domain consensus sequence (CSDDCS) motif operatively coupled to a polynucleotide sequence encoding CAO. In one aspect the expression vector will further comprise a promoter operatively coupled to the CSDDCS motif and drives expression of the CAO coding region. Typically the CSD-DCS motif is inserted between the promoter and the start of the Cao start codon.

In one aspect, the expression vector comprises a CSD-DCS motif is substantially identical to a sequence selected from the group consisting of SEQ ID. No. 18, SEQ ID. No. 19, SEQ ID. No. 20, SEQ ID. No. 21, SEQ ID. No. 22, SEQ ID. No. 23, SEQ ID. No. 24, SEQ ID. No. 25, and SEQ ID. No. 26.

In different embodiments the Cao gene may be an endogenous gene from the plant to be used with the expression vector. Accordingly in different aspects the Cao gene may be any plant Cao gene. In one aspect, the Cao gene is substantially identical to a sequence selected from the group consisting of SEQ ID. No. 1, SEQ ID. No. 2, SEQ ID. No. 3, SEQ ID. No. 4, and SEQ ID. No. 5.

In any of these embodiments, a vector can also be used to deliver a nucleic acid molecule encoding a silencing RNA into a plant cell to enable the suppression of the expression of the endogenous CAO in the cell.

The expression vectors can be, for example, DNA plasmids or viral vectors. Various expression vectors are known in the art. The selection of the appropriate expression vector can be made on the basis of several factors including, but not limited to the cell type wherein expression is desired. For example, *Agrobacterium*-based expression vectors can be used to express the nucleic acids of the presently disclosed subject matter when stable expression of the vector insert is sought in a plant cell.

In other embodiments of the invention, it is contemplated that one may wish to employ replication-competent viral vectors for plant transformation. Such vectors include, for example, wheat dwarf virus (WDV) "shuttle" vectors, such as pW 1-11 and pW 1-GUS (Ugaki et al., 1991). These vectors are capable of autonomous replication in maize cells as well as *E. coli*, and as such may provide increased sensitivity for detecting DNA delivered to transgenic cells. A replicating vector also may be useful for delivery of genes flanked by DNA sequences from transposable elements such as Ac/Ds, or Mu. It has been proposed that transposition of these elements within the maize genome requires DNA replication (Laufs et al, 1990). It also is contemplated that transposable elements would be useful for producing transgenic plants lacking elements necessary for selection and maintenance of the plasmid vector in bacteria, e.g., antibiotic resistance genes, or other selectable markers, and origins of DNA replication. It also is proposed that use of a transposable element such as Ac, Ds, or Mu would actively promote integration of the desired DNA and hence increase the frequency of stably transformed cells.

Promoters

The expression of the nucleotide sequence of the expression cassette can be under the control of a constitutive promoter or an inducible promoter that initiates transcription only when the transformed cell is exposed to some particular external stimulus. Basal promoters in plants typically comprise canonical regions associated with the initiation of transcription, such as CAAT and TATA boxes. The TATA box element is usually located approximately 20 to 35 nucleotides upstream of the initiation site of transcription. The CAAT box element is usually located approximately 40 to 200 nucleotides upstream of the start site of transcription. The location of these basal promoter elements result in the synthesis of a RNA transcript comprising nucleotides upstream of the translational ATG start site. The region of RNA upstream of the ATG is commonly referred to as a 5' untranslated region or 5' UTR. It is possible to use standard molecular biology techniques to make combinations of basal promoters, that is, regions comprising sequences from the CAAT box to the translational start site, with other upstream promoter elements to enhance or otherwise alter promoter activity or specificity.

The promoters may be altered to contain "enhancer DNA" to assist in elevating gene expression. As is known in the art certain DNA elements can be used to enhance the transcription of DNA. These enhancers often are found 5' to the start of transcription in a promoter that functions in eukaryotic cells, but can often be inserted upstream (5') or downstream (3') to the coding sequence. In some instances, these 5' enhancer DNA elements are introns. Among the introns that are particularly useful as enhancer DNA are the 5' introns from the rice actin 1 gene (see U.S. Pat. No. 5,641,876), the rice actin 2 gene, the maize alcohol dehydrogenase gene, the maize heat shock protein 70 gene (U.S. Pat. No. 5,593,874), the maize shrunken 1 gene, the light sensitive I gene of *Solanum tuberosum*, and the heat shock protein 70 gene of *Petunia hybrida* (U.S. Pat. No. 5,659,122).

For in vivo expression in plants, exemplary constitutive promoters include those derived from the CaMV 35S, rice actin, and maize ubiquitin genes, each described herein below.

Exemplary inducible promoters for this purpose include the chemically inducible PR-promoter and a wound-inducible promoter, also described herein below. Selected promoters can direct expression in specific cell types (such as leaf epidermal cells, mesophyll cells, root cortex cells) or in specific tissues or organs (roots, leaves or flowers, for example). Exemplary tissue-specific promoters include the well-characterized leaf-specific promoters, each described herein below.

Depending upon the cell system utilized, any one of a number of suitable promoters can be used. Promoter selection can be based on expression profile and expression level. The following are representative non-limiting examples of promoters that can be used in the expression cassettes.

35S Promoter. The CaMV 35S promoter can be used to drive constitutive gene expression. Construction of the plasmid pCGN1 761 is described in the published European Patent Application EP 0 392 225, which a CaMV 35S promoter and the tml transcriptional terminator with a unique EcoRI site between the promoter and the terminator and has a pUC-type backbone.

Actin Promoter. Several isoforms of actin are known to be expressed in most cell types and consequently the actin promoter is a good choice for a constitutive promoter. In particular, the promoter from the rice Act 1 gene has been cloned and characterized (McElroy et al., 1990). A 1.3 kb fragment of the promoter was found to contain inter alia the regulatory elements required for expression in rice protoplasts. Furthermore, numerous expression vectors based on the Act 1 promoter have been constructed specifically for use in monocotyledons (McElroy et al., 1991). These incorporate the Act 1-intron 1, Adbl 5' flanking sequence and Adbl-intron 1 (from the maize alcohol dehydrogenase gene) and sequence from the CaMV 35S promoter. Vectors showing highest expression were fusions of 35S and Act 1 intron or the Act 1 5' flanking sequence and the Act 1-intron. Optimization of sequences around the initiating ATG (of the GUS reporter gene) also enhanced expression.

Ubiquitin Promoter. Ubiquitin is another gene product known to accumulate in many cell types and its promoter has been cloned from several species for use in transgenic plants (e.g. sunflower—Binet et al., 1991 and maize—Christensen et al, 1989). The maize ubiquitin promoter has been developed in transgenic monocot systems and its sequence and vectors constructed for monocot transformation are disclosed in the European Patent Publication EP 0 342 926 which is herein incorporated by reference. Taylor et al., 1993 describe a vector (pAHC25) that comprises the maize ubiquitin promoter and first intron and its high activity in cell suspensions of numerous monocotyledons when introduced via microparticle bombardment. The ubiquitin promoter is suitable for gene expression in transgenic plants, especially monocotyledons. Suitable vectors are derivatives of pAHC25 or any of the transformation vectors described in this application, modified by the introduction of the appropriate ubiquitin promoter and/or intron sequences.

Inducible Expression Chemically Inducible PR-1a Promoter. The double 35S promoter in pCGN 1 761ENX can be replaced with any other promoter of choice that will result in suitably high expression levels. By way of example, one of the chemically inducible promoters described in U.S. Pat. No. 5,614,395 can replace the double 35S promoter.

The promoter of choice is preferably excised from its source by restriction enzymes, but alternatively can be PCR-amplified using primers that carry appropriate terminal restriction sites.

The selected target gene coding sequence can be inserted into this vector, and the fusion products (i.e., promoter-gene-terminator) can subsequently be transferred to any selected transformation vector, including those described below. Various chemical regulators can be employed to induce expression of the selected coding sequence in the plants transformed according to the presently disclosed subject matter, including the benzothiadiazole, isonicotinic acid, and salicylic acid compounds disclosed in U.S. Pat. Nos. 5,523,311 and 5,614,395, herein incorporated by reference.

Transcriptional Terminators. A variety of transcriptional terminators are available for use in expression cassettes. These are responsible for the termination of transcription beyond the transgene and its correct polyadenylation.

Appropriate transcriptional terminators are those that are known to function in the relevant plant system. Representative plant transcriptional terminators include the CaMV 35S terminator, the tml terminator, the nopaline synthase terminator, and the pea rbcS E9 terminator. With regard to RNA polymerase III terminators, these terminators typically comprise—52 run of 5 or more consecutive thymidine residues. In one embodiment, an RNA polymerase III terminator comprises the sequence TTTTTTT. These can be used in both monocots and dicots.

Sequences for the Enhancement or Regulation of Expression—Numerous sequences have been found to enhance the expression of an operatively lined nucleic acid sequence, and these sequences can be used in conjunction with the nucleic acids of the presently disclosed subject matter to increase their expression in transgenic plants.

Various intron sequences have been shown to enhance expression, particularly in monocotyledonous cells. For example, the introns of the maize Adbl gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., 1987). In the same experimental system, the intron from the maize bronze gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMY) have been shown to be effective in enhancing expression (e.g. Gallie et al., 1987; Skuzeski et al., 1990).

*Agrobacterium* Transformation Vectors. Many vectors are available for transformation using *Agrobacterium tumefaciens* and may be used for plant transformation. These typically carry at least one T-DNA border sequence and include vectors such as pBIN 1 9 (Bevan, 1984) and related vectors.

Other Plant Transformation Vectors: Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation), vortexing with glass beads, and microinjection. The choice of vector can depend on the technique chosen for the species being transformed.

Selectable Markers: For certain target species, different antibiotic or herbicide selection markers can be preferred. Selection markers used routinely in transformation include the nptll gene, which confers resistance to kanamycin and related antibiotics (Messing & Vierra, 1982; Bevan et al., 1983), the bar gene, which confers resistance to the herbicide phosphinothricin (White et al., 1990; Spencer et al., 1990), the hph gene, which confers resistance to the antibiotic hygromycin (Blochlinger & Diggelmann, 1984), the dhfr gene, which confers resistance to methotrexate (Bourouis & Jarry, 1983), and the EPSP synthase gene, which confers resistance to glyphosate (U.S. Pat. Nos. 4,940,935 and 5,188,642).

Screenable Markers. An example of screenable markers that may be employed include a β-glucuronidase or uidA gene (Jefferson et al., 1986; the protein product is commonly referred to as GUS), isolated from *E. coli*, which encodes an enzyme for which various chromogenic substrates are known; an R-locus gene, which encodes a product that regulates the production of anthocyanin pigments (red color) in plant tissues (Dellaporta et al., 1988); a P-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an alpha-amylase gene (Ikuta et al., 1990); a tyrosinase gene (Katz et al., 1983) which encodes an enzyme capable of oxidizing tyrosine to DOPA and dopaquinone which in time condenses to form the easily-detectable compound melanin; a β-galactosidase gene, which encodes an enzyme for which there are chromogenic substrates; a luciferase (Lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; PCT Publication WO 97/41228).

The R gene complex in maize encodes a protein that acts to regulate the production of anthocyanin pigments in most seed and plant tissue. Maize strains can have one, or as many as four, R alleles which combine to regulate pigmentation in a developmental and tissue-specific manner. Thus, an R gene introduced into such cells will cause the expression of a red pigment and, if stably incorporated, can be visually scored as a red sector. If a maize line carries dominant alleles for genes encoding for the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR I 12, a K55 derivative which has the genotype r-g, b, Pl. Alternatively, any genotype of maize can be utilized if the CI and R alleles are introduced together.

It further is proposed that R gene regulatory regions may be employed in chimeric constructs in order to provide mechanisms for controlling the expression of chimeric genes. More diversity of phenotypic expression is known at the R locus than at any other locus (Coe et al., 1988). It is contemplated that regulatory regions obtained from regions 5' to the structural R gene would be valuable in directing the expression of genes for, e.g., insect resistance, herbicide tolerance or other protein coding regions. For the purposes of the present invention, it is believed that any of the various R gene family members may be successfully employed (e.g., P, S, Le, etc.). However, the most preferred will generally be Sn (particularly Sn:bol3). Sn is a dominant member of the R gene complex and is functionally similar to the R and B loci in that Sn controls the tissue-specific deposition of anthocyanin pigments in certain seedling and plant cells, therefore, its phenotype is similar to R.

Other markers provide for visible light emission as an easily screened phenotype. A selectable marker contemplated for use in the present invention is firefly luciferase, encoded by the Lux gene. The presence of the tux gene in transformed cells may be detected using, for example, X-ray film, scintillation counting, fluorescent spectrophotometry, low-light video cameras, photon counting cameras or multiwell luminometry. It also is envisioned that this system may be developed for population screening for bioluminescence, such as on tissue culture plates, or even for whole plant screening. The gene which encodes green fluorescent protein (GFP) is contemplated as a particularly useful reporter gene (Sheen et al., 1995; Haseloff et al., 1997; Reichel et al., 1996; Tian et al., 1997; PCT Publication WO 97/41228). Expression of green fluorescent protein may be visualized in a cell or plant as fluorescence following illumination by particular wavelengths of light. Where use of a selectable marker gene such as Lux or GFP is desired, the inventors contemplated that benefit may be realized by creating a gene fusion between the selectable marker gene and a selectable marker gene, for example, a GFP-NPTII gene fusion (PCT Publication WO 99/60129). This could allow, for example, selection of transformed cells followed by screening of transgenic plants or seeds. In a similar manner, it is possible to utilize other readily available fluorescent proteins such as red fluorescent protein (CLONTECH, Palo Alto, Calif.).

Methods of Transformation

Suitable methods for plant transformation for use. with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. Nos. 5,302,523, and 5,464,765, each specifically incorporated herein by reference in their entirety), by Agrobacterium-mediated transformation (U.S. Pat. Nos. 5,591,616 and 5,563,055; each specifically incorporated herein by reference) and by acceleration of DNA coated particles (U.S. Pat. Nos. 5,550,318; 5,538,877; and 5,538,880; each specifically incorporated herein by reference in their entirety), and etc. Through the application of techniques such as these, maize cells as well as those of virtually any other plant species may be stably transformed and these transformed cells developed into transgenic plants. In certain embodiments, acceleration methods are preferred and include, for example, microparticle bombardment and the like.

Electroporation

Where one wishes to introduce DNA by means of electroporation, it is contemplated that the method of Krzyzek et al. (U.S. Pat. No. 5,384,253, incorporated herein by reference in its entirety) will be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation by mechanical wounding.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species that have been transformed by electroporation of intact cells include maize (U.S. Pat. No. 5,384,253; D'Halluin et al., 1992), wheat (Zhou et al., 1993), and soybean (Christou et al., 1987).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in PCT Publication WO 92/17598 (specifically incorporated herein by reference). Other examples of species for which protoplast transformation has been described include barley (Lazerri, 1995), sorghum (Battraw and Hall, 1991), maize (Bhattacharjee et al., 1997), wheat (He et al., 1994) and tomato (Tsukada, 1989).

Microparticle Bombardment

One method for delivering transforming DNA segments to plant cells in accordance with the invention is microparticle bombardment (U.S. Pat. Nos. 5,550,318; 5,538,880; 5,610,042; and PCT Publication WO 95/06128; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microparticle bombardment. However, it is contemplated that particles may contain DNA rather than be coated with DNA. Hence, it is proposed that DNA-coated particles may increase the level of DNA delivery via particle bombardment but are not, in and of themselves, necessary. For the bombardment, cells in suspension are concentrated on filters or solid culture medium. Alternatively, immature embryos or other target cells may be arranged on solid culture medium. The cells to be bombarded are positioned at an appropriate distance below the microparticle stopping plate.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microparticle bombardment techniques are widely applicable, and may be used to transform virtually any plant species. Examples of species for which have been transformed by microparticle bombardment include monocot species such as maize (PCT Publication WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Tarbet et al., 1995; Tarbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (Van Eck et al. 1995), and legumes in general (U.S. Pat. No. 5,563,055, specifically incorporated herein by reference in its entirety).

Agrobacterium-Mediated Transformation

Agrobacterium-mediated transfer is a preferred system that is widely applicable for introducing genes into plant. The use of Agrobacterium-mediated plant integrating vectors to introduce DNA into plant cells is well known in the art. See, for example, the methods described by Fraley et al. (1985), Rogers et al. (1987) and U.S. Pat. No. 5,563,055, specifically incorporated herein by reference in its entirety.

Agrobacterium-mediated transformation is most efficient in dicotyledonous plants and is the preferable method for transformation of dicots, including Arabidopsis, tobacco, tomato, and potato. Indeed, while Agrobacterium-mediated transformation has been routinely used with dicotyledonous plants for a number of years, it has only recently become applicable to monocotyledonous plants. Advances in Agrobacterium-mediated transformation techniques have now made the technique applicable to nearly all monocotyledonous plants. For example, Agrobacterium-mediated transformation techniques have now been applied to rice (Hiei et al., 1997; Zhang et al., 1997; U.S. Pat. No. 5,591,616, specifically incorporated herein by reference in its entirety), wheat (McCormac et al., 1998), barley (Tingay et al., 1997; McCormac et al., 1998), and maize (Ishida et al., 1996; U.S. Pat. No. 5,981,840).

Modern Agrobacterium transformation vectors are capable of replication in E. coli as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide encoding genes.

The vectors described (Rogers et al., 1987) have convenient multi-linker regions flanked by a promoter and a polyadenylation site for direct expression of inserted polypeptide encoding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

A number of wild-type and disarmed strains of Agrobacterium tumefaciens and Agrobacterium rhizogenes harboring Ti or Ri plasmids can be used for gene transfer into plants. Preferably, the Agrobacterium contains disarmed Ti and Ri plasmids that do not contain the oncogenes which cause tumorigenes is or rhizogenesis, respectively, which are used as the vectors and contain the genes of interest that are subsequently introduced into plants. Preferred strains would include but are not limited to Agrobacterium tumefaciens strain C58, a nopaline-type strain that is used to mediate the transfer of DNA into a plant cell, octopine-type strains such as LBA4404 or succinamopine-type strains e.g., EHA 101 or EHA105. The use of these strains for plant transformation has been reported and the methods are familiar to those of skill in the art.

Those of skill in the art are aware of the typical steps in the plant transformation process. The Agrobacterium can be prepared either by inoculating a liquid such as Luria Burtani (LB) media directly from a glycerol stock or streaking the Agrobacterium onto a solidified media from a glycerol stock, allowing the bacteria to grow under the appropriate selective conditions, generally from about 26-30° C., more preferably about 28° C., and taking a single colony from the plate and inoculating a liquid culture medium containing the selective agents. Alternatively a transfer loop or slurry of Agrobacterium can be taken from the plate and resuspended in liquid and used for inoculation. Those of skill in the art are familiar with procedures for growth and suitable culture conditions for Agrobacterium as well as subsequent inoculation procedures. The density of the Agrobacterium culture used for inoculation and the ratio of Agrobacterium cells to explant can vary from one system to the next, and therefore optimization of these parameters for any transformation method is expected.

Typically, an Agrobacterium culture is inoculated from a streaked plate or glycerol stock and is grown overnight, and the bacterial cells are washed and resuspended in a culture medium suitable for inoculation of the explant. Suitable inoculation media for the present invention include, but are not limited ½ strength MSPL (2.2 g/L GIBCO (Carlsbad, Calif.) MS salts, 2 mg/L glycine, 0.5 g/L niacin, 0.5 g/L L-pyridoxine-HCl, 0.1 mg/L thiamine, 115 g/L L-proline, 26 g/L D-glucose, 68.5 g/L sucrose, pH 5.4) or ½ strength MS VI (2.2 g/L GIBCO (Carlsbad, Calif.) MS salts, 2 mg/L glycine, 0.5 g/L niacin, 0.5 g/L L-pyridoxine-HCl, 0.1 mg/L thiamine, 115 g/L L-proline, 10 g/L D-glucose, and 10 g/L sucrose, pH 5.4). The inoculation media may be supplemented with a growth inhibiting agent (PCT Publication WO 01109302). The range and concentration of the growth inhibition agent can vary and depends of the agent and plant system. Growth inhibiting agents including, but not limited to, silver nitrate, silver thiosulfate, or carbenicillin are the preferred growth inhibition agents. The growth inhibiting agent is added in the amount necessary to achieve the desired effect. Silver nitrate is preferably used in the inoculation media at a concentration of about 1 µM (micromolar) to 1 mM (millimolar), more preferably 5 µM-100 µM. The concentration of carbenicillin used in the inoculation media is about 5 mg/L to 100 mg/L more preferably about 50 mg/L. A compound which induces *Agrobacterium* virulence genes such as acetosyringone can also be added to the inoculation medium.

In a preferred embodiment, the *Agrobacterium* used for inoculation are pre-induced in a medium such as a buffered media with appropriate salts containing acetosyringone, a carbohydrate, and selective antibiotics. In a preferred embodiment, the *Agrobacterium* cultures used for transformation are pre-induced by culturing at about 28° C. in AB-glucose minimal medium (Chilton et al., 1974; Lichtenstein and Draper, 1986) supplemented with acetosyringone at about 200 µM and glucose at about 2%. The concentration of selective antibiotics for *Agrobacterium* in the pre-induction medium is about half the concentration normally used in selection. The density of the *Agrobacterium* cells used is about $10^7$-$10^{10}$ cfu/mL of *Agrobacterium*. More preferably, the density of *Agrobacterium* cells used is about $5\times10^8$-$4\times10^9$ cfu/mL. Prior to inoculation the *Agrobacterium* can be washed in a suitable media such as ½ strength MS.

In a preferred embodiment, the floral dip method of transformation with *Agrobacterium* and the Ti plasmid was used as described in Example 4.

The next stage of the transformation process is the inoculation. In this stage the explants and *Agrobacterium* cell suspensions are mixed together. The mixture of *Agrobacterium* and explant(s) can also occur prior to or after a wounding step. By wounding as used herein is meant any method to disrupt the plant cells thereby allowing the *Agrobacterium* to interact with the plant cells. Those of skill in the art are aware of the numerous methods for wounding. These methods would include, but are not limited to, particle bombardment of plant tissues, sonicating, vacuum infiltrating, shearing, piercing, poking, cutting, or tearing plant tissues with a scalpel, needle or other device. The duration and condition of the inoculation and *Agrobacterium* cell density will vary depending on the plant transformation system. The inoculation is generally performed at a temperature of about 15° C.-30° C., preferably 23° C.-28° C. from less than one minute to about 3 hours. The inoculation can also be done using a vacuum infiltration system.

After inoculation, any excess *Agrobacterium* suspension can be removed and the *Agrobacterium* and target plant material are co-cultured. The co-culture refers to the time post-inoculation and prior to transfer to a delay or selection medium. Any number of plant tissue culture media can be used for the co-culture step. For the present invention, a reduced salt media such as half-strength MS-based co-culture media is used and the media lacks complex media additives including but not limited to undefined additives such as casein hydolysate, and B5 vitamins and organic additives. Plant tissues after inoculation with *Agrobacterium* can be cultured in a liquid media. More preferably, plant tissues after inoculation with *Agrobacterium* are cultured on a semi-solid culture medium solidified with a gelling agent such as agarose, more preferably a low EEO agarose. The co-culture duration is from about one hour to 72 hours, preferably less than 36 hours, more preferably about 6 hours to 35 hours. The co-culture media can contain one or more *Agrobacterium* growth inhibiting agent(s) or combination of growth inhibiting agents such as silver nitrate, silver thiosulfate, or carbenicillin. The concentration of silver nitrate or silver thiosulfate is preferably about 1 µM to 1 mM, more preferably about 5 µM to 100 µM, even more preferably about 10 µM to 50 µM, most preferably about 20 µM. The concentration of carbenicillin in the co-culture medium is preferably about 5 mg/L to 100 mg/L more preferably 10 mg/L to 50 mg/L, even more preferably about 50 mg/L. The co-culture is typically performed for about one to three days more preferably for less than 24 hours at a temperature of about 18° C.-30° C., more preferably about 23° C.-25° C. The co-culture can be performed in the light or in light-limiting conditions. Preferably, the co-culture is performed in light-limiting conditions. By light-limiting conditions as used herein is meant any conditions which limit light during the co-culture period including but not limited to covering a culture dish containing the plant/*Agrobacterium* mixture with a cloth, foil, or placing the culture dishes in a black bag, or placing the cultured cells in a dark room. Lighting conditions can be optimized for each plant system as is known to those of skill in the art.

After co-culture with *Agrobacterium*, the explants can be placed directly onto selective media. The explants can be sub-cultured onto selective media in successive steps or stages. For example, the first selective media can contain a low amount of selective agent, and the next sub-culture can contain a higher concentration of selective agent or vice versa. The explants can also be placed directly on a fixed concentration of selective agent. Alternatively, after co-culture with *Agrobacterium*, the explants can be placed on media without the selective agent. Those of skill in the art are aware of the numerous modifications in selective regimes, media, and growth conditions that can be varied depending on the plant system and the selective agent. In the preferred embodiment, after incubation on non-selective media containing the antibiotics to inhibit *Agrobacterium* growth without selective agents, the explants are cultured on selective growth media. Typical selective agents include but are not limited to antibiotics such as geneticin (G418), kanamycin, paromomycin, herbicides such as glyphosate or phosephinothericine, or other growth inhibitory compounds such as amino acid analogues, e.g., 5-methyltryptophan. Additional appropriate media components can be added to the selection or delay medium to inhibit *Agrobacterium* growth. Such media components can include, but are not limited to antibiotics such as carbenicillin or cefotaxime.

After the co-culture step, and preferably before the explants are placed on selective or delay media, cells can be analyzed for efficiency of DNA delivery by a transient assay that can be used to detect the presence of one or more gene(s) contained on the transformation vector, including, but not limited to a selectable marker gene such as the gene that encodes for β-glucuronidase (GUS). The total number of blue spots (indicating GUS expression) for a selected number of explants is used as a positive correlation of DNA transfer efficiency. The efficiency of T-DNA delivery and the effect of various culture condition manipulations on T-DNA delivery can be tested in transient analyses as described. A reduction in the T-DNA transfer process can result in a decrease in copy number and complexity of integration as complex integration patterns can originate from co-integration of separate T-DNAs (DeNeve et al., 1997). The effect of culture conditions of the target tissue can be tested by transient analyses and more preferably, in stably transformed plants. Any number of methods are suitable for plant analyses, including but not limited to, histochemical assays, biological assays, and molecular analyses.

After effecting delivery of exogenous DNA to recipient cells, the next steps generally concern identifying the transformed cells for further culturing and plant regeneration. As mentioned herein, in order to improve the ability to identify transformants, one may desire to employ a selectable marker gene as, or in addition to, the expressible gene of interest. In this case, one would then generally assay the potentially transformed cell population by exposing the cells to a selective agent or agents, or one would screen the cells for the desired marker gene trait.

Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchirniya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Ornirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without first producing protoplasts (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Publication WO 95/06128, specifically incorporated herein by reference in its entirety).

Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into a cell, a marker gene which confers resistance to some normally inhibitory agent, such as an antibiotic or herbicide. Examples of antibiotics which may be used include the aminoglycoside antibiotics neomycin, kanamycin, G418 and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA. Using the techniques disclosed herein, greater than 40% of bombarded embryos may yield transformants.

One example of an herbicide which is useful for selection of transformed cell lines in the practice of the invention is the broad spectrum herbicide glyphosate. Glyphosate inhibits the action of the enzyme EPSPS, which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, PCT Publication WO 97/04103. The best characterized mutant EPSPS gene conferring glyphosate resistance comprises amino acid changes at residues 102 and 106, although it is anticipated that other mutations will also be useful (PCT Publication WO 97/04103). Furthermore, a naturally occurring glyphosate resistant EPSPS may be used, e.g., the CP4 gene isolated from *Agrobacterium* encodes a glyphosate resistant EPSPS (U.S. Pat. No. 5,627,061).

To use the bar-bialaphos or the EPSPS-glyphosate selective systems, tissue is cultured for 0-28 days on nonselective medium and subsequently transferred to medium containing from 1-3 mg/L bialaphos or 1-3 mM glyphosate as appropriate. While ranges of 1-3 mg/L bialaphos or 1-3 mM glyphosate will typically be preferred, it is believed that ranges of 0.1-50 mg/L bialaphos or 0.1-50 mM glyphosate will find utility in the practice of the invention. Bialaphos and glyphosate are provided as examples of agents suitable for selection of transformants, but the technique of this invention is not limited to them.

Another herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

It further is contemplated that the herbicide dalapon, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; U.S. Pat. No. 5,780,708).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. Nos. 5,508,468 and 6,118,047. An example of a selectable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. In a similar fashion, the introduction of the C1 and B genes will result in pigmented cells and/or tissues.

The enzyme luciferase may be used as a selectable marker in the context of the present invention. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells that are expressing luciferase and manipulate cells expressing in real time. Another selectable marker which may be used in a similar fashion is the gene coding for green fluorescent protein (GFP) or a gene coding for other fluorescing proteins such as DsRed® (Clontech, Palo Alto, Calif.).

It further is contemplated that combinations of selectable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a selectable marker gene such as luciferase or GFP would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a selectable marker gene, for example, between an NPTII gene and a GFP gene (WO 99/60129).

Regeneration and Seed Production

Cells that survive the exposure to the selective agent, or cells that have been scored positive in a screening assay, may be cultured in media that supports regeneration of plants. In an exemplary embodiment, MS and N6 (Chu et al., 1975) media may be modified by including further substances such as growth regulators. Preferred growth regulators for plant regeneration include cytokinins such as 6-benzylamino purine, zeatin, kinetin, thidiazuron, diphenylurea or the like, and abscisic acid. Media improvement in these and like ways has been found to facilitate the growth of cells at specific developmental stages. Tissue may be maintained on a basic media with auxin type growth regulators until sufficient tissue is available to begin plant regeneration efforts, or following repeated rounds of manual selection, until the morphology of the tissue is suitable for regeneration, then transferred to media conducive to maturation of embryos. Cultures are transferred every 1-4 weeks, preferably every 2-3 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets were transferred to soil-free plant growth mix, and hardened off, e.g., in an environmentally controlled chamber at about 85% relative humidity, 600 ppm CO2, and 25-250 micromole photons m-2s-1 of light, prior to transfer to a greenhouse or growth chamber for maturation. Plants are preferably matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and plant tissue culture flasks. Regenerating plants are preferably grown at about 19 to 28° C. After the regenerating plants have reached the stage of shoot and root development, they may be transferred to a greenhouse for further growth and testing. Plants may be pollinated using conventional plant breeding methods known to those of skill in the art and seed produced.

Progeny may be recovered from transformed plants and tested for expression of the exogenous expressible gene. Note however, that seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with 10-5 M abscisic acid and then transferred to growth regulator-free medium for germination.

Characterization

To confirm the presence of the exogenous DNA or "transgene(s)" in the regenerating plants, a variety of assays, known in the art may be performed. Such assays include, for example, "molecular biological" assays, such as Southern and Northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

DNA Integration, RNA Expression and Inheritance

Genomic DNA may be isolated from callus cell lines or any plant parts to determine the presence of the exogenous gene through the use of techniques well known to those skilled in the art. Note, that intact sequences will not always be present, presumably due to rearrangement or deletion of sequences in the cell.

The presence of DNA elements introduced through the methods of this invention may be determined by polymerase chain reaction (PCR). Using this technique discreet ragments of DNA are amplified and detected by gel electrophoresis. This type of analysis permits one to determine whether a gene is present in a stable transformant, but does not necessarily prove integration of the introduced gene into the cell's genome. Typically, DNA has been integrated into the genome of all transformants that demonstrate the presence of the gene through PCR analysis. In addition, it is not possible using PCR techniques to determine whether transformants have exogenous genes introduced into different sites in the genome, i.e., whether transformants are of independent origin. Using PCR techniques it is possible to clone fragments of the host's genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition, it is possible through Southern hybridization to demonstrate the presence of introduced genes in high molecular weight DNA, i.e., confirm that the introduced gene has been integrated into the transformed cell's genome. The technique of Southern hybridization provides information that is obtained using PCR, e.g., the presence of a gene, but also demonstrates integration into the genome and characterizes each individual transformant.

It is contemplated that using the techniques of dot or slot blot hybridization, which are modifications of Southern hybridization techniques, one could obtain the same information that is derived from PCR, e.g., the presence of a gene.

Both PCR and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR techniques, referred to as RT-PCR, also may be used for detection and quantitation of RNA produced from introduced genes. In this application of PCR it is first necessary to reverse transcribe RNA into DNA, using enzymes such as reverse transcriptase, and then through the use of conventional PCR techniques amplify the DNA. In most instances PC techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

It is further contemplated that TAQMAN® technology (Applied Biosystems, Foster City, Calif.) may be used to quantitate both DNA and RNA in a transgenic cell.

Gene Expression

While Southern blotting and PCR may be used to detect the gene(s) in question, they do not provide information as to whether the gene is being expressed. Expression may be evaluated by specifically identifying the protein products of the introduced genes or evaluating the phenotypic changes brought about by their expression. Among the more common methods of determination of the expression of proteins is reverse transcriptase polymerase chain reaction (RT-PCR) and real-time RT-PCR. Both of these techniques enable one to determine message expression with well developed methods.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and 14C-acetyl CoA or for anthranilate synthase activity by following an increase in fluorescence as anthranilate is produced, to name two.

Very frequently the expression of a gene product is determined by evaluating the phenotypic results of its expression. These assays also may take many forms, including but not limited to, analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

Event Specific Transgene Assay

Southern blotting, PCR and RT-PCR techniques can be used to identify the presence or absence and expression of a given transgene but, depending upon experimental design, may not specifically and uniquely identify identical or related transgene constructs located at different insertion points within the recipient genome. To more precisely characterize the presence of transgenic material in a transformed plant, one skilled in the art could identify the point of insertion of the transgene and, using the sequence of the recipient genome flanking the transgene, develop an assay that specifically and uniquely identifies a particular insertion event. Many methods can be used to determine the point of insertion such as, but not limited to, Genome Walker™ technology (CLONTECH, Palo Alto, Calif.), Vectorette™ technology (Sigma, St. Louis, Mo.), restriction site oligonucleotide PCR (Sarkar et al., 1993; Weber et al., 1998), uneven PCR (Chen and Wu, 1997) and generation of genomic DNA clones containing the transgene of interest in a vector such as, but not limited to, lambda phage.

Once the sequence of the genomic DNA directly adjacent to the transgenic insert on either or both sides has been determined, one skilled in the art can develop an assay to specifically and uniquely identify the insertion event. For example, two oligonucleotide primers can be designed, one wholly contained within the transgene and one wholly contained within the flanking sequence, which can be used together with the PCR technique to generate a PCR product unique to the inserted transgene.

In one embodiment, the two oligonucleotide primers for use in PCR could be designed such that one primer is complementary to sequences in both the transgene and adjacent flanking sequence such that the primer spans the junction of the insertion site while the second primer could be homologous to sequences contained wholly within the transgene. In another embodiment, the two oligonucleotide primers for use in PCR could be designed such that one primer is complementary to sequences in both the transgene and adjacent flanking sequence such that the primer spans the junction of the insertion site while the second primer could be homologous to sequences contained wholly within the genomic sequence adjacent to the insertion site. Confirmation of the PCR reaction may be monitored by, but not limited to, size analysis on gel electrophoresis, sequence analysis, hybridization of the PCR product to a specific radiolabeled DNA or RNA probe or to a molecular beacon (Tyagi and Kramer, 1996), or use of the primers in conjugation with a TAQMAN™ probe and technology (Applied Biosystems, Foster City, Calif.).

Site Specific Integration or Excision of Transgenes

It is specifically contemplated by the inventors that one could employ techniques for the site-specific integration or excision of transformation constructs prepared in accordance with the instant invention. An advantage of site-specific integration or excision is that it can be used to overcome problems associated with conventional transformation techniques, in which transformation constructs typically randomly integrate into a host genome and multiple copies of a construct may integrate. This random insertion of introduced DNA into the genome of the targeted cells can be detrimental to the cell if the foreign DNA inserts into an essential gene. In addition, the expression of a transgene may be influenced by "position effects" caused by the surrounding genomic DNA. Further, because of difficulties associated with plants possessing multiple transgene copies, including gene silencing, recombination and unpredictable inheritance, it is typically desirable to control the copy number of the inserted DNA, often only desiring the insertion of a single copy of the DNA sequence.

Site-specific integration can be achieved in plants by means of homologous recombination (see, for example, U.S. Pat. No. 5,527,695, specifically incorporated herein by reference in its entirety). Homologous recombination is a reaction between any pair of DNA sequences having a similar sequence of nucleotides, where the two sequences interact (recombine) to form a new recombinant DNA species. The frequency of homologous recombination increases as the length of the shared nucleotide DNA sequences increases, and is higher with linearized plasmid molecules than with circularized plasmid molecules. Homologous recombination can occur between two DNA sequences that are less than identical, but the recombination frequency declines as the divergence between the two sequences increases.

Introduced DNA sequences can be targeted via homologous recombination by linking a DNA molecule of interest to sequences sharing homology with endogenous sequences of the targeted cell. Once the DNA enters the cell, the two homologous sequences can interact to insert the introduced DNA at the site where the homologous genomic DNA sequences were located. Therefore, the choice of homologous sequences contained on the introduced DNA will determine the site where the introduced DNA is integrated via homologous recombination. For example, if the DNA sequence of interest is linked to DNA sequences sharing homology to a single copy gene of a host plant cell, the DNA sequence of interest will be inserted via homologous recombination at only that single specific site. However, if the DNA sequence of interest is linked to DNA sequences sharing homology to a multicopy gene of the host eukaryotic cell, then the DNA sequence of interest can be inserted via homologous recombination at each of the specific sites where a copy of the gene is located.

DNA can be inserted into the host genome by a homologous recombination reaction involving either a single reciprocal recombination (resulting in the insertion of the entire length of the introduced DNA) or through a double reciprocal recombination (resulting in the insertion of only the DNA located between the two recombination events). For example, if one wishes to insert a foreign gene into the genomic site where a selected gene is located, the introduced DNA should contain sequences homologous to the selected gene. A single homologous recombination event would then result in the entire introduced DNA sequence being inserted into the selected gene. Alternatively, a double recombination event can be achieved by flanking each end of the DNA sequence of interest (the sequence intended to be inserted into the genome) with DNA sequences homologous to the selected gene. A homologous recombination event involving each of the homologous flanking regions will result in the insertion of the foreign DNA. Thus only those DNA sequences located between the two regions sharing genomic homology become integrated into the genome.

Although introduced sequences can be targeted for insertion into a specific genomic site via homologous recombination, in higher eukaryotes homologous recombination is a relatively rare event compared to random insertion events. Thus random integration of transgenes is more common in plants. To maintain control over the copy number and the location of the inserted DNA, randomly inserted DNA sequences can be removed. One manner of removing these random insertions is to utilize a site-specific recombinase system (U.S. Pat. No. 5,527,695).

A number of different site specific recombinase systems could be employed in accordance with the instant invention, including, but not limited to, the Cre/lox system of bacteriophage P1 (U.S. Pat. No. 5,658,772, specifically incorporated herein by reference in its entirety), the FLP/FRT system of yeast (Golie and Lindquist, 1989), the Gin recombinase of phage Mu (Maeser et al., 1991), the Pin recombinase of E. coli (Enomoto et al., 1983}, and the R/RS system of the pSR1 plasmid (Araki et al., 1992). The bacteriophage P1 Cre/lox and the yeast FLP/FRT systems constitute two particularly useful systems for site specific integration or excision of transgenes. In these systems, a recombinase (Cre or FLP) will interact specifically with its respective site-specific recombination sequence (lox or FRT, respectively) to invert or excise the intervening sequences.

The sequence for each of these two systems is relatively short (34 bp for lox and 47 bp for FRT) and therefore, convenient for use with transformation vectors.

The FLP/FRT recombinase system has been demonstrated to function efficiently in plant cells. Experiments on the performance of the FLP/FRT system in both maize and rice protoplasts indicate that FRT site structure, and amount of the FLP protein present, affects excision activity. In general, short incomplete FRT sites leads to higher accumulation of excision products than the complete full-length FRT sites. The systems can catalyze both intra- and intermolecular reactions in maize protoplasts, indicating its utility for DNA excision as well as integration reactions. The recombination reaction is reversible and this reversibility can compromise the efficiency of the reaction in each direction. Altering the structure of the site-specific recombination sequences is one approach to remedying this situation. The site-specific recombination sequence can be mutated in a manner that the product of the recombination reaction is no longer recognized as a substrate for the reverse reaction, thereby stabilizing the integration or excision event.

In the Cre-lox system, discovered in bacteriophage Pl, recombination between lox sites occurs in the presence of the Cre recombinase (see, e.g., U.S. Pat. No. 5,658,772, specifically incorporated herein by reference in its entirety). This system has been utilized to excise a gene located between two lox sites which had been introduced into a yeast genome (Sauer, 1987). Cre was expressed from an inducible yeast GAL1 promoter and this Cre gene was located on an autonomously replicating yeast vector.

Since the lox site is an asymmetrical nucleotide sequence, lox sites on the same DNA molecule can have the same or opposite orientation with respect to each other. Recombination between lox sites in the same orientation results in a deletion of the DNA segment located between the two lox sites and a connection between the resulting ends of the original DNA molecule. The deleted DNA segment forms a circular molecule of DNA. The original DNA molecule and the resulting circular molecule each contain a single lox site. Recombination between lox sites in opposite orientations on the same DNA molecule result in an inversion of the nucleotide sequence of the DNA segment located between the two lox sites. In addition, reciprocal exchange of DNA segments proximate to lox sites located on two different DNA molecules can occur. All of these recombination events are catalyzed by the product of the Cre coding region.

Deletion of Sequences Located within the Transgenic Insert

During the transformation process it is often necessary to include ancillary sequences, such as selectable marker or reporter genes, for tracking the presence or absence of a desired trait gene transformed into the plant on the DNA construct. Such ancillary sequences often do not contribute to the desired trait or characteristic conferred by the phenotypic trait gene. Homologous recombination is a method by which introduced sequences may be selectively deleted in transgenic plants.

It is known that homologous recombination results in genetic rearrangements of transgenes in plants. Repeated DNA sequences have been shown to lead to deletion of a flanked sequence in various dicot species, e.g. *Arabidopsis thaliana* (Swoboda et al., 1994; Jelesko et al., 1999), *Brassica napus* (Gal et al., 1991; Swoboda et al, 1993) and *Nicotiana tabacum* (Peterhans et al., 1990; Zubko et al., 2000). One of the most widely held models for homologous recombination is the double-strand break repair (DSBR) model (Szostak et al., 1983).

Deletion of sequences by homologous recombination relies upon directly repeated DNA sequences positioned about the region to be excised in which the repeated DNA sequences direct excision utilizing native cellular recombination mechanisms. The first fertile transgenic plants are crossed to produce either hybrid or inbred progeny plants, and from those progeny plants, one or more second fertile transgenic plants are selected which contain a second DNA sequence that has been altered by recombination, preferably resulting in the deletion of the ancillary sequence. The first fertile plant can be either hemizygous or homozygous for the DNA sequence containing the directly repeated DNA that will drive the recombination event. The directly repeated sequences are located 5' and 3' to the target sequence in the transgene. As a result of the recombination event, the transgene target sequence may be deleted, amplified or otherwise modified within the plant genome. In the preferred embodiment, a deletion of the target sequence flanked by the directly repeated sequence will result.

Alternatively, directly repeated DNA sequence mediated alterations of transgene insertions may be produced in somatic cells. Preferably, recombination occurs in a cultured cell, e.g., callus, and may be selected based on deletion of a negative selectable marker gene, e.g., the periA gene isolated from *Burkholderia caryolphilli* that encodes a phosphonate ester hydrolase enzyme that catalyzes the hydrolysis of glyceryl glyphosate to the toxic compound glyphosate (U.S. Pat. No. 5,254,801).

Breeding Plants of the Invention

In addition to direct transformation of a particular plant genotype with a construct prepared according to the current invention, transgenic plants may be made by crossing a plant having a construct of the invention to a second plant lacking the construct. For example, a selected coding region operably linked to a promoter can be introduced into a particular plant variety by crossing, without the need for ever directly transforming a plant of that given variety. Therefore, the current invention not only encompasses a plant directly regenerated from cells which have been transformed in accordance with the current invention, but also the progeny of such plants. As used herein the term "progeny" denotes the offspring of any generation of a parent plant prepared in accordance with the instant invention, wherein the progeny comprises a construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention.

To achieve this one could, for example, perform the following steps: plant seeds of the first (starting line) and second (donor plant line that comprises a transgene of the invention) parent plants; grow the seeds of the first and second parent plants into plants that bear flowers; pollinate a flower from the first parent plant with pollen from the second parent plant; and harvest seeds produced on the parent plant bearing the fertilized flower.

Backcrossing is herein defined as the process including the steps of crossing a plant of a first genotype containing a desired gene, DNA sequence or element to a plant of a second genotype lacking the desired gene, DNA sequence or element; selecting one or more progeny plant containing the desired gene, DNA sequence or element; crossing the progeny plant to a plant of the second genotype; repeating steps (b) and (c) for the purpose of transferring the desired gene, DNA sequence or element from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

Using a variety of methods exemplary embodiments of the invention are directed at improving the non-destructive extraction of hydrophobic materials from cells. This is particularly applicable to improved performance in higher plants, with special focus on crop plants and with additional focus on plants with large storage sinks such as seeds and other carbon storage tissues (e.g., potato, cassava, and sweet potato).

EXAMPLES

Certain embodiments of the invention will not be described in more detail through the following examples. The examples are intended solely to aid in more fully describing selected embodiments of the invention, and should not be considered to limit the scope of the invention in any way.

Example 1—Transformation of *Arabidopsis*

The constructs produced for modulation of the antenna complex of *Arabidopsis* were transformed into the plants using protocols developed by Bechtold and colleagues (Bechtold et al., 1993) and Clough and Bent (Clough and Bent, 1998). Briefly we grew *Arabidopsis* plants until they are flowering. An *Agrobacterium tumefaciens* strain (for example, LBA4004) carrying gene of interest on a binary vector were prepared. A large overnight liquid culture was grown @ 28-30° C. in LB with selection antibiotic to select for the binary plasmid. The *Agrobacterium*, was spun down and resuspend to A600=1 in a 5% Sucrose solution (if made fresh, no need to autoclave) in half-strength Murashige & Skoog (MS) medium. Before dipping, Silwet L-77 was added to a concentration of 0.05% (500 µL/L) and mixed well. The above-ground parts of plant were dipped in *Agrobacterium* solution for 5 minutes. The dipped plants were placed under a dark dome or cover overnight to maintain high humidity (plants were laid on their side if necessary). Continued to grow plants normally. The dry seed was harvested and selected for transformants using PCR.

Example 2—*Camelina* Transformation Procedure

The constructs produced for modulation of the antenna complex of *Arabidopsis* were transformed into the plants using protocols developed by Lu and Kang (Lu and Kang, 2008). Grew *Camelina* plants until they are flowering. *Agrobacterium tumefaciens* strain LBA4004 carrying gene of interest on a binary vector were prepared. A large overnight liquid culture was grown @ 28-30° C. in LB with selection antibiotic to select for the binary plasmid. *Agrobacterium* was spun down, resuspended to A600=1 in 5% Sucrose solution (if made fresh, no need to autoclave) in half-strength MS. Silwet L-77 was added before dipping, to a concentration of 0.05% (500 µL/L) and mixed well. A beaker with resuspended Agrobacteria culture was placed in a 310 mm high vacuum desiccator. One to two *Camelina* plants were put into the desiccator. The plants were bent carefully so they fit in a desiccator and placed flowering part into the liquid culture. A vacuum was applied to reduce the atmospheric pressure by about 95%. After 5 minutes, treated plants were placed under a dark dome or cover overnight to maintain high humidity (plants can be laid on their side if necessary) and continued to grow plants normally. Harvested dry seed and select for transformants.

Example 3—Production of Constructs for Transformation of *Camelina*

A fragment of the *Camelina* satina Cao gene was cloned using RT-PCR with total RNA isolated from *Camelina* leaves as a template. Primers were based on the *Arabidopsis* Cao gene's sequence.

Based on the obtained sequence, 2 different vectors were constructed and inserted into modified pCambia1301 plasmid carrying bacterial kanamycin resistance (kan) and plant hygromycin (hptII) resistance genes. The schematic representation of the vectors is in FIG. 4A-B. The pCambia1301CAOiShort vector (pCambria1301NFCAORNAiS) contains 272 bp of *Camelina* Cao sequence, followed by an intron from *Arabidopsis* Cao and a reverse complement of the *Camelina* sequence. The pCAmbia1301CAOiLong (pCambia1301NFCAORNAiL) contained 750 bp of *Camelina* Cao sequence, 2 *Arabidopsis* introns and the reverse complement of the *Camelina* sequence. In this vector the Cao gene was under the control of leaf-specific CAB1 promoter. The construct was made such that a genomic sense/antisense region spanned the first 2 exons of CAO genes with introns from *A. thaliana* under the control of leaf-specific CAB1 promoter was used to generate a CAO RNAi plasmid on basis of pCambia1301 plasmid carrying bacterial kanamycin resistance (kan) and plant hygromycin (hptII) resistance genes. The pCambia1301CAOiShort vector (pCambria1301NFCAORNAiS) contained 272 bp of the *Camelina* Cao sequence, followed by an intron from the *Arabidopsis* Cao gene and a reverse complement of the *Camelina* sequence. The pCambia1301CAOiLong (pCambia1301NFCAORNAiL; FIG. 4A top) contained 750 bp of *Camelina* Cao sequence, 2 *Arabidopsis* introns and the reverse complement of the *Camelina* sequence. Transformation of the Suneson line of *Camelina sativa* with the pCambia1301CAOiShort or pCambia1301CAOiLong vector resulted in Cao gene knock down transgenic plants.

The mutants were initially screened based on resistance to hygromycin. The putative transformants were then confirmed by PCR analysis to contain the correct sequences.

The reduced antenna sizes were confirmed by the following methods: Reduced fluorescence of the transgenic plants (FIGS. 8A-D) and blue native green gel analysis (FIG. 10) demonstrated the reduction in Photosystem II supercomplexes (the antenna size).

Example 4. Transformation of the *Arabidopsis* Chlorina Line Using the Floral Dip Method For transformation the *Arabidopsis chlorina* line Chl-3 was utilized. This Chl-3 line was generated by X-ray induced mutagenesis in CAO (Chlorophyll A Oxygenase) and was obtained from the *Arabidopsis* Biological Resource Center at Ohio State University.

A simplified *Arabidopsis* transformation protocol developed by Steve Clough and Andrew Bent (1998) from the University of Illinois, Urbana-Champaign was used for this procedure. This is described below as performed for this transformation.

1. Grew healthy *Arabidopsis* plants until they are flowering. Clipped bolts to encourage proliferation of many secondary bolts.
2. Prepared *Agrobacterium tumefaciens* strain carrying gene of interest on a binary vector. Grow a large liquid culture at 28 C in Luria-Bertani (LB) broth with antibiotics to select for the binary plasmid.
3. Spun down *Agrobacterium*, resuspend to A600=0.8-1.0 in Murashige and Skoog (MS) with 5% Sucrose.
4. Added Silwet L-77 (siloxane polyalkyleneoxide copolymer; a surfactant) to a concentration of 0.05% and mixed well.
5. Dipped inflorescences from the plant in *Agrobacterium* solution and leave for 5 minutes.
6. Place dipped plants in dark, and covered with a dome to maintain high humidity for 16-24 hours.
7. Returned transformed plants to normal growth conditions. Grew plants for 2-3 weeks, until the siliques are ripe and ready for harvesting.
8. Selected for transformants using fluorescence or antibiotic marker.

Vector construction—The plasmid for siRNA-mediated silencing of the chlorophillide a oxygenase (Cao) gene (pB110-CAO-NAB1-cab-nos) was constructed using a genomic sense/cDNA anti-sense strategy. Referring now to FIG. 15, a construct for transformation of *Arabidopsis* to generate a line as described in Example 4 is illustrated. Physical map of pb110-CAO-NAB-cab-nos *Agrobacterium* Ti-plasmid is identified. Pb110 backbone was used to harbor an *Arabidopsis* CAO gene with a *Chlamydomonas* LRE (Light Responsive Element) fused to the 5' end of an *Arabidopsis* Cao gene driven by the native CAO-promoter (CAO-pro) and CAO-terminator (CAO-term); as well as NAB1 gene (from *Chlamydomonas*) driven by light-sensitive cab-promoter and nos-terminator). The notation LB/RB T-DNA indications left/right border. The LRE (5'-GCCA-GACCCCCGC-3') (SEQ. ID. 27) serves as binding site for NAB 1 to allow light inducible control of expression

Example 5. Engineering *Camelina* Plants Using siRNA to Reduce the Chl b Level Through Modulation of the Cao Gene The background plant line used was *Camelina* line Suneson having knockout Cao genes. Since the sequence of the *C. sativa* Cao gene was unknown, primers homologous to *A. thaliana* cao sequence were used to amplify the *C. sativa* Cao gene, *C. sativa* cDNA made from total RNA with qScript and the following forward (ATGAACGCCGCCGT-GTTTAGT) (SEQ ID NO 28) and reverse (CGGTTCA-GCGCAATGTCTCCA) (SEQ ID NO 29) were used for this PCR. The resulting PCR product was cloned by the TA blunt cloning kit and six variants of the Cao gene were sequenced. The resulting sequences were used to design and synthesize the siRNA cassette under control of CAB1 leaf-specific promoter, which was placed in a modified pCambia1301 vector using EcoRI and HindIII restriction sites. FIG. 4 provides the details for the constructs used to transform the *C. sativa* line.

Generation and Screening of CAO siRNA Transgenic Lines—

For the generation of CAO siRNA lines, *C. sativa* (line Suneson) was transformed using the vacuum infiltration floral dip method. The transformed plants were grown to maturity and the resulting seeds were screened on MS media. Agar plates supplemented with 25 µg/ml hygromycin as selection agent. The hygromycin resistant seedlings were transferred to soil. To determine the presence of the siRNA sequence, the total plant DNA was extracted using a Qiagen kit and used as a PCR template. The presence of the transgene was confirmed by PCR using forward (5') and reverse (3") primers which hybridizes to the Cab 1 promoter and Nos teminator sequences, respectively. The T3 or above generation plants grown in controlled greenhouse conditions were used for subsequent experiments.

Chlorophyll Determination—

For chlorophyll a and b concentration determination, approximately 5 mm2 leaf disks were excised and homogenized in 1 ml of 80% acetone using a beat beater. The samples were spun down in a microfuge at maximum speed for 3 mins and the supernatants were used to determine chlorophyll concentrations according to Arnon equations (Arnon, 1949).

Chlorophyll Fluorescence Measurements—

Chlorophyll a fluorescence was measured on detached leaves placed on wet filter paper using Handy FluorCam FC 1000-H (Photon Systems, Drasov, Chech Republic). Leaves were dark-adapted for 20 min and the minimal fluorescence (Fo) determined with low intensity measuring light pulses (620 nm). Then a 0.8 second (s) saturating pulse of white light (4000 mmol photons m-2 s-1) was applied to determine the maximum fluorescence in a dark-adapted state (Fm). The leaves were then exposed to 300 s of 500 umol m-2 s-1 actinic white light, followed by 300 s of dark relaxation. The maximum fluorescence in light-adapted state (Fm'), was determined using a series of 0.8 s pulses of saturating white light. NPQ values were calculated as (Fm−Fm')/Fm'.

Isolation of Thylakoid Membranes—

Isolation of thylakoid membranes was carried out according to (Jarvi, S., Suorsa, M., Paakkarinen, V. & Aro, E. M. Optimized native gel systems for separation of thylakoid protein complexes: novel super- and mega-complexes. The Biochemical Journal 439, 207-214 (2011).), with slight modifications. All steps were carried out in the dark at 4° C. Fresh *Camelina* leaves were ground in a blender with ice cold grinding buffer (50 mM Hepes/KOH (pH 7.5), 330 mM sorbitol, 2 mM EDTA, 1 mM MgCl2, 5 mM ascorbate and 0.05% BSA) and filtered through 2 layers of Miracloth. The suspension was briefly centrifuged at 500 g at 4° C. for 30 sec. The supernatant was centrifuged for at 10000 g for 10 min. The pellet was resuspended in a Shock Buffer (50 mM Hepes/KOH (pH 7.5), 5 mM sorbitol and 5 mM MgCl2) followed by centrifugation at 10000 g at 4° C. for 10 min. Remnants of the Shock Buffer were removed by suspending the pellet into Storage Buffer (50 mM Hepes/KOH (pH 7.5), 100 mM sorbitol and 10 mM MgCl2) followed by centrifugation at 10000 g for 10 min. Finally, the thylakoid pellet was suspended into a small aliquot of storage buffer. The chlorophyll concentration was determined in aqueous 80% acetone according to Arnon, D. I. Copper Enzymes in Isolated Chloroplasts. Polyphenoloxidase in Beta Vulgaris. Plant physiology 24, 1-15 (1949).

Photosynthesis Rate Determination—

Gas-exchange measurements were performed with a LI-6400 open-flow gas exchange system (Li-Cor). Photosynthetic light response curves were produced by increasing light intensity from 0 to 2000 µmol photons m-2 s-1. The reference CO2 concentration was set at 400 µmol CO2 mol-1 air. The leaf temperature was kept the 25° C. and relative humidity at 50%. The measurements were done on fully opened leaves (leaves 8-10 from the bottom) of plants that were 3.5 weeks old.

Blue-Native Gel Electrophoresis—

Thylakoids containing 8 μg of chlorophyll were solubilized for 5 min by addition of equal volume of buffer containing α-dodecyl-maltoside at a 2% w/v concentration. A 1/10th volume of sample buffer containing Serva-Blue G was added and the sample was centrifuged in a microfuge for 10 min at maximum speed. Thylakoid complexes were resolved for 6 hours at 4° C. on 4-12% Tris Tricine gel using the Novex minigel system with a constant current of 6 mA.

Electron Microscopy—

*Camelina sativa* leaves were collected at age 3 weeks and fixed in cacodylate buffer containing 2.5% glutaraldehyde. Post-fixation, embedding and sectioning were done as previously described (Rieder and Cassels, 1999). The 100 nm think sections were imaged at Phillips/FEI T-12 microscope at 80 kV (sectioning and imaging were performed by Electron Microscopy Core of Vanderbilt University, Nashville, Tenn.). ImageJ was used to measure thickness of thylakoid membranes and lumen. Five chloroplast sections were used for analysis for each sample for thylakoid membrane measurements, and fifteen chloroplast sections per sample were used for starch granules count.

Light Transmittance Through Leaves—

Light transmission through the leaves between wavelengths 400 nm and 700 nm was determined with BLACK-Comet CXR-SR-50 spectrometer (StellarNet Inc.). Full sunlight at midday was used as a light source. The experiment was repeated in triplicate.

Figure 16A:
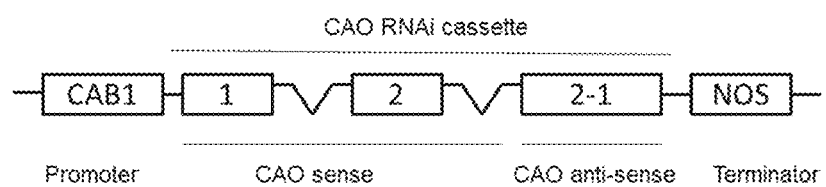
FIG. 16A is a schematic representation of the gene construct used to induce siRNA silencing of the CAO genes in C. sativa.
Figure 16B:
FIG. 16B is a comparison of growth phenotypes of 3-week old wild type and transgenic plants.
Figure 16C:
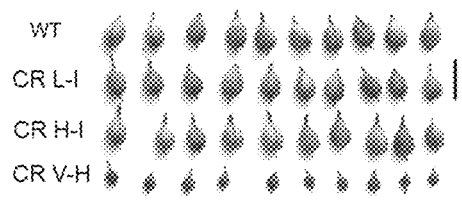
FIG. 16C is a comparison of fully developed pod size in WT, CR L-I, CR H-I and CR V-H lines. The pod development in CR H-I and CR V-H lines is not compromised, while CR V-H pods are much smaller at maturity. Scale bar, 1 cm.

In FIG. 16A-C it can be seen that the degree of Chl b reduction determines plant phenotype. FIG. 16A represents a schematic representation of the gene construct used to induce siRNA silencing of the CAO genes in *C. sativa*. Exons are represented by boxes and introns by "V" s. FIG. 16B provides a comparison of growth phenotypes of 3-week old wild type and transgenic plants. Plants with low-intermediate antenna size (CR L-I) corresponding to Chl a/b ratios of 4-5 have more vigorous growth compared to both wild type (WT) and plants with high-intermediate (CR H-I, Chl a/b ratios 6-9) and very high (CR V-H, Chl a/b ratios above 10). Scale bar, 10 cm. FIG. 16C provides a comparison of fully developed pod size in WT, CR L-I, CR H-I and CR V-H lines. The pod development in CR H-I and CR V-H lines is not compromised, while CR V-H pods are much smaller at maturity. Scale bar, 1 cm.

Transgenic Plants Demonstrate a Range of Phenotypes Based on the Degree of Chl b Reduction Since *C. sativa* is an allohexaploid plant, all the variants of the Cao gene were cloned and sequenced to ascertain that their sequences were similar enough to be targeted with a single siRNA construct. A genomic sense/antisense construct spanning the first 2 exons of Cao genes with introns from *A. thaliana* under the control of leaf-specific CAB1 promoter was used to generate a CAO siRNA plasmid. *C. sativa* plants were transformed by the floral dip method using vacuum infiltration and screened for resistance to hygromycin. Hygromycin-resistant T1 plants were planted and screened for reduced Chl a/b ratios. The Chl a/b ratios varied from 4 to 19. For subsequent experiments, CAO-siRNA lines (>T3 generation) were chosen covering a wide range of Chl a/b ratios and antenna sizes in order to demonstrate the dependence of plant performance on the degree of antenna reduction.

The transgenic plants were assigned to three different groups, according to their Chl a/b ratios and growth phenotypes: Chl a/b ratios low-intermediate "CR L-I" (chl a/b=4-5), Chl a/b ratio high-intermediate "CR H-I" (chl a/b=6-8), and Chl a/b ratio very high "CR V-H" chl a/b=9 and above. Representative phenotypes for each group are shown in FIG. 16.

CR L-I Plants with Moderate Reduction in Antenna Size have Increased Photosynthetic Rates The phenotypical characteristics of the transgenic lines were correlated with their photosynthesis rates. Specifically, the dependence of the CO2 fixation rate on light intensity in *C. sativa* plants grown under controlled greenhouse conditions were measured. Compared to WT, in CR H-I transgenics the photosynthesis rate was reduced by 10-15% at all light intensity ranges. In the CR V-H transgenics, the photosynthetic rate was severely impaired consistent with their stunted growth pattern. Not surprisingly, there was also a slight reduction of the photosynthetic rate in the best performing CR L-I line at low light intensity. This is an expected result in truncated antenna plants under light-limiting conditions, where the photochemistry is not saturated. Importantly, however, under high light conditions, the real photosynthesis rate in this line was 17% greater than in WT.

CR-LI Plants have Robust NPQ, Further Reduction in Antenna Size Impairs NPQ

CR transgenic plants with reduced antenna sizes were still able to perform efficient non-photochemical quenching (NPQ). NPQ collectively refers to a number of mechanisms of energy dissipation, which reduce the formation of damaging reactive oxygen species generated under condition of excess light when photochemistry is saturated. Mutants lacking Chl b, LHCII proteins, or exhibiting alterations in the topological organization of PSII antenna are known to undergo a strong reduction in NPQ, demonstrating the intricate involvement of antenna proteins in its activation Kovacs, L. et al. Lack of the light-harvesting complex CP24 affects the structure and function of the grana membranes of higher plant chloroplasts. The Plant cell 18, 3106-3120 (2006); de Bianchi, S., Dall'Osto, L., Tognon, G., Morosinotto, T. & Bassi, R. Minor antenna proteins CP24 and CP26 affect the interactions between photosystem II subunits and the electron transport rate in grana membranes of *Arabidopsis*. The Plant cell 20, 1012-1028 (2008).

There are several known components of NPQ. The fastest component, qE, typically develops within seconds to minutes of high light exposure. There is evidence that there are at least two different quenching mechanisms contributing to qE, both dependent on the buildup of the trans-membrane proton gradient: 1) the zeathanthin (Zea) dependent NPQ associated with deoxidation of violaxanthin via xanthophyll cycle and 2) PsbS-dependent mechanism that acts on LHCII antenna complexes resulting in functionally detached antennas and a rapid and reversible change in the organization of grana membranes Betterle, N. et al. Light-induced dissociation of an antenna hetero-oligomer is needed for non-photochemical quenching induction. The Journal of Biological Chemistry 284, 15255-15266 (2009).

Figure 17A:
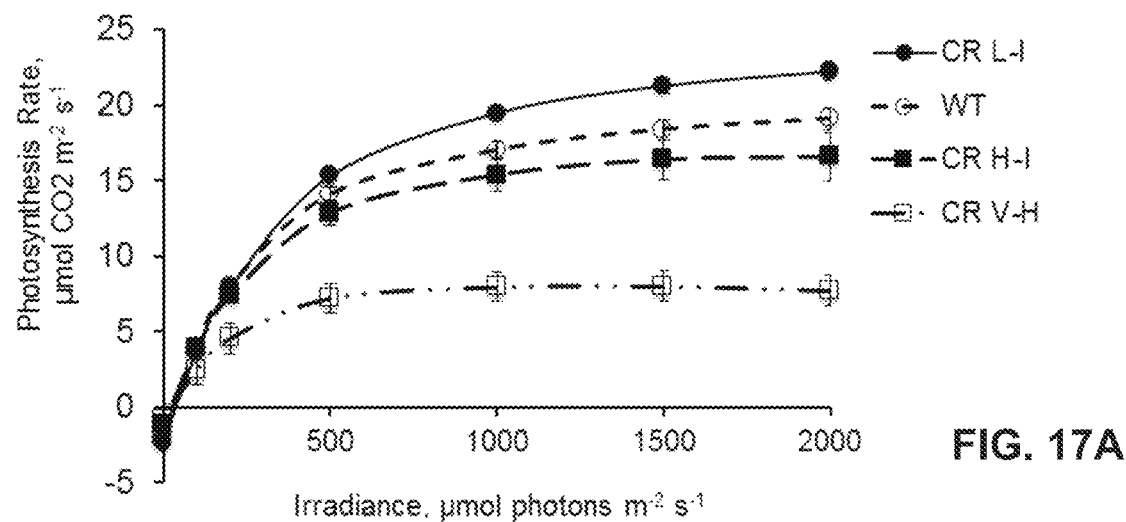
FIG. 17A is Photosynthesis light saturation response curves of WT, CR L-I, CR H-I and CR V-H.
Figure 17B:
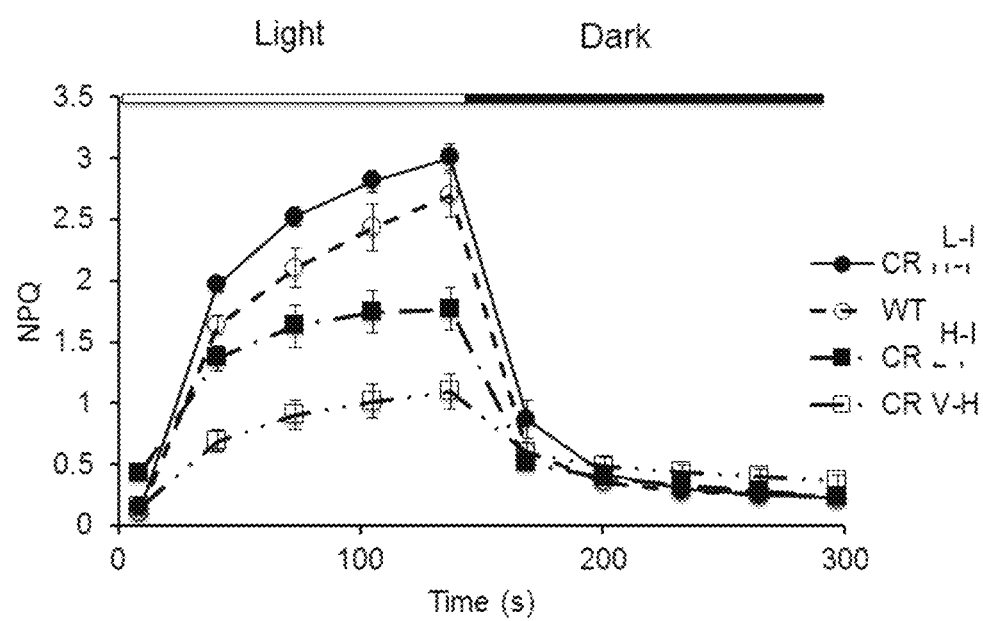
FIG. 17B is Non-photochemical quenching (NPQ) in WT, CR L-I, CR H-I and CR V-H. Leaves were exposed to 150 s of actinic light (800 mol photons m-2 s-1; white bar) followed by 150 s of dark relaxation (black bar).

NPQ in dark-adapted WT and CR mutant plants was compared. The actinic light intensity of 800 μmol m-2 s-1 was used to maximize the qE, while minimizing the photoinhibition. Measurements showed that the NPQ formation in the transgenics tracked the level of Chl b reduction. Compared to WT, NPQ was 15% higher in the CR L-I line and correspondingly reduced in CR H-I and CRV-H (FIG. 17B). Referring now to FIG. 17A is Photosynthesis light saturation response curves of WT, CR L-I, CR H-I and CR V-H. All experiments were performed on 3.5 week-old plants. Results are the average and ±SE of at least 5 independent experiments. FIG. 17B is non-photochemical quenching (NPQ) in in WT, CR L-I, CR H-I and CR V-H. Leaves were exposed to 150 s of actinic light (800 μmol photons m-2 s-1; white bar) followed by 150 s of dark relaxation (black bar). Results are the average and ±SE of 10 independent measurements.

FIG. 18A-M—

Comparison of thylakoid structure and PSII complex composition of WT and CR transgenics. FIG. 18A through FIG. 18H represent—Electron micrographs of thylakoid membranes from the wild type and CR lines obtained by transmission electron microscopy. Leaves from 3-week-old wild-type and CR L-I, CR H-I, and CR V-H plants were directly fixed 3 h after the start of the light phase of the growth photoperiod and prepared for transmission electron microscopy. Chloroplast sections are shown for the wild type FIG. 18A-FIG. 18E, CR L-I (FIG. 18B-FIG. 18F), CR H-I (FIG. 18C-FIG. 18G), and CR V-H (FIG. 18D-FIG. 18H) plants. Bars in the top and bottom panels are 50 and 100 nm in length, respectively.

Figure 18A:
FIG. 18A-M provides a comparison of thylakoid structure and PSII complex composition of WT and CR transgenics. Panels a through h represent—Electron micrographs of thylakoid membranes from the wild type and CR lines obtained by transmission electron microscopy. Leaves from 3-week-old wild-type and CR L-I, CR H-I, and CR V-H plants were directly fixed 3 h after the start of the light phase of the growth photoperiod and prepared for transmission electron microscopy. Chloroplast sections are shown for the wild type (a & e), CR L-I (b & f), CR H-I (c & g), and CR V-H (d & h) plants. Bars in the top and bottom panels are 50 and 100 nm in length, respectively.
Figure 18B:
Figure 18C:
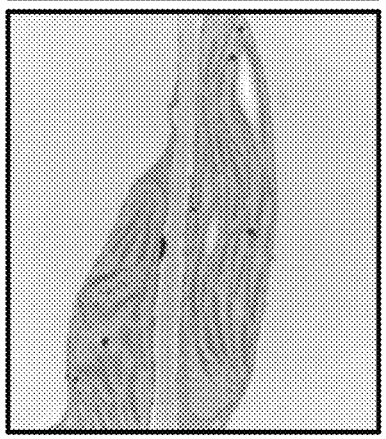
Figure 18D:
Figure 18E:
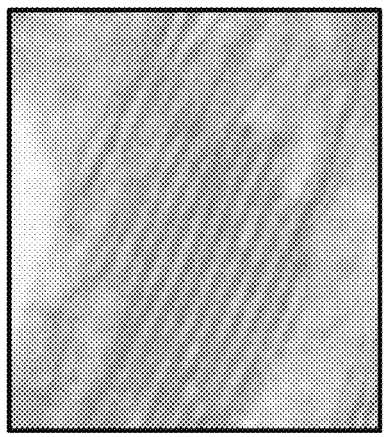
Figure 18F:
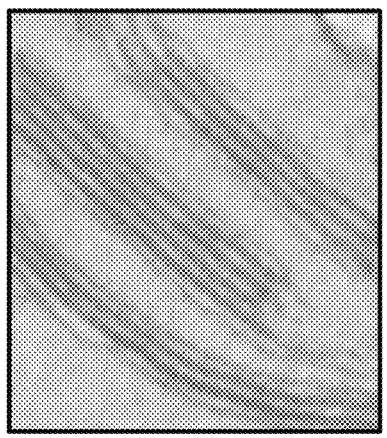
Figure 18G:
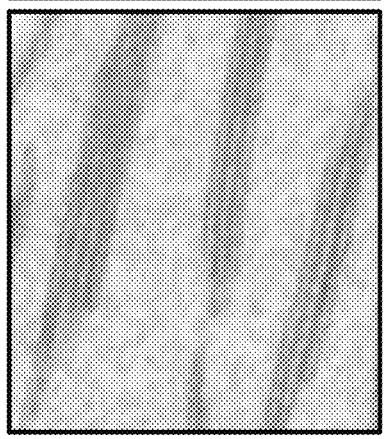
Figure 18H:
Figure 18I:
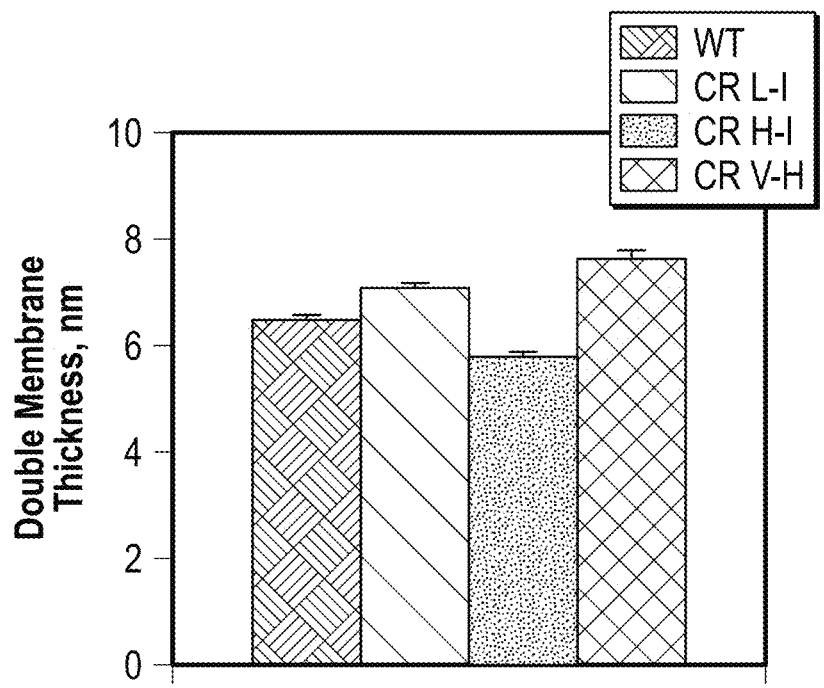
Figure 18J:
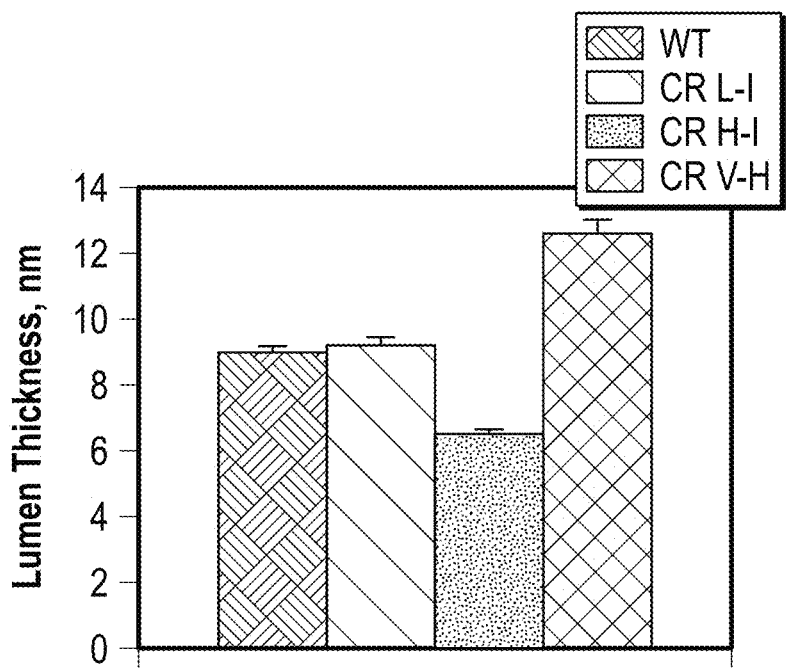
Figure 18K:
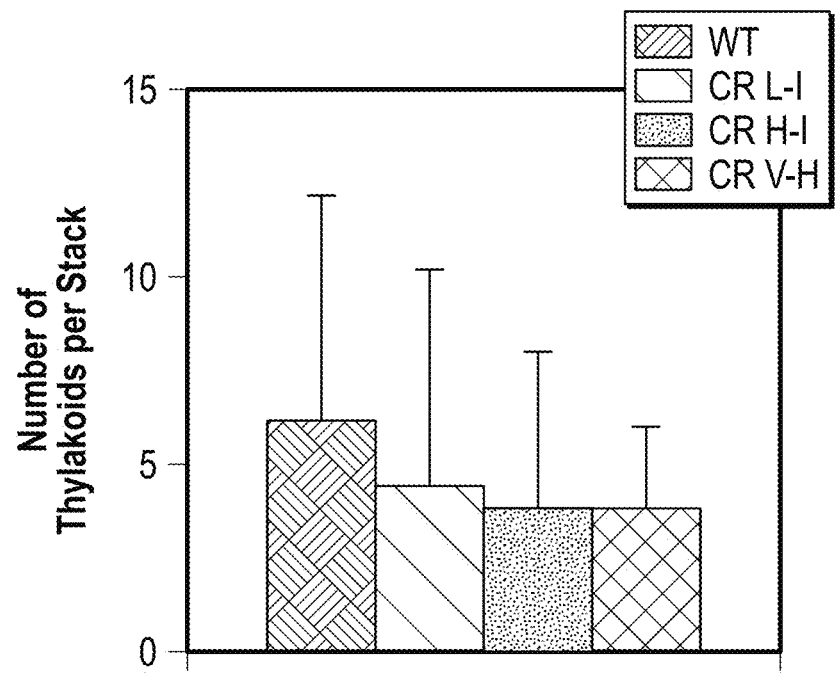
Figure 18L:
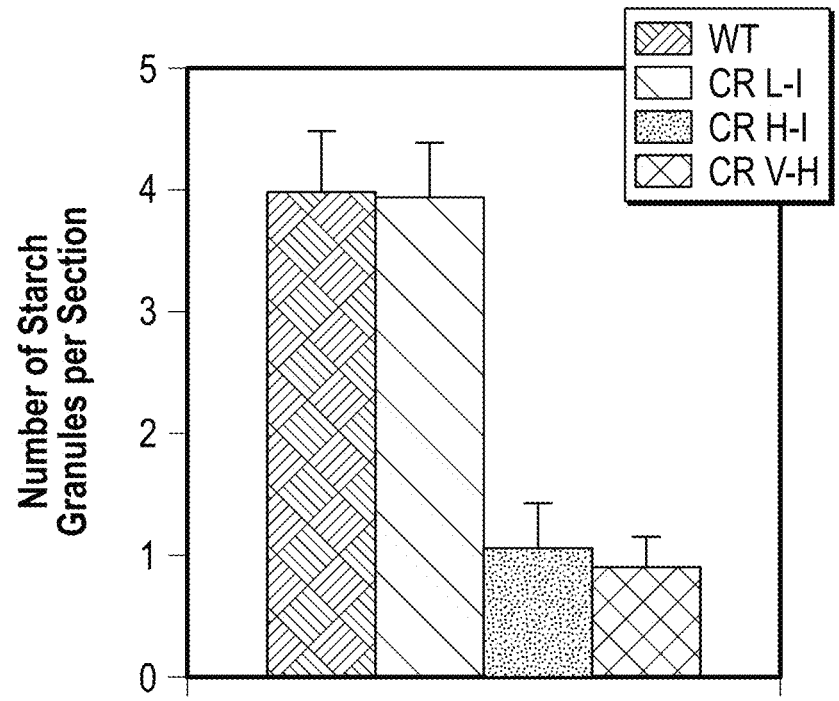
Figure 18M:
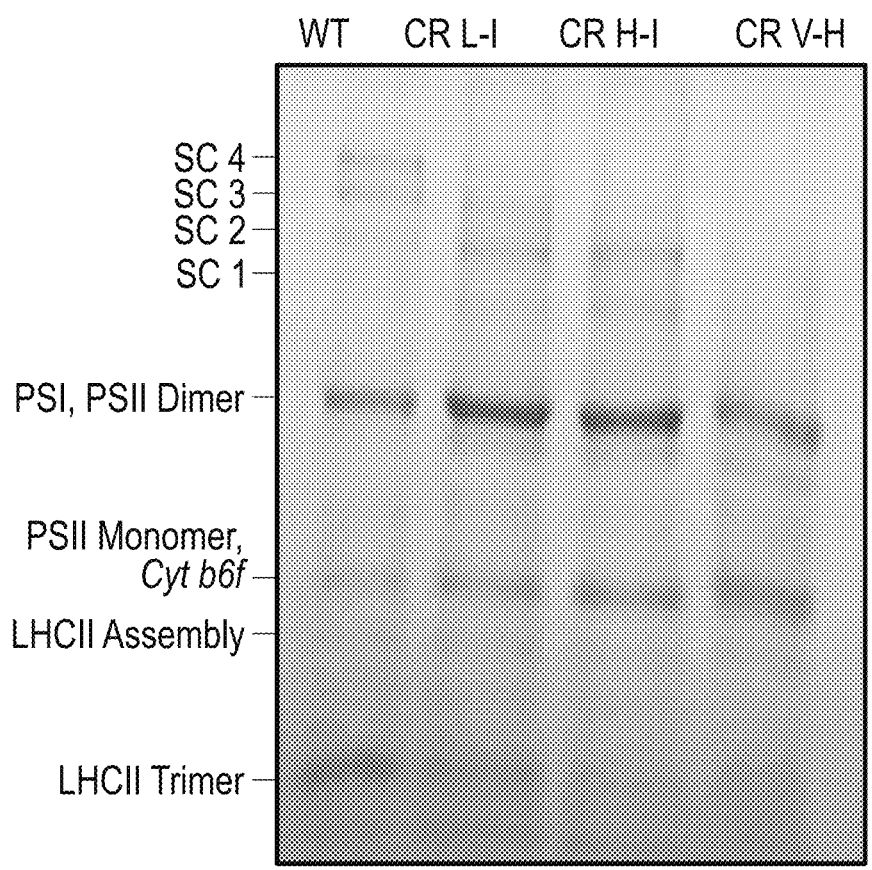

The Transition Point in Photosynthetic Efficiency is Related to PSII Supercomplex Composition To determine if the sharp drop in plant performance is correlated with dramatic changes in light harvesting supercomplex organization, the composition of light harvesting supercomplexes from thylakoid membranes was analyzed using blue native-PAGE (BN-PAGE), a technique commonly used to characterize intact membrane protein complexes. To monitor potential variations in PSII supercomplexes, we isolated thylakoid membranes from wild type and all CR lines and solubilized them by mild detergent treatment using α-dodecyl-maltoside. After separation under non-denaturing BN-PAGE conditions, 7 major chlorophyll-containing bands were observed (see FIG. 18M). The four upper bands on the gel represented various forms of PSII supercomplexes. For higher plants, the largest observed supercomplex, SC1, consists of a dimeric core (C2), two LHCII trimers (S) strongly bound to the complex, and two more trimers, moderately bound (trimer M) trimers (Caffarri, S., Kouril, R., Kereiche, S., Boekema, E. J. & Croce, R. Functional architecture of higher plant photosystem II supercomplexes. The EMBO Journal 28, 3052-3063 (2009); Boekema, E. J., Van Roon, H., Van Breemen, J. F. & Dekker, J. P. Supramolecular organization of photosystem II and its light-harvesting antenna in partially solubilized photosystem II membranes. European Journal of Biochemistry/FEBS 266, 444-452 (1999); Dekker and Boekema, 2005)). The smaller complexes are assigned as C2S2M (SC2), C2S2 (SC3), and C2S or S2M, based on the previous study.

The abundance of supercomlexes containing M-trimers, as well as of unattached L-trimers, decreases with increasing chl a/ratio. The transition from CR L-I to CR H-I lines corresponded to almost complete elimination of those higher order supercomplexes, as well as of L-trimers. Thus, in order to compensate for reduction of Chl b content, Camelina plants preferentially decreased the number of LHC subunits that tend to form loser association, which could serve to preserve the photosynthesis efficiency by retaining the strongly coupled antenna complexes.

Thylakoid Membrane Stacking is Altered with Antenna Modification

The chloroplast organization in C. sativa WT as well as in transgenic lines with different levels of Chl a/b was examined by transmission electron microscopy (TEM) to determine how thylakoid stacking was affected by LHCII content and supercomplex composition.

It was previously described that Chl b deficient mutants show compromised grana formation in variety of plants as soybean (H., N. et al. Characterization of the Arabidopsis thaliana mutant pcb2 which accumulates divinyl chlorophylls. Plant & Cell Physiology 46, 467-473 (2005)) or Arabidopsis (R. W. Keck et al, 1970). In agreement with previous observations, amount of thylakoids per granum in CR lines was progressively decreased in parallel with decreasing of Chl b levels. Interestingly, changes of thylakoid membrane structure in the grana were not linear for transgenic plants having a range of Chl a/b ratios. Plants with slightly decreased Chl b level (CR L-I) had slightly thicker double membranes and increased lumenal space compared to both wild type and CR H-I mutants. The less tightly appressed membranes structure could be an explanation for improved photosynthesis rate since it would facilitate diffusion of lumenal soluble electron transfer components such as plastocyanin and rearrangement of components of photosynthetic apparatus. CR H-I plants with Chl a/b ratios of 6-7 in contrary had thinner and more compact double thylakoid membrane compare to wild type and CR LI-mutant, which could impair diffusion of soluble electron transfer carriers.

CR-LI Lines Demonstrate Increased Yield in Field

To analyze the biomass and seed yield in CR lines under real-life conditions, we conducted a small-scale test field experiment in Nebraska. The plants with the highest Chl a/b ratio were not included in the study since our preliminary data demonstrated that they do not produce well-developed seed pods. We collected leaf samples from 4-week-old plants, to characterize Chl a/b ratios at different canopy levels. The results are shown in Table 1. Both WT and CR lines exhibited change in Chl a/b values between top, middle, and bottom leaves. Notably, however, in all CR transgenics the Chl a/b ratios were higher at all canopy levels compared to the corresponding values for wild type. At the top of the canopy, the WT plants had Chl a/b ratios of 3.2±0.1, CR-LI had ratios of 5.0±0.3, CR-HI of 5.6±0.1, and CR V-H of 7.0±0.4.

TABLE 1

Chl a/b ratios at different canopy levels of WT and CR L-I and two CR H-I lines grown in field studies

| Leaf position in canopy | Chl a/b Ratios | | | |
|---|---|---|---|---|
| | WT | CR L-I | CR H-I (1) | CR H-I (2) |
| Top | 3.2 ± 0.1 | 5.0 ± 0.3 | 5.6 ± 0.1 | 7.0 ± 0.4 |
| Middle | 3.0 ± 0.1 | 4.3 ± 0.2 | 4.9 ± 0.2 | 5.9 ± 0.4 |
| Bottom | 2.6 ± 0.2 | 3.9 ± 0.2 | 4.3 ± 0.3 | 4.6 ± 0.3 |

In plants grown as dense canopies, light availability is a major limiting factor for a net photosynthesis gain. As shown in FIG. 7, the light transmission though individual leaf significantly increases with antenna size reduction. Overall, between 400 and 700 nm, wild type leaves transmitted 36% less light compared to leaves with Chl a/b ratio of 4.3 (CR-LI line). Thus, this increased light penetration may result in improved biomass accumulation.

The seed and biomass yields are summarized in Table 2. Consistent with our previous observations, there was a transition point at which the Chl a/b increase stopped being beneficial for the productivity. Overall, the CR-LI transgenics that maintained their Chl a/b ratios at the top of the canopy near 5, had greater seed yield (+25%) and increase in total dry weight biomass (>40%) compared to wild type.

Seed yield increase resulted increased pod numbers, while the number of seeds per pod and weight of individual seeds stayed the same indicating that the plant response to increased photosynthate by increased flowering and subsequent seed and pod formation (Table 2).

Consistent with our previous observations, even a slight further increase in Chl a/b ratio was detrimental, with an abrupt drop in productivity. Already in the CR line with Chl a/b value of 5.6, a 33% decline in seed yield and 18% decline in biomass were observed compared to WT. In CR lines with Chl a/b levels of 7 at the top of the canopy, the seed yield dropped to just 40%, and the total dry weight biomass to 60%, of WT (see Table 2).

TABLE 2

Yield of WT and CR L-I and two CR H-I lines grown in field studies. (Values are the mean plus the standard error of 30 plants)

| Traits | WT | CR L-I | CR H-I (1) | CR H-I (2) |
| --- | --- | --- | --- | --- |
| Seed weight (g) | 3.6 ± 0.4 | 4.5 ± 0.4 | 2.4 ± 0.2 | 1.4 ± 0.1 |
| Seed weight (g) increase/decrease over WT (%) | n/a | +25% | −33% | −61% |
| Plant weight (g) | 11.8 ± 1.3 | 17.0 ± 1.3 | 9.6 ± 0.6 | 7.0 ± 0.5 |
| Plant weight (g) increase/decrease over WT (%) | n/a | +44% | −18% | −40% |
| No. of pods per plant | 481 ± 57 | 607 ± 53 | 375 ± 24 | 292 ± 23 |
| Seed weight/pod (mg) | 11.3 ± 0.6 | 10.0 ± 0.4 | 12.7 ± 0.6 | 11.3 ± 0.6 |

In this example, *Camelina sativa* plants were engineered with a range of Chl a/b ratios, resulting in a range of photosynthetic antenna sizes. The plants with slightly reduced antenna compared to wild type had improved photosynthetic performance at high light intensities when assayed as 4 week old plants. Furthermore, increased light penetration through plants' leaves throughout the day with slightly reduced antenna sizes allows for increased total plant photosynthesis throughout the canopy.

Example 6. Characterisitics of *Arabidopsis* NAB1-CAO Transgenic Lines

Transgenic lines were made as described in Example 4. Plants were grown for 4 weeks and then compared visually, for non photochemical quenching (NPQ) and chlorophyll content. As seen in FIG. 19 the transgenic plants grew much better than the Chlorina chlorophyll b minus mutant parent line. Both of the transgenic lines grew better than the parental line. The higher Chl a/b ratio line 3 (chl a/b=10) seemed to grow better than the lower Chl a/b line 1 (chl a/b=5) under the conditions utilized.

Chlorophyll determinations were done on the *Arabidopsis* NAB1-CAO transgenics and Chlorina mutants grown in moderate light, by spectrometry. Chl-5 and Chl-7 correspond to two Chlorina (Chlb-less) mutant lines. It is apparent that the transgenic lines had higher chlorophyll content per unit leaf area than that of the parental lines.

TABLE 3

Chlorophyll determination from leaf tissues of *Arabidopsis* transgenic NAB1-CAO lines compared to parental chlorophyll b minus Chlorina lines.

| Line | chlorophyll/cm$^2$ (leaf) | Chl a/Chl b |
| --- | --- | --- |
| NAB1-CAO-1 | 34.07 | 6.30 |
| NAB1-CAO-3 | 31.84 | 10.86 |
| Chl-5 | 11.58 | n/d |
| Chl-7 | 9.41 | n/d |

Non photochemical quenching of a transgenic NAB1-CAO line was compared to that in a Chlorina line under high and moderately high light intensities (FIG. 20). Both of the transgenic NAB1-CAO lines were significantly better at NPQ than the chlorophyll b minus chlorina line.

Although the invention has been described in detail with particular reference to these preferred embodiments, other embodiments can achieve the same results. For example, nucleic acids encoding a protein may correspond to a specific SEQ. ID. NO. but may also cover alterations allowed by the degeneracy of the genetic code. Variations and modifications of the present invention will be obvious to those skilled in the art and it is intended to cover in the appended claims all such modifications and equivalents. The entire disclosures of all references, applications, patents, and publications cited above are hereby incorporated by reference.

REFERENCES CITED

The following references and others cited herein but not listed here, to the extent that they provide exemplary procedural and other details supplementary to those set forth herein, are specifically incorporated herein by reference.

US PATENT DOCUMENTS

| | | |
| --- | --- | --- |
| 4,535,060 | 5,391,725 | 5,610,042 |
| 4,940,935 | 5,424,200 | 5,614,395 |
| 5,034,323 | 5,428,147 | 5,614,399 |
| 5,164,316 | 5,447,858 | 5,633,435 |
| 5,188,642 | 5,464,765 | 5,633,441 |
| 5,196,525 | 5,508,184 | 5,593,874 |
| 5,231,020 | 5,508,468 | 5,614,395 |
| 5,254,801 | 5,523,311 | 5,627,061 |
| 5,283,184 | 5,527,695 | 5,659,122 |
| 5,302,523 | 5,538,880 | 5,780,708 |
| 5,322,783 | 5,538,877 | 5,981,840 |
| 5,322,938 | 5,550,318 | 6,118,047 |
| 5,352,605 | 5,563,055 | 6,232,526 |
| 5,359,142 | 5,658,772 | 2003/0221211 |
| 5,378,619 | 5,591,616 | 2004/0029283 |
| 5,384,253 | 5,608,144 | |

OTHER PATENT DOCUMENTS

| | | |
| --- | --- | --- |
| EP 0 342 926 | WO 99/32619 | WO 01/29058, |
| WO 92/117598 | WO 00/44914. | WO 02/055692, |
| WO 95/06128 | WO 00/44895, | WO 02/44321, |
| WO 97/04103 | WO 00/63364 | W02005/054439, |
| WO 97/41228 | WO 00/01846, | W02005/110068 |
| WO 99/07409 | WO 01/36646, | WO2013/016267 |
| WO 99/60129 | WO 01175164, | |

OTHER PUBLICATIONS

ALI, N., DATTA, S. K. & DATTA, K. 2010. RNA interference in designing transgenic crops. *GMcrops*, 1, 207-13.

ALTSCHUL, S. F., GISH, W., MILLER, W., MYERS, E. W. & LIPMAN, D. J. 1990. Basic local alignment search tool. *J Mol Biol*, 215, 403-10.

ALTSCHUL, S. F., MADDEN, T. L., SCHAFFER, A. A., ZHANG, J., ZHANG, Z., MILLER, W. & LIPMAN, D. J. 1997. Gapped BLAST and PSI-BLAST: a new generation of protein database search programs. *Nucleic Acids Res*, 25, 3389-402.

BECHTOLD, N., ELLIS, J. & PELLETIER, G. 1993. In planta *Agrobacterium*-mediated gene transfer by in filtration of adult *Arabidopsis thaliana* plants. *C R Acad Sci Paris, Life Sciences*, 316, 1194-1199.

BLANKENSHIP, R. E. 2010. Early evolution of photosynthesis. *Plant Physiol*, 154, 434-8.

CHATTOPADHYAY, S., ANG, L. H., PUENTE, P., DENG, X. W. & WEI, N. 1998. *Arabidopsis* bZIP protein HY5 directly interacts with light-responsive promoters in mediating light control of gene expression. *Plant Cell*, 10, 673-83.

CLOUGH, S. J. & BENT, A. F. 1998. Floral dip: a simplified method for *Agrobacterium*-mediated transformation of *Arabidopsis thaliana*. *Plant J*, 16, 735-43.

COMAN, D., GRUISSEM, W. & HENNIG, L. 2013. Transcript profiling in *Arabidopsis* with genome tiling microarrays. *Methods Mol Biol*, 1067, 35-49.

CONG, L., RAN, F. A., COX, D., LIN, S., BARRETTO, R., HABIB, N., HSU, P. D., WU, X., JIANG, W., MARRAFFINI, L. A. & ZHANG, F. 2013. Multiplex genome engineering using CRISPR/Cas systems. *Science*, 339, 819-23.

DURNFORD, D. G., PRICE, J. A., MCKIM, S. M. & SARCHFIELD, M. L. 2003. Light-harvesting complex gene expression is controlled by both transcriptional and post-transcriptional mechanisms during photoacclimation in *Chlamydomonas reinhardtii*. *Physiologia Plantarum*, 118, 193-205.

EBERHARD, S., FINAZZI, G. & WOLLMAN, F. A. 2008. The dynamics of photosynthesis. *Annu Rev Genet*, 42, 463-515.

FOIANI, M., CIGAN, A. M., PADDON, C. J., HARASHIMA, S. & HINNEBUSCH, A. G. 1991. GCD2, a translational repressor of the GCN4 gene, has a general function in the initiation of protein synthesis in *Saccharomyces cerevisiae*. *Mol Cell Biol*, 11, 3203-16.

GAJ, T., GERSBACH, C. A. & BARBAS, C. F., 3RD 2013. ZFN, TALEN, and CRISPR/Cas-based methods for genome engineering. *Trends Biotechnol*, 31, 397-405.

JINKS-ROBERTSON, S. & NOMURA, M. 1982. Ribosomal protein S4 acts in trans as a translational repressor to regulate expression of the alpha operon in *Escherichia coli*. *J Bacteriol*, 151, 193-202.

JOZWIK, C. E. & MILLER, E. S. 1995. RNA-protein interactions of the bacteriophage RB69 RegAtranslational repressor protein. *Nucleic Acids Symp Ser*, 256-7.

KRIEGER-LISZKAY, A., FUFEZAN, C. & TREBST, A. 2008. Singlet oxygen production in photosystem II and related protection mechanism. *Photosynth Res*, 98, 551-64.

LEVIATAN, N., ALKAN, N., LESHKOWITZ, D. & FLUHR, R. 2013. Genome-wide survey of coldstress regulated alternative splicing in *Arabidopsis thaliana* with tiling microarray. *PLoS One*, 8, e66511.

LU, C. & KANG, J. 2008. Generation of transgenic plants of a potential oilseed crop *Camelina sativa* by *Agrobacterium*-mediated transformation. *Plant Cell Rep*, 27, 273-8.

MATSUOKA, M., TADA, Y., FUJIMURA, T. & KANO-MURAKAMI, Y. 1993. Tissue-specific light-regulated expression directed by the promoter of a C4 gene, maize pyruvate, orthophosphate dikinase, in a C3 plant, rice. *Proc Natl Acad Sci USA*, 90, 9586-90.

MINAGAWA, J. & TAKAHASHI, Y. 2004. Structure, function and assembly of Photosystem II and its light-harvesting proteins. *Photosynth Res*, 82, 241-63.

MULLER, P., LI, X. P. & NIYOGI, K. K. 2001. Non-photochemical quenching. A response to excess light energy. *Plant Physiol*, 125, 1558-66.

MUSSGNUG, J. H., WOBBE, L., ELLES, I., CLAUS, C., HAMILTON, M., FINK, A., KAHMANN, U., KAPAZO-GLOU, A., MULLINEAUX, C. W., HIPPLER, M., NICKELSEN, J., NIXON, P. J. & KRUSE, O. 2005. NAB1 is an RNA binding protein involved in the light-regulated differential expression of the light-harvesting antenna of *Chlamydomonas reinhardtii*. *Plant Cell*, 17, 3409-21.

NEALE, P. J. & MELIS, A. 1986. Algal photosynthetic membrane complexes and the photosynthesis-irradiance curve. A comparison of light-adaptation responses in *Chlamydomonas reinhardtii* (Chlorophyta). *J Phycology*, 22, 531-538.

POLLE, J., KANAKAGIRI, S., JIN, E.-S., MASUDA, T. & MELIS, A. 2002. Truncated chlorophyll antenna size of the photosystems—A practical method to improve microalgal producctivity and hydrogen production in mass culture. *Intl J Hydrogen Energy*, 27, 1257-1264.

POLLE, J. E., BENEMANN, J. R., TANAKA, A. & MELIS, A. 2000. Photosynthetic apparatus organization and function in the wild type and a chlorophyll b-less mutant of *Chlamydomonas reinhardtii*. Dependence on carbon source. *Planta*, 211, 335-44.

POLLE, J. E. W., NIYOGI, K. K. & MELIS, A. 2001. Absence of Lutein, Violaxanthin and Neoxanthin Affects the Functional Chlorophyll Antenna Size of Photosystem-II but not that of Photosystem-I in the Green Alga *Chlamydomonas reinhardtii*. *Plant Cell Physiology*, 42, 482-491.

REECK, G. R., D E HAEN, C., TELLER, D. C., DOOLITTLE, R. F., FITCH, W. M., DICKERSON, R. E., CHAMBON, P., MCLACHLAN, A. D., MARGOLIASH, E., JUKES, T. H. & ET AL. 1987. "Homology" in proteins and nucleic acids: a terminology muddle and a way out of it. *Cell*, 50, 667.

SACCOMANNO, L., LOUSHIN, C., JAN, E., PUNKAY, E., ARTZT, K. & GOODWIN, E. B. 1999. The STAR protein QKI-6 is a translational repressor. *Proc Natl Acad Sci USA*, 96, 12605-10.

SCHULZ, G. & SCHIRMER, R. 1979. *Principles of Protein Structure*, New York, Springer. TANAKA, R., KOSHINO, Y., SAWA, S., ISHIGURO, S., OKADA, K. & TANAKA, A. 2001. Overexpression of chlorophyllide a oxygenase (CAO) enlarges the antenna size of photosystem II in *Arabidopsis thaliana*. *Plant J*, 26, 365-73

VASS, I. & CSER, K. 2009. Janus-faced charge recombinations in photosystem II photoinhibition. *Trends Plant Sci*, 14, 200-5.

YANAGISAWA, S. & SHEEN, J. 1998. Involvement of maize Dof zinc finger proteins in tissue-specific and light-regulated gene expression. *Plant Cell*, 10, 75-89.

ZHANG, F. 2014. CRISPR-Cas systems and methods for altering expression of gene products. U.S. patent application Ser. No. 14/054,414. Apr. 15, 2014.

The invention claimed is:

1. A genetically modified plant wherein a native chlorophyll a oxidase gene (Cao) has suppressed Cao expression in the modified plant and the genetically modified plant is capable of modulating its photosynthetic antenna complex composition in response to increases or decreases in light intensity by modulation of the ratio of chlorophyll a to chlorophyll b (Chl a/b) such that there is an increase in the Chl a/b ratio of the antenna complex composition in the upper canopy (high light intensity) versus a Chl a/b ratio in an antenna complex composition in an upper canopy of wildtype plants grown in the same conditions and a decrease in the Chl a/b ratio in a lower canopy (low light intensity) of the genetically modified plant as compared to the Chl a/b ratio in the upper canopy of the genetically modified plant wherein the genetically modified plant comprises a DNA construct comprising a heterologous expression control sequence operatively linked to a polynucleotide sequence encoding a chlorophyll a oxidase, and wherein the expression control sequence interacts with a redox-sensitive modulator responsive to changes in ambient light intensity, wherein the redox-sensitive modulator is chosen from NAB1, GCD2, and GLD-1.

2. The genetically modified plant of claim 1, wherein the native chlorophyll a oxidase gene is disrupted using a procedure chosen from CRISPR/Cas 9 mediated genome editing, TALEN-mediated gene disruption, chemical mutagenesis coupled with TILING, insertional mutagenesis coupled with PCR screening for insertion events in the native chlorophyll a oxidase gene, gene disruption by RNA interference (RNAi).

3. The genetically modified plant of claim 1, wherein the heterologous expression control sequences comprise a cold-shock domain sequence motif.

4. The genetically modified plant of claim 3, wherein the cold shock domain sequence motif is operatively linked to a promoter.

5. The genetically modified plant of claim 4, wherein the promoter is chosen from the group consisting of psaD, actin, ubiquitin, β-tublin, PR-1a, and 35S.

6. The genetically modified plant of claim 1, wherein the DNA construct includes a reverse compliment of the polynucleotide sequence encoding a chlorophyll a oxidase fragment and the expression controlled sequence is a tissue-specific promoter that is responsive to changes in ambient light intensity.

7. The genetically modified plant of claim 6, wherein the tissue-specific promoter is CAB1 or RbcS.

8. The genetically modified plant of claim 1 wherein the genetically modified plant may be selected from the group consisting of millet, corn (maize), sorghum, barley, oats, rice, rye, teff, triticale, wheat, rice, wild rice, amaranth, beans, lentils, fava, lupin, peanuts, chickpeas, pigeon peas, soybeans, mustards, rape seed (canola), safflower, sunflower, flax, jatropha, hemp, *Arabidopsis, Camelina*, poppy, trees (poplar, willow, *Eucalyptus*, southern beech, sycamore, ash), *Miscanthus*, hemp, switchgrass, reed, canary grass, rye, giant reed, beets, sweet sorghum, sugar cane, potatoes, sweet potatoes, cassava, olives, soybean, rapeseed, and corn.

9. The genetically modified plant of claim 8, wherein the genetically modified plant is *Camelina*.

10. A method to produce a genetically modified plant wherein a native chlorophyll a oxidase gene (Cao) has suppressed Cao expression in the modified plant and the genetically modified plant is capable of modulating its Chl a/b ratio of an antenna complex in response to ambient sunlight comprising the steps of:
   a) transforming a plant with a heterologous polynucleotide sequence comprising an expression control sequence operatively linked to a polynucleotide sequence encoding a chlorophyll a oxidase wherein the expression control sequence interacts with a redox-sensitive modulator responsive to changes in ambient light intensity, wherein the redox-sensitive modulator is chosen from NAB1, GCD2, and GLD-1, wherein the native Cao has suppressed Cao expression in the genetically modified plant; and
   b) selecting the genetically modified plant that is capable of modulating the antenna size in response to changes in light intensity such that there is an increase in the Chl a/b ratio of the antenna complex composition in the upper canopy (high light intensity) versus a Chl a/b ratio in an antenna complex composition in an upper canopy of wild-type plants grown in the same conditions and a decrease in the Chl a/b ratio in a lower canopy (low light intensity) of the genetically modified plant as compared to the Chl a/b ratio in the upper canopy of the genetically modified plant.

11. A method to produce a genetically modified plant with the ability to modulate its Chl a/b ratio of an antenna complex in response to ambient sunlight comprising the steps of:
   a) producing a genetically modified plant wherein an endogenous chlorophyll a oxidase gene (Cao) has suppressed Cao expression;
   b) transforming the genetically modified plant with a heterologous polynucleotide sequence encoding for a modified chlorophyll a oxidase wherein expression of the modified chlorophyll a oxidase is controlled by changes in ambient light intensity wherein the expression control sequence interacts with a redox-sensitive modulator responsive to changes in ambient light intensity, wherein the redox-sensitive modulator is chosen from NAB1, GCD2, and GLD-1; and
   c) selecting a genetically modified plant that is capable of modulating the antenna size in response to changes in light intensity such that there is an increase in the Chl a/b ratio of the antenna complex composition in the upper canopy (high light intensity) versus a Chl a/b ratio in an antenna complex composition in an upper canopy of wild-type plants grown in the same conditions and a decrease in the Chl a/b ratio in a lower canopy (low light intensity) of the genetically modified plant as compared to the Chl a/b ratio in the upper canopy of the genetically modified plant.

12. The method of claim 11, wherein the heterologous polynucleotide sequence comprises a promoter operatively linked to a cold-shock domain consensus sequence.

13. The method of claim 12 wherein the cold-shock domain sequence is chosen from the group consisting of: SEQ. ID. NO. 18-26.

14. The method of claim 11, wherein the heterologous polynucleotide comprises a promoter operatively linked to the modified chlorophyll a oxidase chosen from psaD, actin, ubiquitin, β-tublin, 35S, and PR1-a.

15. The method of claim 10, wherein the heterologous polynucleotide sequence comprises a tissue targeting sequence.

* * * * *

UNITED STATES PATENT AND TRADEMARK OFFICE
CERTIFICATE OF CORRECTION

PATENT NO. : 10,745,708 B2
APPLICATION NO. : 15/594274
DATED : August 18, 2020
INVENTOR(S) : Richard Thomas Sayre Page 1 of 1

It is certified that error appears in the above-identified patent and that said Letters Patent is hereby corrected as shown below:

In the Specification

Column 1, Lines 25-29 are replaced as shown:
This invention was made with government support under Contract/Grant Nos. EF-1219603 awarded by the National Science Foundation and; Prime No: DE-SC000195, Sub No: 21017-NM awarded by the Department of Energy (DOE-CABS); DE-SC0001035 awarded under DOE-PARC; DE-EE0006316 awarded under DOE-REAP; DE-EE007089 and DOE DE-EE0003046 awarded by DOE-PACE. The government has certain rights in the invention.

Signed and Sealed this
Twenty-seventh Day of October, 2020

Andrei Iancu
*Director of the United States Patent and Trademark Office*

SEQUENCE LISTING

<160> NUMBER OF SEQ ID NOS: 29

<210> SEQ ID NO 1
<211> LENGTH: 645
<212> TYPE: PRT
<213> ORGANISM: Chlamydomonas reinhardtii
<220> FEATURE:
<221> NAME/KEY: MISC_FEATURE
<223> OTHER INFORMATION: Chlorophyll a oxygenase (CAO)

<400> SEQUENCE: 1

```
Met Leu Pro Ala Ser Leu Gln Arg Lys Ala Ala Val Gly Gly Arg
1               5                   10                  15

Gly Pro Thr Asn Gln Ser Arg Val Ala Val Arg Val Ser Ala Gln Pro
            20                  25                  30

Lys Glu Ala Pro Pro Ala Ser Thr Pro Ile Val Glu Asp Pro Glu Ser
            35                  40                  45

Lys Phe Arg Arg Tyr Gly Lys His Phe Gly Gly Ile His Lys Leu Ser
        50                  55                  60

Met Asp Trp Leu Asp Ser Val Pro Arg Val Arg Val Arg Thr Lys Asp
65              70                  75                  80

Ser Arg Gln Leu Asp Asp Met Leu Glu Leu Ala Val Leu Asn Glu Arg
                85                  90                  95

Leu Ala Gly Arg Leu Glu Pro Trp Gln Ala Arg Gln Lys Leu Glu Tyr
            100                 105                 110

Leu Arg Lys Arg Lys Asn Trp Glu Arg Ile Phe Glu Tyr Val Thr
        115                 120                 125

Arg Gln Asp Ala Ala Ala Thr Leu Ala Met Ile Glu Glu Ala Asn Arg
    130                 135                 140

Lys Val Glu Glu Ser Leu Ser Glu Glu Ala Arg Glu Lys Thr Ala Val
145                 150                 155                 160

Gly Asp Leu Arg Asp Gln Leu Glu Ser Leu Arg Ala Gln Val Ala Gln
                165                 170                 175

Ala Gln Glu Arg Leu Ala Met Thr Gln Ser Arg Val Glu Gln Asn Leu
            180                 185                 190

Gln Arg Val Asn Glu Leu Lys Ala Glu Ala Thr Thr Leu Glu Arg Met
        195                 200                 205

Arg Lys Ala Ser Asp Leu Asp Ile Lys Glu Arg Glu Arg Ile Ala Ile
    210                 215                 220

Ser Thr Val Ala Ala Lys Gly Pro Ala Ser Ser Ser Ser Ala Ala
225                 230                 235                 240

Ala Val Ser Ala Pro Ala Thr Ser Ala Thr Leu Thr Val Glu Arg Pro
                245                 250                 255

Ala Ala Thr Thr Val Thr Gln Glu Val Pro Ser Thr Ser Tyr Gly Thr
            260                 265                 270

Pro Val Asp Arg Ala Pro Arg Arg Ser Lys Ala Ala Ile Arg Arg Ser
        275                 280                 285

Arg Gly Leu Glu Ser Ser Met Glu Ile Glu Glu Gly Leu Arg Asn Phe
    290                 295                 300

Trp Tyr Pro Ala Glu Phe Ser Ala Arg Leu Pro Lys Asp Thr Leu Val
305                 310                 315                 320

Pro Phe Glu Leu Phe Gly Glu Pro Trp Val Met Phe Arg Asp Glu Lys
```

```
                325                 330                 335
Gly Gln Pro Ser Cys Ile Arg Asp Glu Cys Ala His Arg Gly Cys Pro
            340                 345                 350

Leu Ser Leu Gly Lys Val Val Glu Gly Gln Val Met Cys Pro Tyr His
        355                 360                 365

Gly Trp Glu Phe Asn Gly Asp Gly Ala Cys Thr Lys Met Pro Ser Thr
    370                 375                 380

Pro Phe Cys Arg Asn Val Gly Val Ala Ala Leu Pro Cys Ala Glu Lys
385                 390                 395                 400

Asp Gly Phe Ile Trp Val Trp Pro Gly Asp Gly Leu Pro Ala Glu Thr
                405                 410                 415

Leu Pro Asp Phe Ala Gln Pro Pro Glu Gly Phe Leu Ile His Ala Glu
            420                 425                 430

Ile Met Val Asp Val Pro Val Glu His Gly Leu Leu Ile Glu Asn Leu
        435                 440                 445

Leu Asp Leu Ala His Ala Pro Phe Thr His Thr Ser Thr Phe Ala Arg
    450                 455                 460

Gly Trp Pro Val Pro Asp Phe Val Lys Phe His Ala Asn Lys Ala Leu
465                 470                 475                 480

Ser Gly Phe Trp Asp Pro Tyr Pro Ile Asp Met Ala Phe Gln Pro Pro
                485                 490                 495

Cys Met Thr Leu Ser Thr Ile Gly Leu Ala Gln Pro Gly Lys Ile Met
            500                 505                 510

Arg Gly Val Thr Ala Ser Gln Cys Lys Asn His Leu His Gln Leu His
        515                 520                 525

Val Cys Met Pro Ser Lys Lys Gly His Thr Arg Leu Leu Tyr Arg Met
    530                 535                 540

Ser Leu Asp Phe Leu Pro Trp Met Arg His Val Pro Phe Ile Asp Arg
545                 550                 555                 560

Ile Trp Lys Gln Val Ala Ala Gln Val Leu Gly Glu Asp Leu Val Leu
                565                 570                 575

Val Leu Gly Gln Gln Asp Arg Met Leu Arg Gly Gly Ser Asn Trp Ser
            580                 585                 590

Asn Pro Ala Pro Tyr Asp Lys Leu Ala Val Arg Tyr Arg Arg Trp Arg
        595                 600                 605

Asn Gly Val Asn Ala Glu Val Ala Arg Val Arg Ala Gly Glu Pro Pro
    610                 615                 620

Ser Asn Pro Val Ala Met Ser Ala Gly Glu Met Phe Ser Val Asp Glu
625                 630                 635                 640

Asp Asp Met Asp Asn
                645

<210> SEQ ID NO 2
<211> LENGTH: 657
<212> TYPE: PRT
<213> ORGANISM: Volvox carteri f. nagariensis
<220> FEATURE:
<221> NAME/KEY: MISC_FEATURE
<223> OTHER INFORMATION: chlorophyll a oxygenase

<400> SEQUENCE: 2

Met Leu Pro Ala Gln Arg Gln Cys Arg Thr Ser Ala Cys Gln Gly Arg
1               5                   10                  15

Gly Ile Ile Ser Lys Arg Thr Ile Arg Ala Asp Phe Lys Val His Ala
            20                  25                  30
```

```
Ser Val Ser Gln Gln Pro Ser Asp Lys Pro Glu Gln Gln Ala Val
     35                  40                  45
Pro Ser Ile Val Glu Asp Pro Glu Ala Lys Phe Arg Arg Tyr Gly Lys
 50                  55                  60
His Phe Gly Gly Ile His Lys Leu Asn Leu Asp Trp Leu Glu Ala Val
 65                  70                  75                  80
Pro Arg Val Arg Val Arg Thr Lys Asp Ser Arg Gln Leu Asp Glu Leu
                 85                  90                  95
Leu Glu Leu Ala Val Leu Asn Glu Leu Ala Gly Arg Leu Glu Pro
             100                 105                 110
Trp Gln Ala Arg Gln Lys Leu Glu Tyr Leu Arg Lys Arg Lys Asn
             115                 120                 125
Trp Glu Arg Ile Phe Glu Tyr Val Thr Lys Gln Asp Ala Ala Thr
 130                 135                 140
Leu Ala Met Ile Glu Glu Ala Asn Arg Lys Val Glu Glu Ala Leu Ser
 145                 150                 155                 160
Glu Glu Ala Arg Glu Arg Thr Ala Val Gly Asp Leu Arg Glu Gln Leu
                 165                 170                 175
Gln Val Leu Gln Arg Gln Val Gln Glu Ala Gln Glu Arg Leu Gln Leu
             180                 185                 190
Thr Gln Ala Arg Val Glu Gln Asn Leu Asn Arg Val Asn Glu Leu Lys
             195                 200                 205
Ala Glu Ala Val Gly Leu Glu Arg Met Arg Asn Gly Arg Met Gly Gly
             210                 215                 220
Asp Arg Lys Lys Glu Leu Gln Val Ala Ala Pro Val Ala Val Thr Ala
 225                 230                 235                 240
Ala Ala Ser Ala Ala Arg Pro Ala Val Ser Ala Thr Ala Val Ala Glu
                 245                 250                 255
Ser Val Pro Ala Ala Ile Val Thr Val Glu Pro Pro Thr Arg Ser Tyr
                 260                 265                 270
Thr Pro Asn Gly Ser Ser Asp Gly Thr Ser Val Val Ala Pro Pro Gly
             275                 280                 285
Arg Arg Ser Lys Val Ala Ile Arg Arg Gly Arg Gly Leu Glu Ser Ser
 290                 295                 300
Leu Asp Phe Glu Pro Gly Leu Arg Asn Phe Trp Tyr Pro Ala Glu Phe
 305                 310                 315                 320
Ser Ala Lys Leu Gly Gln Asp Thr Leu Val Pro Phe Glu Leu Phe Gly
                 325                 330                 335
Glu Pro Trp Val Leu Phe Arg Asp Glu Lys Gly Gln Pro Ala Cys Ile
             340                 345                 350
Lys Asp Glu Cys Ala His Arg Ala Cys Pro Leu Ser Leu Gly Lys Val
             355                 360                 365
Val Glu Gly Gln Val Val Cys Ala Tyr His Gly Trp Glu Phe Asn Gly
 370                 375                 380
Asp Gly His Cys Thr Lys Met Pro Ser Thr Pro His Cys Arg Asn Val
 385                 390                 395                 400
Gly Val Ser Ala Leu Pro Cys Ala Glu Lys Asp Gly Phe Ile Trp Val
                 405                 410                 415
Trp Pro Gly Asp Gly Leu Pro Ala Gln Thr Leu Pro Asp Phe Ala Arg
             420                 425                 430
Pro Pro Glu Gly Phe Gln Val His Ala Glu Ile Met Val Asp Val Pro
 435                 440                 445
Val Glu His Gly Leu Leu Met Glu Asn Leu Leu Asp Leu Ala His Ala
```

```
                450             455             460
Pro Phe Thr His Thr Thr Thr Phe Ala Arg Gly Trp Pro Val Pro Asp
465                 470                 475                 480

Phe Val Lys Phe His Thr Asn Lys Leu Leu Ser Gly Tyr Trp Asp Pro
                485                 490                 495

Tyr Pro Ile Asp Met Ala Phe Gln Pro Pro Cys Met Val Leu Ser Thr
            500                 505                 510

Ile Gly Leu Ala Gln Pro Gly Lys Ile Met Arg Gly Val Thr Ala Ser
            515                 520                 525

Gln Cys Lys Asn His Leu His Gln Leu His Val Cys Met Pro Ser Lys
        530                 535                 540

Lys Gly His Thr Arg Leu Leu Tyr Arg Met Ser Leu Asp Phe Leu Pro
545                 550                 555                 560

Trp Met Arg Tyr Val Pro Phe Ile Asp Lys Val Trp Lys Asn Val Ala
                565                 570                 575

Gly Gln Val Leu Gly Glu Asp Leu Val Leu Val Leu Gly Gln Gln Asp
                580                 585                 590

Arg Leu Leu Arg Gly Gly Asn Thr Trp Ser Asn Pro Ala Pro Tyr Asp
                595                 600                 605

Lys Leu Ala Val Arg Tyr Arg Arg Trp Arg Asn Ser Val Ser Pro Asp
610                 615                 620

Gly Ala Gly Leu Asp Gly Pro Ala Pro Leu Asn Pro Val Ala Met Ser
625                 630                 635                 640

Ala Gly Glu Met Phe Ser Ile Asp Glu Asp Glu Gln Asp Pro Arg Met
                645                 650                 655

Gln

<210> SEQ ID NO 3
<211> LENGTH: 463
<212> TYPE: PRT
<213> ORGANISM: Dunaliella salina
<220> FEATURE:
<221> NAME/KEY: MISC_FEATURE
<223> OTHER INFORMATION: CAO mRNA for chlorophyll b synthase

<400> SEQUENCE: 3

Met Gln Ser Lys Leu Leu Gly Leu Gln Asp Glu Ile Ser Glu Ala Arg
1               5                   10                  15

Asp Lys Leu Arg Thr Ser Glu Ala Arg Val Ala Gln Asn Leu Lys Arg
                20                  25                  30

Val Asp Glu Leu Lys Ala Glu Ala Ala Ser Leu Glu Arg Met Arg Leu
            35                  40                  45

Ala Ser Ser Ser Thr Asp Ser Thr Val Ser Ile Ala Ser Arg Gly
        50                  55                  60

Gly Ala Ala Val Ala Ala Thr Thr Ser Val Pro Asp His Val Glu Arg
65                  70                  75                  80

Glu Gly Ile Gln Ser Arg Val Arg Gly Ser Gly Met Ala Ser Thr Ser
                85                  90                  95

Tyr Pro Ser His Val Pro Gln Pro Ser Gln Ala Val Arg Arg Gly Pro
            100                 105                 110

Lys Pro Lys Asp Ser Arg Arg Leu Arg Ser Ser Leu Glu Leu Glu Asp
        115                 120                 125

Gly Leu Arg Asn Phe Trp Tyr Pro Thr Glu Phe Ala Lys Lys Leu Glu
    130                 135                 140

Pro Gly Met Met Val Pro Phe Asp Leu Phe Gly Val Pro Trp Val Leu
```

```
                145                 150                 155                 160
Phe Arg Asp Glu His Ser Ala Pro Thr Cys Ile Lys Asp Ser Cys Ala
                    165                 170                 175

His Arg Ala Cys Pro Leu Ser Leu Gly Lys Val Ile Asn Gly His Val
                    180                 185                 190

Gln Cys Pro Tyr His Gly Trp Glu Phe Asp Gly Ser Gly Ala Cys Thr
                    195                 200                 205

Lys Met Pro Ser Thr Arg Met Cys His Gly Val Gly Val Ala Ala Leu
            210                 215                 220

Pro Cys Val Glu Lys Asp Gly Phe Val Trp Val Trp Pro Gly Asp Gly
225                 230                 235                 240

Pro Pro Pro Asp Leu Pro Pro Asp Phe Thr Ala Pro Pro Ala Gly Tyr
                245                 250                 255

Asp Val His Ala Glu Ile Met Val Asp Val Pro Val Glu His Gly Leu
                260                 265                 270

Leu Met Glu Asn Leu Leu Asp Leu Ala His Ala Pro Phe Thr His Thr
                275                 280                 285

Thr Thr Phe Ala Arg Gly Trp Pro Ile Pro Glu Ala Val Arg Phe His
            290                 295                 300

Ala Thr Lys Met Leu Ala Gly Asp Trp Asp Pro Tyr Pro Ile Ser Met
305                 310                 315                 320

Ser Phe Asn Pro Pro Cys Ile Ala Leu Ser Thr Ile Gly Leu Ser Gln
                325                 330                 335

Pro Gly Lys Ile Met Arg Gly Tyr Lys Ala Glu Glu Cys Lys Arg His
                340                 345                 350

Leu His Gln Leu His Val Cys Met Pro Ser Lys Glu Gly His Thr Arg
                355                 360                 365

Leu Leu Tyr Arg Met Ser Leu Asp Phe Trp Gly Trp Ala Lys His Val
            370                 375                 380

Pro Phe Val Asp Val Leu Trp Lys Lys Ile Ala Gly Gln Val Leu Gly
385                 390                 395                 400

Glu Asp Leu Val Leu Val Leu Gly Gln Gln Ala Arg Met Ile Gly Gly
                405                 410                 415

Asp Asp Thr Trp Cys Thr Pro Met Pro Tyr Asp Lys Leu Ala Val Arg
                420                 425                 430

Tyr Arg Arg Trp Arg Asn Met Val Ala Asp Gly Glu Tyr Glu Glu Gly
            435                 440                 445

Ser Arg Asn Arg Cys Thr Ser Gln Tyr Asp Ser Trp Pro Asp Val
450                 455                 460

<210> SEQ ID NO 4
<211> LENGTH: 297
<212> TYPE: PRT
<213> ORGANISM: Nephroselmis pyriformis
<220> FEATURE:
<221> NAME/KEY: MISC_FEATURE
<223> OTHER INFORMATION: CAOa for chlorophyllide a oxygenase

<400> SEQUENCE: 4

Ala Val Glu Phe Thr Ser Arg Leu Gly Lys Asp Ile Met Val Pro Phe
1               5                   10                  15

Glu Cys Phe Glu Glu Ser Trp Val Leu Phe Arg Asp Glu Asp Gly Lys
                20                  25                  30

Ala Gly Cys Ile Lys Asp Glu Cys Ala His Arg Ala Cys Pro Leu Ser
            35                  40                  45
```

```
Leu Gly Thr Val Glu Asn Gly Gln Ala Thr Cys Ala Tyr His Gly Trp
 50                  55                  60

Gln Phe Ser Thr Gly Gly Glu Cys Thr Lys Ile Pro Ser Val Gly Ala
 65                  70                  75                  80

Arg Gly Cys Ser Gly Val Gly Val Arg Ala Met Pro Thr Val Glu Gln
                 85                  90                  95

Asp Gly Met Ile Trp Ile Trp Pro Gly Asp Glu Lys Pro Ala Glu His
            100                 105                 110

Ile Pro Ser Lys Glu Val Leu Pro Ala Gly His Thr Leu His Ala
        115                 120                 125

Glu Ile Val Leu Asp Val Pro Val Glu His Gly Leu Leu Glu Asn
130                 135                 140

Leu Leu Asp Leu Ala His Ala Pro Phe Thr His Thr Ser Thr Phe Ala
145                 150                 155                 160

Lys Gly Trp Ala Val Pro Glu Leu Val Lys Phe Ser Thr Asp Lys Val
                165                 170                 175

Arg Ala Leu Gly Gly Ala Trp Glu Pro Tyr Pro Ile Asp Met Ser Phe
            180                 185                 190

Glu Pro Pro Cys Met Val Leu Ser Thr Ile Gly Leu Ala Gln Pro Gly
        195                 200                 205

Lys Val Asp Ala Gly Val Arg Ala Ser Glu Cys Glu Lys His Leu His
210                 215                 220

Gln Leu His Val Cys Met Pro Ser Gly Ala Gly Lys Thr Arg Leu Leu
225                 230                 235                 240

Tyr Arg Met His Leu Asp Phe Met Pro Phe Leu Lys Tyr Val Pro Gly
                245                 250                 255

Met His Leu Val Trp Glu Ala Met Ala Asn Gln Val Leu Gly Glu Asp
            260                 265                 270

Leu Arg Leu Val Leu Gly Gln Gln Asp Arg Leu Gln Arg Gly Gly Asp
        275                 280                 285

Val Trp Ser Asn Pro Met Glu Tyr Asp
    290                 295

<210> SEQ ID NO 5
<211> LENGTH: 299
<212> TYPE: PRT
<213> ORGANISM: Mesostigma viride
<220> FEATURE:
<221> NAME/KEY: MISC_FEATURE
<223> OTHER INFORMATION: CAO for chlorophyllide a oxygenase

<400> SEQUENCE: 5

Asp Glu Asp Gly Arg Val Ala Cys Leu Arg Asp Glu Cys Ala His Arg
 1               5                  10                  15

Ala Cys Pro Leu Ser Leu Gly Thr Val Glu Asn Gly His Ala Thr Cys
                20                  25                  30

Pro Tyr His Gly Trp Gln Tyr Asp Thr Asp Gly Lys Cys Thr Lys Met
            35                  40                  45

Pro Gln Thr Arg Leu Arg Ala Gln Val Arg Val Ser Thr Leu Pro Val
        50                  55                  60

Arg Glu His Asp Gly Met Ile Trp Val Tyr Pro Gly Ser Asn Glu Pro
 65                  70                  75                  80

Pro Glu His Leu Pro Ser Phe Leu Pro Pro Ser Asn Phe Thr Val His
                85                  90                  95

Ala Glu Leu Val Leu Glu Val Pro Ile Glu His Gly Leu Met Ile Glu
            100                 105                 110
```

```
Asn Leu Leu Asp Leu Ala His Ala Pro Phe Thr His Thr Glu Thr Phe
        115                 120                 125

Ala Lys Gly Trp Ser Val Pro Asp Ser Val Asn Phe Lys Val Ala Ala
130                 135                 140

Gln Ser Leu Ala Gly His Trp Glu Pro Tyr Pro Ile Ser Met Lys Phe
145                 150                 155                 160

Glu Pro Pro Cys Met Thr Ile Ser Glu Ile Gly Leu Ala Lys Pro Gly
                165                 170                 175

Gln Leu Glu Ala Gly Lys Phe Ser Gly Glu Cys Lys Gln His Leu His
            180                 185                 190

Gln Leu His Val Cys Met Pro Ala Gly Glu Gly Arg Thr Arg Ile Leu
        195                 200                 205

Tyr Arg Met Cys Leu Asp Phe Ala His Trp Val Lys Tyr Ile Pro Gly
    210                 215                 220

Ile Gln Asn Val Trp Ser Gly Met Ala Thr Gln Val Leu Gly Glu Asp
225                 230                 235                 240

Leu Arg Leu Val Glu Gly Gln Gln Asp Arg Met Leu Arg Gly Ala Asp
                245                 250                 255

Ile Trp Tyr Asn Pro Val Ala Tyr Asp Lys Leu Gly Val Arg Tyr Arg
            260                 265                 270

Ser Trp Arg Arg Ala Val Glu Arg Asn Thr Arg Ser Arg Phe Ile Gly
        275                 280                 285

Gly Gln Glu Lys Leu Ala Pro Glu Gly Arg Asp
    290                 295

<210> SEQ ID NO 6
<211> LENGTH: 247
<212> TYPE: PRT
<213> ORGANISM: Chlamydomonas reinhardtii
<220> FEATURE:
<221> NAME/KEY: MISC_FEATURE
<223> OTHER INFORMATION: nucleic acid binding protein

<400> SEQUENCE: 6

Met Gly Glu Gln Leu Arg Gln Gln Gly Thr Val Lys Trp Phe Asn Ala
1               5                   10                  15

Thr Lys Gly Phe Gly Phe Ile Thr Pro Gly Gly Gly Gly Glu Asp Leu
            20                  25                  30

Phe Val His Gln Thr Asn Ile Asn Ser Glu Gly Phe Arg Ser Leu Arg
        35                  40                  45

Glu Gly Glu Val Val Glu Phe Glu Val Glu Ala Gly Pro Asp Gly Arg
    50                  55                  60

Ser Lys Ala Val Asn Val Thr Gly Pro Gly Ala Ala Pro Glu Gly
65                  70                  75                  80

Ala Pro Arg Asn Phe Arg Gly Gly Arg Gly Arg Gly Arg Ala Arg
                85                  90                  95

Gly Ala Arg Gly Gly Tyr Ala Ala Ala Tyr Gly Tyr Pro Gln Met Ala
            100                 105                 110

Pro Val Tyr Pro Gly Tyr Tyr Phe Phe Pro Ala Asp Pro Thr Gly Arg
        115                 120                 125

Gly Arg Gly Arg Gly Gly Arg Gly Ala Met Pro Ala Met Gln Gly
            130                 135                 140

Val Met Pro Gly Val Ala Tyr Pro Gly Met Pro Met Gly Gly Val Gly
145                 150                 155                 160

Met Glu Pro Thr Gly Glu Pro Ser Gly Leu Gln Val Val Val His Asn
```

```
                165                 170                 175

Leu Pro Trp Ser Cys Gln Trp Gln Gln Leu Lys Asp His Phe Lys Glu
            180                 185                 190

Trp Arg Val Glu Arg Ala Asp Val Val Tyr Asp Ala Trp Gly Arg Ser
        195                 200                 205

Arg Gly Phe Gly Thr Val Arg Phe Thr Thr Lys Glu Asp Ala Ala Thr
    210                 215                 220

Ala Cys Asp Lys Leu Asn Asn Ser Gln Ile Asp Gly Arg Thr Ile Ser
225                 230                 235                 240

Val Arg Leu Asp Arg Phe Ala
            245

<210> SEQ ID NO 7
<211> LENGTH: 226
<212> TYPE: PRT
<213> ORGANISM: Chlamydomonas incerta
<220> FEATURE:
<221> NAME/KEY: MISC_FEATURE
<223> OTHER INFORMATION: putative nucleic acid-binding protein, partial

<400> SEQUENCE: 7

Met Gly Glu Gln Leu Arg Gln Gln Gly Thr Val Lys Trp Phe Asn Ala
1               5                   10                  15

Thr Lys Gly Phe Gly Phe Ile Thr Pro Gly Gly Gly Glu Asp Leu
            20                  25                  30

Phe Val His Gln Thr Asn Ile Asn Ser Glu Gly Phe Arg Ser Leu Arg
        35                  40                  45

Glu Gly Glu Ala Val Glu Phe Glu Val Glu Ala Gly Pro Asp Gly Arg
    50                  55                  60

Ser Lys Ala Val Asn Val Thr Gly Pro Ala Gly Ala Ala Pro Glu Gly
65                  70                  75                  80

Ala Pro Arg Asn Phe Arg Gly Gly Arg Gly Arg Gly Arg Ala Arg
            85                  90                  95

Gly Ala Arg Gly Gly Tyr Ala Ala Ala Tyr Gly Tyr Pro Gln Met Ala
            100                 105                 110

Pro Val Tyr Pro Gly Tyr Tyr Phe Phe Pro Ala Asp Pro Thr Gly Arg
        115                 120                 125

Gly Arg Gly Arg Gly Gly Arg Gly Gly Ala Met Pro Gly Met Gln Gly
    130                 135                 140

Val Met Pro Gly Val Ala Tyr Pro Gly Met Pro Met Gly Gly Val Gly
145                 150                 155                 160

Met Glu Ala Thr Gly Asp Pro Ser Gly Leu Gln Val Val His Asn
            165                 170                 175

Leu Pro Trp Ser Cys Gln Trp Gln Gln Leu Lys Asp His Phe Lys Glu
            180                 185                 190

Trp Arg Val Glu Arg Ala Asp Val Val Tyr Asp Ala Trp Gly Arg Ser
        195                 200                 205

Arg Gly Phe Gly Thr Val Arg Phe Thr Thr Lys Glu Asp Ala Ala Met
    210                 215                 220

Ala Cys
225

<210> SEQ ID NO 8
<211> LENGTH: 242
<212> TYPE: PRT
<213> ORGANISM: Volvox carteri f. nagariensis
<220> FEATURE:
```

<221> NAME/KEY: MISC_FEATURE
<223> OTHER INFORMATION: nucleic acid binding protein

<400> SEQUENCE: 8

Met Gly Glu Gln Leu Arg Gln Arg Gly Thr Val Lys Trp Phe Asn Ala
1               5                   10                  15

Thr Lys Gly Phe Gly Phe Ile Thr Pro Glu Gly Gly Glu Asp Phe
            20                  25                  30

Phe Val His Gln Thr Asn Ile Asn Ser Asp Gly Phe Arg Ser Leu Arg
            35                  40                  45

Glu Gly Glu Ala Val Glu Phe Glu Val Glu Ala Gly Pro Asp Gly Arg
50                  55                  60

Ser Lys Ala Val Ser Val Ser Gly Pro Gly Gly Ser Ala Pro Glu Gly
65                  70                  75                  80

Ala Pro Arg Asn Phe Arg Gly Gly Arg Gly Arg Gly Arg Ala Arg
            85                  90                  95

Gly Ala Arg Gly Ala Tyr Ala Ala Tyr Gly Tyr Pro Gln Met Pro Pro
            100                 105                 110

Met Tyr Pro Gly Tyr Tyr Phe Phe Pro Ala Asp Pro Thr Gly Arg Gly
            115                 120                 125

Arg Gly Arg Gly Arg Gly Met Pro Ile Gln Gly Met Ile Gln Gly
            130                 135                 140

Met Pro Tyr Pro Gly Ile Pro Ile Pro Gly Gly Leu Glu Pro Thr Gly
145                 150                 155                 160

Glu Pro Ser Gly Leu Gln Val Val His Asn Leu Pro Trp Ser Cys
            165                 170                 175

Gln Trp Gln Gln Leu Lys Asp His Phe Lys Glu Trp Arg Val Glu Arg
            180                 185                 190

Ala Asp Val Val Tyr Asp Ala Trp Gly Arg Ser Arg Gly Phe Gly Thr
            195                 200                 205

Val Arg Phe Ala Thr Lys Glu Asp Ala Ala Gln Ala Cys Glu Lys Met
            210                 215                 220

Asn Asn Ser Gln Ile Asp Gly Arg Thr Ile Ser Val Arg Leu Asp Arg
225                 230                 235                 240

Phe Glu

<210> SEQ ID NO 9
<211> LENGTH: 178
<212> TYPE: PRT
<213> ORGANISM: Physcomitrella patens,
<220> FEATURE:
<221> NAME/KEY: MISC_FEATURE
<223> OTHER INFORMATION: predicted protein, partial

<400> SEQUENCE: 9

Ala Lys Glu Thr Gly Lys Val Lys Trp Phe Asn Ser Ser Lys Gly Phe
1               5                   10                  15

Gly Phe Ile Thr Pro Asp Lys Gly Gly Glu Asp Leu Phe Val His Gln
            20                  25                  30

Thr Ser Ile His Ala Glu Gly Phe Arg Ser Leu Arg Glu Gly Glu Val
            35                  40                  45

Val Glu Phe Gln Val Glu Ser Ser Glu Asp Gly Arg Thr Lys Ala Leu
            50                  55                  60

Ala Val Thr Gly Pro Gly Gly Ala Phe Val Gln Gly Ala Ser Tyr Arg
65                  70                  75                  80

Arg Asp Gly Tyr Gly Gly Pro Gly Arg Gly Ala Gly Glu Gly Gly Gly

```
                    85                  90                  95
Arg Gly Thr Val Gly Gly Ala Gly Arg Gly Arg Gly Arg Gly Arg
                100                 105                 110
Gly Val Gly Gly Phe Val Gly Glu Arg Ser Gly Ala Ala Gly Glu
                115                 120                 125
Arg Thr Cys Tyr Asn Cys Gly Glu Gly Gly His Ile Ala Arg Glu Cys
                130                 135                 140
Gln Asn Glu Ser Thr Gly Asn Ala Arg Gln Gly Gly Gly Gly
145                 150                 155                 160
Gly Asn Arg Ser Cys Tyr Thr Cys Gly Glu Ala Gly His Leu Ala Arg
                165                 170                 175
Asp Cys

<210> SEQ ID NO 10
<211> LENGTH: 444
<212> TYPE: PRT
<213> ORGANISM: Zea mays
<220> FEATURE:
<221> NAME/KEY: MISC_FEATURE
<223> OTHER INFORMATION: unknown

<400> SEQUENCE: 10

Met Ala Ala Ala Arg Gln Arg Gly Thr Val Lys Trp Phe Asn Asp
1               5                   10                  15
Thr Lys Gly Phe Gly Phe Ile Ser Pro Glu Asp Gly Ser Glu Asp Leu
                20                  25                  30
Phe Val His Gln Ser Ser Ile Lys Ser Glu Gly Phe Arg Ser Leu Ala
                35                  40                  45
Glu Gly Glu Glu Val Glu Phe Ser Val Ser Glu Gly Asp Asp Gly Arg
                50                  55                  60
Thr Lys Ala Val Asp Val Thr Gly Pro Asp Gly Ser Ser Ala Ser Gly
65                  70                  75                  80
Ser Arg Leu Leu His Asp Gly Ala Trp Arg Pro Phe Cys Ile Phe Thr
                85                  90                  95
Ser Thr Arg Gln Pro Glu Gln His Arg Gly Ser Gly Ser Asp Arg His
                100                 105                 110
Asp Gly Gly Asp Tyr Asn His Pro Lys Pro Gln Ala Ile Ala Ala Gly
                115                 120                 125
Ala His Ser Leu Leu Leu Thr Arg Ala Cys Leu Ser Ser Lys Ser Pro
                130                 135                 140
Pro Pro Ser Leu Ala Val Gly Leu Leu Ser Val Leu Ala Gln Arg Thr
145                 150                 155                 160
Gly Pro Thr Pro Gly Thr Thr Gly Ser Ala Ala Ser Leu Ser Gly Ser
                165                 170                 175
Ser Pro Ile Ser Leu Gly Phe Asn Pro Thr Ser Phe Leu Pro Phe Leu
                180                 185                 190
Gln Thr Ala Arg Trp Leu Pro Cys Ser Asp Leu Ala Thr Ser Ser Ser
                195                 200                 205
Ser Ala Pro Ser Pro Pro Arg Ser Leu Ala Pro Ser Ala Pro Pro
210                 215                 220
Lys Lys Ala Leu Ile Gly Ala Ser Thr Gly Thr Gly Ile Ala Thr
225                 230                 235                 240
Ser Ser Gly Ala Gly Ala Ala Met Ser Arg Ser Asn Trp Leu Ser Arg
                245                 250                 255
Trp Val Ser Ser Cys Ser Asp Asp Ala Lys Thr Ala Phe Ala Ala Val
```

-continued

```
                260                 265                 270
Thr Val Pro Leu Leu Tyr Gly Ser Ser Leu Ala Glu Pro Lys Ser Ile
            275                 280                 285

Pro Ser Lys Ser Met Tyr Pro Thr Phe Asp Val Gly Asp Arg Ile Leu
        290                 295                 300

Ala Glu Lys Val Ser Tyr Ile Phe Arg Asp Pro Glu Ile Ser Asp Ile
305                 310                 315                 320

Val Ile Phe Arg Ala Pro Pro Gly Leu Gln Val Tyr Gly Tyr Ser Ser
                325                 330                 335

Gly Asp Val Phe Ile Lys Arg Val Ala Lys Gly Asp Tyr Val
            340                 345                 350

Glu Val Arg Asp Gly Lys Leu Phe Val Asn Gly Val Gln Asp Glu
        355                 360                 365

Asp Phe Val Leu Glu Pro His Asn Tyr Glu Met Glu Pro Val Leu Val
                370                 375                 380

Pro Glu Gly Tyr Val Phe Val Leu Gly Asp Asn Arg Asn Asn Ser Phe
385                 390                 395                 400

Asp Ser His Asn Trp Gly Pro Leu Pro Val Arg Asn Ile Val Gly Arg
                405                 410                 415

Ser Ile Leu Arg Tyr Trp Pro Pro Ser Lys Ile Asn Asp Thr Ile Tyr
                420                 425                 430

Glu Pro Asp Val Ser Arg Leu Thr Val Pro Ser Ser
            435                 440

<210> SEQ ID NO 11
<211> LENGTH: 197
<212> TYPE: PRT
<213> ORGANISM: Oryza sativa
<220> FEATURE:
<221> NAME/KEY: MISC_FEATURE
<223> OTHER INFORMATION: Japonica Group

<400> SEQUENCE: 11

Met Ala Ser Glu Arg Val Lys Gly Thr Val Lys Trp Phe Asp Ala Thr
1               5                   10                  15

Lys Gly Phe Gly Phe Ile Thr Pro Asp Asp Gly Glu Asp Leu Phe
            20                  25                  30

Val His Gln Ser Ser Leu Lys Ser Asp Gly Tyr Arg Ser Leu Asn Asp
        35                  40                  45

Gly Asp Val Val Glu Phe Ser Val Gly Ser Gly Asn Asp Gly Arg Thr
    50                  55                  60

Lys Ala Val Asp Val Thr Ala Pro Gly Gly Ala Leu Thr Gly Gly
65                  70                  75                  80

Ser Arg Pro Ser Gly Gly Asp Arg Gly Tyr Gly Gly Gly Gly
            85                  90                  95

Gly Gly Arg Tyr Gly Gly Asp Arg Gly Tyr Gly Gly Gly Gly Gly
                100                 105                 110

Tyr Gly Gly Gly Asp Arg Gly Tyr Gly Gly Gly Gly Tyr Gly Gly
            115                 120                 125

Gly Gly Gly Gly Gly Ser Arg Ala Cys Tyr Lys Cys Gly Glu Glu Gly
        130                 135                 140

His Met Ala Arg Asp Cys Ser Gln Gly Gly Gly Gly Gly Gly Tyr
145                 150                 155                 160

Gly Gly Gly Gly Gly Gly Tyr Arg Gly Gly Gly Gly Gly Gly
                165                 170                 175
```

Gly Gly Cys Tyr Asn Cys Gly Glu Thr Gly His Ile Ala Arg Glu Cys
            180                 185                 190

Pro Ser Lys Thr Tyr
        195

<210> SEQ ID NO 12
<211> LENGTH: 139
<212> TYPE: PRT
<213> ORGANISM: Chlorella variabilis

<400> SEQUENCE: 12

Met Ala Ala Ala Lys Ala Thr Gly Thr Val Lys Trp Gly Tyr Gly Phe
1               5                   10                  15

Ile Thr Pro Asp Ser Gly Gly Glu Asp Leu Phe Val His Gln Thr Ala
            20                  25                  30

Ile Val Ser Glu Gly Phe Arg Ser Leu Arg Glu Gly Glu Pro Val Glu
        35                  40                  45

Phe Phe Val Glu Thr Ser Asp Asp Gly Arg Gln Lys Ala Val Asn Val
    50                  55                  60

Thr Gly Pro Asn Gly Ala Ala Pro Glu Gly Ala Pro Arg Arg Gln Phe
65                  70                  75                  80

Asp Asp Gly Tyr Gly Ala Gly Gly Gly Gly Ser Tyr Gly Gly Gly
                85                  90                  95

Phe Gly Gly Gly Gly Gly Gly Arg Arg Gly Gly Arg Gly Gly
            100                 105                 110

Gly Gly Tyr Gly Gly Gly Tyr Gly Gly Gly Tyr Asp Gln Gly Gly
            115                 120                 125

Tyr Gly Gly Gln Pro Pro Ile Ala Cys Asn Met
        130                 135

<210> SEQ ID NO 13
<211> LENGTH: 182
<212> TYPE: PRT
<213> ORGANISM: Selaginella moellendorffii
<220> FEATURE:
<221> NAME/KEY: MISC_FEATURE
<223> OTHER INFORMATION: hypothetical protein

<400> SEQUENCE: 13

Met Ala Ser Pro Ala Asp Ala Lys Arg Thr Gly Lys Val Lys Trp Phe
1               5                   10                  15

Asn Val Thr Lys Gly Phe Gly Phe Ile Thr Pro Asp Asp Gly Ser Glu
            20                  25                  30

Glu Leu Phe Val His Gln Ser Ala Ile Phe Ala Glu Gly Phe Arg Ser
        35                  40                  45

Leu Arg Glu Gly Glu Ile Val Glu Phe Ser Val Glu Gln Gly Glu Asp
    50                  55                  60

Gln Arg Met Arg Ala Ala Asp Val Thr Gly Pro Asp Gly Ser His Val
65                  70                  75                  80

Gln Gly Ala Pro Ser Ser Phe Gly Ser Arg Gly Gly Gly Gly Gly
                85                  90                  95

Gly Arg Gly Gly Arg Gly Arg Ala Gly Gly Asp Asn Pro Ile Val
            100                 105                 110

Cys Tyr Asn Cys Asn Glu Ala Gly His Val Ser Arg Asp Cys Lys Tyr
        115                 120                 125

Gln Gln Glu Gly Gly Gly Gly Gly Gly Gly Gly Arg Gly
            130                 135                 140

```
Pro Pro Ser Gly Arg Arg Gly Gly Ala Gly Gly Ser Gly Gly
145                 150                 155                 160

Gly Gly Arg Gly Cys Phe Thr Cys Gly Ala Gln Gly His Ile Ser Arg
            165                 170                 175

Asp Cys Pro Ser Asn Tyr
            180
```

<210> SEQ ID NO 14
<211> LENGTH: 208
<212> TYPE: PRT
<213> ORGANISM: vitis vinifera
<220> FEATURE:
<221> NAME/KEY: MISC_FEATURE
<223> OTHER INFORMATION: cold shock domain protein 3

<400> SEQUENCE: 14

```
Met Ala Gln Glu Arg Ser Thr Gly Val Val Arg Trp Phe Ser Asp Gln
1               5                   10                  15

Lys Gly Phe Gly Phe Ile Thr Pro Asn Glu Gly Gly Glu Asp Leu Phe
                20                  25                  30

Val His Gln Ser Ser Ile Lys Ser Asp Gly Phe Arg Ser Leu Gly Glu
            35                  40                  45

Gly Glu Thr Val Glu Phe Gln Ile Val Leu Gly Glu Asp Gly Arg Thr
        50                  55                  60

Lys Ala Val Asp Val Thr Gly Pro Asp Gly Ser Ser Val Gln Gly Ser
65                  70                  75                  80

Lys Arg Asp Asn Tyr Gly Gly Gly Gly Gly Gly Ile Ala Ser Glu
                85                  90                  95

Glu Ile Met Ala Ala Ala Ala Val Val Glu Glu Ala Glu Ala
                100                 105                 110

Glu Val Val Ile Pro Ala Val Ala Val Ala Val Ile Thr Val Val
            115                 120                 125

Ile Met Gly Thr Trp Leu Gly Ile Ala Leu Trp Lys Ala Ala Ala Leu
        130                 135                 140

Val Gly Ser Val Val Ala Glu Val Glu Ala Val Glu Gly Leu Val Ala
145                 150                 155                 160

Val Ala Val Asp Ala Thr Thr Val Asp Arg Lys Gly Ile Leu Leu Glu
                165                 170                 175

Asn Ala Leu Thr Leu Thr His Arg Asp Glu Gly Lys Arg Gly Val Ile
            180                 185                 190

Val Tyr Ile Leu Phe Phe Pro Ala Ser Ser Lys Ile Phe Phe Pro Val
        195                 200                 205
```

<210> SEQ ID NO 15
<211> LENGTH: 231
<212> TYPE: PRT
<213> ORGANISM: Triticum aestivum
<220> FEATURE:
<221> NAME/KEY: MISC_FEATURE
<223> OTHER INFORMATION: cold shock domain protein 3

<400> SEQUENCE: 15

```
Met Gly Glu Arg Val Lys Gly Thr Val Lys Trp Phe Asn Val Thr Lys
1               5                   10                  15

Gly Phe Gly Phe Ile Ser Pro Asp Asp Gly Gly Glu Asp Leu Phe Val
                20                  25                  30

His Gln Ser Ala Ile Lys Ser Asp Gly Tyr Arg Ser Leu Asn Glu Asn
            35                  40                  45
```

```
Asp Ala Val Glu Phe Glu Ile Ile Thr Gly Asp Asp Gly Arg Thr Lys
 50                  55                  60

Ala Ser Asp Val Thr Ala Pro Gly Gly Gly Ala Leu Ser Gly Gly Ser
 65                  70                  75                  80

Arg Pro Gly Glu Gly Gly Gly Asp Arg Gly Gly Arg Gly Gly Tyr Gly
                 85                  90                  95

Gly Gly Gly Gly Gly Tyr Gly Gly Gly Gly Gly Tyr Gly Gly
            100                 105                 110

Gly Gly Gly Tyr Gly Gly Gly Gly Gly Tyr Gly Gly Gly Tyr
            115                 120                 125

Gly Gly Gly Gly Gly Gly Arg Gly Cys Tyr Lys Cys Gly Glu Asp
 130                 135                 140

Gly His Ile Ser Arg Asp Cys Pro Gln Gly Gly Gly Gly Gly Gly
 145                 150                 155                 160

Tyr Gly Gly Gly Gly Tyr Gly Gly Gly Gly Gly Gly Arg Glu Cys
                 165                 170                 175

Tyr Lys Cys Gly Glu Glu Gly His Ile Ser Arg Asp Cys Pro Gln Gly
                 180                 185                 190

Gly Gly Gly Gly Gly Tyr Gly Gly Gly Gly Arg Gly Gly Gly Gly
                 195                 200                 205

Gly Gly Gly Gly Cys Phe Ser Cys Gly Glu Ser Gly His Phe Ser Arg
 210                 215                 220

Glu Cys Pro Asn Lys Ala His
 225                 230
```

<210> SEQ ID NO 16
<211> LENGTH: 135
<212> TYPE: PRT
<213> ORGANISM: Cryptosporidium parvum Iowa II
<220> FEATURE:
<221> NAME/KEY: MISC_FEATURE
<223> OTHER INFORMATION: cold shock RNA binding domain of the OB fold,
      partial

<400> SEQUENCE: 16

```
Glu Lys Pro Ile Lys Leu Val Lys Met Pro Leu Ser Gly Val Cys Lys
 1               5                  10                  15

Trp Phe Asp Ser Thr Lys Gly Phe Gly Phe Ile Thr Pro Asp Asp Gly
                 20                  25                  30

Ser Glu Asp Ile Phe Val His Gln Gln Asn Ile Lys Val Glu Gly Phe
             35                  40                  45

Arg Ser Leu Ala Gln Asp Glu Arg Val Glu Tyr Glu Ile Glu Thr Asp
 50                  55                  60

Asp Lys Gly Arg Arg Lys Ala Val Asn Val Ser Gly Pro Asn Gly Ala
 65                  70                  75                  80

Pro Val Lys Gly Asp Arg Arg Gly Arg Gly Arg Gly Arg Gly Arg
                 85                  90                  95

Gly Met Arg Gly Arg Gly Arg Gly Gly Arg Gly Arg Gly Phe Tyr Gln
                100                 105                 110

Asn Gln Asn Gln Ser Gln Pro Gln Ser Gln Gln Gln Pro Val Ser Thr
            115                 120                 125

Gln Ser Gln Pro Val Ala His
            130                 135
```

<210> SEQ ID NO 17
<211> LENGTH: 301
<212> TYPE: PRT

<213> ORGANISM: Arabidopsis thaliana
<220> FEATURE:
<221> NAME/KEY: MISC_FEATURE
<223> OTHER INFORMATION: cold shock domain protein 3

<400> SEQUENCE: 17

```
Met Ala Met Glu Asp Gln Ser Ala Ala Arg Ser Ile Gly Lys Val Ser
1               5                   10                  15

Trp Phe Ser Asp Gly Lys Gly Tyr Gly Phe Ile Thr Pro Asp Asp Gly
            20                  25                  30

Gly Glu Glu Leu Phe Val His Gln Ser Ser Ile Val Ser Asp Gly Phe
        35                  40                  45

Arg Ser Leu Thr Leu Gly Glu Ser Val Glu Tyr Glu Ile Ala Leu Gly
    50                  55                  60

Ser Asp Gly Lys Thr Lys Ala Ile Glu Val Thr Ala Pro Gly Gly Gly
65                  70                  75                  80

Ser Leu Asn Lys Lys Glu Asn Ser Ser Arg Gly Ser Gly Gly Asn Cys
                85                  90                  95

Phe Asn Cys Gly Glu Val Gly His Met Ala Lys Asp Cys Asp Gly Gly
            100                 105                 110

Ser Gly Gly Lys Ser Phe Gly Gly Gly Gly Arg Arg Ser Gly Gly
        115                 120                 125

Glu Gly Glu Cys Tyr Met Cys Gly Asp Val Gly His Phe Ala Arg Asp
    130                 135                 140

Cys Arg Gln Ser Gly Gly Gly Asn Ser Gly Gly Gly Gly Gly Gly
145                 150                 155                 160

Arg Pro Cys Tyr Ser Cys Gly Glu Val Gly His Leu Ala Lys Asp Cys
                165                 170                 175

Arg Gly Gly Ser Gly Gly Asn Arg Tyr Gly Gly Gly Gly Arg Gly
            180                 185                 190

Ser Gly Gly Asp Gly Cys Tyr Met Cys Gly Gly Val Gly His Phe Ala
        195                 200                 205

Arg Asp Cys Arg Gln Asn Gly Gly Asn Val Gly Gly Gly Gly Ser
    210                 215                 220

Thr Cys Tyr Thr Cys Gly Gly Val Gly His Ile Ala Lys Val Cys Thr
225                 230                 235                 240

Ser Lys Ile Pro Ser Gly Gly Gly Gly Gly Arg Ala Cys Tyr Glu
                245                 250                 255

Cys Gly Gly Thr Gly His Leu Ala Arg Asp Cys Asp Arg Arg Gly Ser
            260                 265                 270

Gly Ser Ser Gly Gly Gly Gly Ser Asn Lys Cys Phe Ile Cys Gly
        275                 280                 285

Lys Glu Gly His Phe Ala Arg Glu Cys Thr Ser Val Ala
    290                 295                 300
```

<210> SEQ ID NO 18
<211> LENGTH: 13
<212> TYPE: DNA
<213> ORGANISM: chlamydomonas reinhardtii
<220> FEATURE:
<221> NAME/KEY: misc_feature
<223> OTHER INFORMATION: consensus sequence LHCBM1

<400> SEQUENCE: 18
gctgggacac cgc                                                      13

<210> SEQ ID NO 19

```
<211> LENGTH: 13
<212> TYPE: DNA
<213> ORGANISM: chlamydomonas reinhardtii
<220> FEATURE:
<221> NAME/KEY: misc_feature
<223> OTHER INFORMATION: Consensus sequence LHCBM2

<400> SEQUENCE: 19
gcgacacccc cgc                                                          13

<210> SEQ ID NO 20
<211> LENGTH: 13
<212> TYPE: DNA
<213> ORGANISM: chlamydomonas reinhardtii
<220> FEATURE:
<221> NAME/KEY: misc_feature
<223> OTHER INFORMATION: Consensus sequence LHCBM2
<220> FEATURE:
<221> NAME/KEY: misc_feature
<223> OTHER INFORMATION: Consensus sequence LHCBM3

<400> SEQUENCE: 20
gctggaccac cgt                                                          13

<210> SEQ ID NO 21
<211> LENGTH: 13
<212> TYPE: DNA
<213> ORGANISM: chlamydomonas reinhardtii
<220> FEATURE:
<221> NAME/KEY: misc_feature
<223> OTHER INFORMATION: Consensus sequence LHCBM3
<220> FEATURE:
<221> NAME/KEY: misc_feature
<223> OTHER INFORMATION: Consensus sequence LHCBM4

<400> SEQUENCE: 21
gcctgacccc cga                                                          13

<210> SEQ ID NO 22
<211> LENGTH: 13
<212> TYPE: DNA
<213> ORGANISM: chlamydomonas reinhardtii
<220> FEATURE:
<221> NAME/KEY: misc_feature
<223> OTHER INFORMATION: Consensus sequence LHCBM5

<400> SEQUENCE: 22
gcatcacccc cga                                                          13

<210> SEQ ID NO 23
<211> LENGTH: 13
<212> TYPE: DNA
<213> ORGANISM: chlamydomonas reinhardtii
<220> FEATURE:
<221> NAME/KEY: misc_feature
<223> OTHER INFORMATION: Consensus sequence LHCBM6

<400> SEQUENCE: 23
gccagacccc cga                                                          13

<210> SEQ ID NO 24
<211> LENGTH: 13
<212> TYPE: DNA
<213> ORGANISM: chlamydomonas reinhardtii
<220> FEATURE:
<221> NAME/KEY: misc_feature
<223> OTHER INFORMATION: Consensus sequence LHCBM8

<400> SEQUENCE: 24
```

-continued

```
gcgacacccc cgc                                                        13

<210> SEQ ID NO 25
<211> LENGTH: 13
<212> TYPE: DNA
<213> ORGANISM: chlamydomonas reinhardtii
<220> FEATURE:
<221> NAME/KEY: misc_feature
<223> OTHER INFORMATION: Consensus sequence LHCBM9

<400> SEQUENCE: 25
tccataccac cgt                                                        13

<210> SEQ ID NO 26
<211> LENGTH: 13
<212> TYPE: DNA
<213> ORGANISM: chlamydomonas reinhardtii
<220> FEATURE:
<221> NAME/KEY: misc_feature
<223> OTHER INFORMATION: CSDCS
<220> FEATURE:
<221> NAME/KEY: misc_feature
<222> LOCATION: (5)..(5)
<223> OTHER INFORMATION: n is a, c, g,or t

<400> SEQUENCE: 26
gccanaccac cgc                                                        13

<210> SEQ ID NO 27
<211> LENGTH: 13
<212> TYPE: DNA
<213> ORGANISM: Chlamydomonas reinhardtii
<220> FEATURE:
<221> NAME/KEY: misc_feature
<223> OTHER INFORMATION: LRE (Light responsive element)

<400> SEQUENCE: 27
gccagacccc cgc                                                        13

<210> SEQ ID NO 28
<211> LENGTH: 21
<212> TYPE: DNA
<213> ORGANISM: artificial
<220> FEATURE:
<223> OTHER INFORMATION: forward primers homologous to A. thaliana cao

<400> SEQUENCE: 28
atgaacgccg ccgtgtttag t                                               21

<210> SEQ ID NO 29
<211> LENGTH: 21
<212> TYPE: DNA
<213> ORGANISM: artificial
<220> FEATURE:
<223> OTHER INFORMATION: reverse primer homologous to A. thalianan cao
      sequence

<400> SEQUENCE: 29
cggttcagcg caatgtctcc a                                               21
```